US006528630B1

(12) United States Patent
Williams et al.

(10) Patent No.: US 6,528,630 B1
(45) Date of Patent: Mar. 4, 2003

(54) CALCIUM CHANNEL COMPOSITIONS AND METHODS

(75) Inventors: Mark E. Williams, Carlsad; Kenneth A. Stauderman, San Diego; Michael M. Harpold, El Cajon, all of CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/984,709

(22) Filed: Dec. 3, 1997

(51) Int. Cl.[7] .......................... C12N 15/11; C12N 15/00; C07H 21/04; C07K 5/00
(52) U.S. Cl. .................... 536/23.1; 536/23.1; 536/23.5; 514/12; 514/14; 435/69.1; 435/325; 435/354
(58) Field of Search ............................... 435/4, 6, 69.1, 435/70.3, 325, 354, 358, 363, 366; 536/23.1, 23.5

(56) References Cited

U.S. PATENT DOCUMENTS

| | | | |
|---|---|---|---|
| 4,675,285 A | 6/1987 | Clark et al. | 435/6 |
| 4,766,072 A | 8/1988 | Jendrisak et al. | 435/91 |
| 4,788,135 A | 11/1988 | Davis et al. | 435/6 |
| 4,906,564 A | 3/1990 | Lyon et al. | 435/7 |
| 4,912,202 A | 3/1990 | Campbell et al. | 530/387 |
| 4,950,739 A | 8/1990 | Cherksey et al. | 530/350 |
| 4,954,436 A | 9/1990 | Froehner et al. | 435/7 |
| 5,051,403 A | 9/1991 | Miljanich et al. | 514/12 |
| 5,189,020 A | 2/1993 | Miljanich et al. | 514/12 |
| 5,264,371 A | 11/1993 | Miljanich et al. | 436/503 |
| 5,386,025 A | 1/1995 | Jay et al. | 536/23.5 |
| 5,407,820 A | 4/1995 | Ellis et al. | 435/240.2 |
| 5,424,218 A | 6/1995 | Miljanich et al. | 436/503 |
| 5,429,921 A | 7/1995 | Harpold et al. | 435/4 |
| 5,618,720 A | * 4/1997 | Ellis et al. | 435/325 |
| 5,643,750 A | 7/1997 | Spreyer et al. | 435/69.1 |
| 5,686,241 A | 11/1997 | Ellis et al. | 435/56 |
| 5,792,846 A | 8/1998 | Harpold et al. | 536/23.1 |
| 5,846,757 A | 12/1998 | Harpold et al. | 435/29 |
| 5,851,824 A | 12/1998 | Harpold et al. | 435/325 |

FOREIGN PATENT DOCUMENTS

| | | |
|---|---|---|
| CA | 2085502 | 2/1993 |
| EP | 0266881 | 9/1987 |
| EP | 0355738 | 2/1990 |
| EP | 0441755 | 1/1991 |
| EP | 0507170 | 10/1992 |
| EP | 0556651 | 7/1995 |
| JP | 6040955 | 3/1985 |
| JP | 0259647 | 8/1990 |
| JP | 0385455 | 4/1991 |
| WO | 8907608 | 8/1989 |
| WO | 9115602 | 10/1991 |
| WO | 9202639 | 2/1992 |
| WO | 9213092 | 8/1992 |
| WO | 9308469 | 4/1993 |
| WO | 9313423 | 7/1993 |
| WO | 9314098 | 7/1993 |
| WO | 9402511 | 2/1994 |
| WO | 9504144 | 2/1995 |
| WO | 9504822 | 2/1995 |
| WO | 9639512 | 12/1996 |

OTHER PUBLICATIONS

Adams, et al., "Intramembrane charge movement restored in dysgenic skeletal muscle by injection of dihydropyridine receptor cDNAs," *Nature*, 346: 569–572 (1990).

Adams, M.D., et al. (Jun. 30, 1993) Gen Bank Record No. T05783, "EST03672"; (Jun. 30, 1993) Gen Bank Record No. T06059, EST03948.

Ahlijanian, et al., "Subunit structure and localization of dihydropyridine–sensitive calcium channels in mammalian brain, spinal cord, and retina," *Neuron*, 4: 819–832 (1990).

Ahlijanian, et al., "Phosphorylation of an α1–like subunit of an w–conotoxin–sensitive brain calcium channel by cAMP–dependent protein kinase and protein kinase C," *J.Biol.Chem.*, 266: 20192 (1991).

Akong et al., "High–throughput measurement of intracellular $Ca^{2+}$ by fluorescence imaging of a 96–well microtiter plate," *Soc. Neurosci. Abstr. 21* (1995).

Artalejo, et al., "w–Conotoxin GVIA blocks a $Ca^{2+}$ current in bovine chromaffin cells that is not of the 'classic' N type," *Neuron*, 8: 85–95 (1992).

Ausubel et al., *Current Protocols in Molecular Biology*, Wiley & Sons, Inc. vol. 1, 2 and 3.

Barhanin, et al., "The calcium channel antagonists receptor from rabbit skeletal muscle: reconstitution after publication and subunit characterization," *Eur.J.Biochem.*, 164: 525–531 (1987).

Bezprozvanny and Tsien, "Voltage–dependent blockade of diverse types of voltage–gated $Ca^{2+}$ channels expressed in Xenopus oocytes by the $Ca^{2+}$ channel antagonist mibefradil (Ro 40–5967)," *Mol. Pharmacol.* 48:540–549 (1995).

Biagi et al., "Membrane currents in a calcitonin–secreting human C cell line", *Am. J. Physiol.* 263:C986–C994 (1992).

Biel, et al., "Primary structure and functional expression of a high voltage activated calcium channel from rabbit lung," *FEBS Letters*, 269(2): 409–412 (1990).

Blackshear, et al., "Protein kinase C–dependent and –independent pathways of proto–oncogene induction in human astrocytoma cells," *J. Biol. Chem.* 262(16):7774–7781 (1987).

(List continued on next page.)

*Primary Examiner*—Karen Cochrane Carlson
*Assistant Examiner*—Patricia Robinson
(74) *Attorney, Agent, or Firm*—Joseph A. Coppola; Jack L. Tribble

(57) ABSTRACT

Isolated nucleic acid encoding calcium channel $\alpha_{1F}$–subunits, including subunits encoded by nucleic acid that arises as splice variants of primary transcripts, is provided. Cells and vectors containing the nucleic acid and methods for identifying compounds that modulate the activity of calcium channels that contain $\alpha_{1F}$–subunits are also provided.

50 Claims, No Drawings

OTHER PUBLICATIONS

Blount, et al., "Assembly intermediates of the mouse muscle nicotinic Acetylcholine receptor in stably transfected fibroblasts," *J.Cell.Biol.,* 111: 2601 (1990).

Borsotto, et al., "The 1,4–dihydropyridine receptor associated with the skeletal muscle voltage–dependent $Ca^{2+}$ channel," *J.Biol.Chem.,* 260(26): 14255–14263 (1985).

Bosse, et al., "The cDNA and deduced amino acid sequence of the γ subunit of the L–type calcium channel from rabbit skeletal muscle," *FEBS,* 267(1): 153–156 (1990).

Boulter et al., "Functional expression of two neuronal nicotinic acetylcholine receptors from cDNA clones identifies a gene family," *Proc. Natl. Acad. Sci. USA* 84:7763–7767 (1987).

Breitbart et al.,, "Alternative splicing: a ubiquitous mechanism for the generation of multiple protein isoforms from single genes", *Ann. Rev. Biochem.* 56:467–495.

Brust, et al., "Human neuronal voltage–dependent calcium channels: Studies on subunit structure and role in channel assembly," *Neuropharmacology* 32(11):1089–1102 (1993).

Burns, et al., "Calcium channel activity of purified human synexin and structure of the human synexin gene," *Proc. Natl.Acad.Sci.,* 86: 3798–3802 (1989).

Campbell, et al., "The biochemistry and molecular biology of the dihydropyridine–sensitive calcium channel," *TINS,* 11(10): 425–430 (1988).

Campbell, et al., "32,000–Dalton subunit of the 1,4–dihydropyridine receptor," *Ann.N.Y.Acad.Sci.,* 560: 251–257 (1989).

Carbone, et al., "Ca currents in human neuroblastoma IMR32 cells: kinetics, permeability and pharmacology," *Pfluegers Arch.* 416: 170–179 (1990) (best available copy submitted).

Castellano, A., et al. "*Rattus norvegicus* cDNA sequence, complete 5' and 3' UTR's", GenBank database record, acc. No. L02135 (1993).

Castellano, A., et al, "Cloning and expression of a third calcium channel β subunit", *J. Biol. Chem.* 268:3450–55.

Castellano, A., et al. "Cloning and Expressions of a Neuronal Channel β Subunit",*J. Biol. Chem.* 268: 12359–12366 (1993).

Catterall, et al., "Molecular properties of dihydropyridine–sensitive calcium channels in skeletal muscle," *J.Biol.Chem.,* 263(8): 3535–3538 (1988).

Claudio, T., "Stable expression of transfected Torpedo acetylcholine receptor α subunits in mouse fibroblast L cells," *Proc.Natl.Acad.Sci.,* 84: 5967–5971 (1987).

Cohen, et al., "Distribution of $Ca^{2+}$ channels on frog motor nerve terminals revealed by fluorescent w–conotoxin," *J. of Neuroscience,* 11(4): 1032–1039 (1991).

Collin, et al., "Cloning, chromosomal location and functional expression of the human voltage–dependent calcium–channel β3 subunit," *Eur. J. Biochem.* 220:257–262 (1994).

Cooper, et al., "Purification and characterization of the dihydropyridine–sensitive voltage–dependent calcium channel from cardiac tissue," *J.Biol.Chem.,* 262(2): 509–512 (1987).

Cribbs et al., "Cloning and characterization of $\alpha_{1H}$ from human heart, a member of the T–type $Ca^{2+}$ channel gene family", *Circ. Res.* 83(1):103–109 (1998).

Cruz et al., "Characterization of ω –Conotoxin Target. Evidence for Tissue–Specific Heterogeneity ion Calcium Channel Types", *Biochem. J.* 26:820 (1987).

Curran and Morgan, "Barium modules c–fos expression and post–translational modification," *Proc.Natl.Acad.Sci.,* 83: 3521–8524 (1986).

Curtis, et al., "Purification of the calcium antagonist receptor of the voltage–sensitive calcium channel from skeletal muscle transverse tubules," *Biochemistry,* 23(10): 2113–2118 (1984).

Curtis, et al., "Reconstitution of the voltage–sensitive calcium channel purified from skeletal muscle transverse tubules," *Biochemistry,* 25: 3077–3083 (1986).

Dascal, et al., "Expression of modulation of voltage–gated calcium channels after RNA injection in Xenopus oocytes," *Science,* 231: 1147–1150 (1986).

Database WPI, Derwent # 199121, citing Japanese patent 3–85455, Automatic analysis device—comprises 2 or more reaction lines having differing reaction times adn 1 or more common treatment parts, and summarized translation of citation 4.

Database WPI, Derwent #199009, citing Japanese patent 2–59647, Automatic fluorophotometer in chemical analysis equipment—measuring intensity of fluorescence in intermittent series of reaction vessels using shutter controlling exciting incident light.

Database WPI, Derwent # 199241, citing European patent 507170, Cloned human neuronal calcium channel sub–types—useful in calcium flux assays to screen for neurone–specific calcium channel ligands.

Database WPI, Derwent # 199334, citing European patent 556651, Human neuronal beta–unit cDNA of voltage dependent calcium channels—useful in calcium–flux studies and screening systems for agonists and antagonists of calcium channels.

Database WPI, Derwent #01562455, citing Japanese patent 60–40955, Automatic micro–plate spectroscopic analysis apparatus and its method.

deBustros et al., "Cyclic AMP and phorbol esters separately induce growth inhibition, calcitonin secretion, and calcitonin gene transcription in cultured human medullary thyroid carcinoma", *J. of Bio Chem.* 261(17):8036–8041 (1986).

deBustros et al., "Differential utilization of calcitonin gene regulatory DNA sequences in cultured lines of medullary thyroid carcinoma and small–cell lung carcinoma", *Molecular Cell Biology* 10(4):1773–1778 (1990).

De Waard et al, "Subunit regulation of the neuronal $\alpha_{1A}$ $Ca^{2+}$ channel expressed in Xenopus oocytes", *J. of Physiol.* 485(3):619–634 (1995).

De Waard et al, "Identification of critical amino acids involved in $\alpha_1$–β interaction in voltage–dependent $Ca^{2+}$ channels", *FEBS Letters* 380:272–276 (1996).

De Jongh, et al., "Subunits of purified calcium channels," *J.Biol.Chem.,* 265(25): 14738–14741 (1990) (best available copy submitted).

De Jongh, et al., "Subunits of purified calcium channels: a 212–kDa form of $\alpha_1$ and partial amino acid sequence of a phosphorylation site of an independent β–subunit," *Proc. Natl.Acad.Sci. USA,* 86: 8585–8589 (1989).

Dubel et al., "Molecular cloning of the α–1 subunit of an ω–conotoxin–sensitive calcium channel", *Proc.Natl.Acad. Sci.* 89:5058–5062 (1992).

Elinor et al., "Functional expression of a rapidly inactivating neuronal calcium channel", *Nature 363*:455–458 (1993).

Elliot et al., "Role of calcium channel subtypes in calcium transients in hippocampal CA3 neurons", *J. Neurosci.* 15(10):6433–6444 (1995).

Ellis et al. (1988) "Sequence and Expression of mRNAs Encoding the $\alpha_1$ and $\alpha_2$ Subunits of a DHP–Sensitive Calcium Channel", *Science* 241:1661–1664.

Ellis et al., "Replacement of insulin receptor tyrosine residues 1162 and 1163 compromises insulin–stimulated kinase activity and uptake of 2–deoxyglucose," *Cell* 45:721–732 (1986).

Emori et al., Isolation and sequence analysis of cDNA clones for the small subunit of rabbit calcium–dependent protease, *J. Biol. Chem.* 261: 9472–9476 (1986).

Feramisco, et al., "Optimal spatial requirements for the location of basic residues in peptide substrates for the cyclic AMP–dependent protein kinase," *Journal of Biological Chemistry*, 255(9): 4240–4245 (1980).

Fisch, et al., "c–fos sequences necessary for basal expression and induction by epidermal growth factor, 12–0–tetradecanoyl phorbol–13–acetate, and the calcium inophore," *Mol.Cell.Biol.*, 7(10): 3490–3502 (1987).

Froehner, "New insights into the molecular structure of the dihydropyridine–sensitive calcium channel," *TINS*, 11(3): 90–92 (1988).

Gielow et al., "Resolution and pharmacological analysis of the voltage–dependent calcium channels of Drosophila larval muscles," *J. Neurosci.* 15(9):6085–6093 (1995).

Greenberg et al., "Stimulation of neuronal acetylcholine receptors induces rapid gene transcription," *Science* 234:80–83 (1986).

Gustin, et al., "Ion channels in yeast," *Science*, 233: 1195–1197 (1986).

Hackett, et al., DNA sequence analysis reveals extensive homologies of regiuons preceding hsp70 and $\alpha\beta$ heat shock genes in *Drosophila melanogaster, Proc. Natl. Acad. Sci. USA* 78: 6196–61200 (1981).

Hamilton, et al., "Subunit composition of the purified dihydropyridine binding protein from skeletal muscle," *Biochemistry*, 28: 7820–7828 (1989).

Hans, "Biophysical and pharmacological properties of a novel recombinant human low voltage activated (LVA) calcium channel in HEK293 cells", SIBIA Neurosciences, Inc. 1998 Annual Meeting, Losa Angeles, California Nov. 7–12, 1998.

Harpold, et al., "Human neuronal voltage–gated calcium channels: splice variants, subunit interactions and subtypes", *Low Voltage Act T–type Calcium Channels, Proc. Int. Electrophysiol. Meet.*, 218–228 (1998).

Hofmann, et al., "Regulation of the L–type calcium channel," *TINS*, 8: 393–398 (1987).

Horne, et al., "Molecular diversity of $Ca^{2+channel}$ $\alpha_1$ subunits from the marine ray *Discopyge ommata*", *Proc.Natl.Acad. Sci.* 90:3787–3791 (1993).

Hubbard, et al., "Synthesis and processing of asparagine–linked oligosaccharides[1,2]," *Ann.Rev.Biochem.*, 50: 555–583 (1981).

Huguenard, "Low–threshold calcium currents in central nervous system neurons", *Ann Rev. Physiol.* 58:329–48 (1996).

Hui, et al., "Molecular cloning of multiple subtypes of a novel rat brain isoform of the $\alpha_1$ subunit of the voltage–dependent calcium channel," *Nueron*, 7: 35–44 (1991).

Hullin, et al., "Calcium channel $\beta$ subunit heterogeneity: functional expression of cloned cDNA from heart, aorta and brain," *EMBO J.*, 11: 885 (1992).

Ichida, et al., "Photoaffinity labeling with dihydropyridine derivatives of crude membranes from rat skeletal, cardiac, ileal, and uterine muscles and whole brain," *J.Biochem.*, 105: 767–774 (1989).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol.Chem.*, 262(17): 8333–8339 (1987).

Ishibarshi, et al., "Regional difference of high voltage–activated $Ca^{2+}$ channels in rat CNS neurones," *NeuroReport* 6:1621–1624 (1995).

Jay, et al., "Structural characterization of the dihydropyridine–sensitive calcium channel $\alpha_2$–subunit and the associated $\delta$ peptides," *J.Biol.Chem.*, 266(5): 3287–3293 (1991).

Jay, et al., "Primary Structure of the $\gamma$ subunit of the DHP–sensitive calcium channel from skeletal muscle," *Science*, 248: 490–492 (1990).

Kasai, H., "Tonic inhibition and rebound facilitation of a neuronal calcium channel by a GTP–binding protein," *Proc. Natl.Acad.Sci. USA*, 88: 8855–8859 (1991).

Kim, et al., "Studies on the structural requirements for the activity of the skeletal muscle dihydropyridine receptor/slow $Ca^{2+}$ channel," *J.Biol.Chem.*, 11858–11863 (1990).

Kim, et al., "Rat brain expresses an alternatively spliced form of the dihydropyridine–sensitive L–type calcium channel $\alpha 2$ subunit," *Proc.Natl.Acad.Sci.*, 89:3251 (1992).

Koch, et al., "Characterization of cDNA clones encoding two putative isoforms of the $\alpha_1$–subunit of the dihydropyridine–sensitive voltage–dependent calcium channel isolated from rat brain and rat aorta," *FEBS Letters*, 250(2): 386–388 (1989).

Koch, et al., "cDNA cloning of a dihydropyridine–sensitive calcium channel from rat aorta," *J. of Biol.Chem.*, 265(29): 17786–17791 (1990).

Kozak, "An analysis of 5'–noncoding sequences from 699 vertebrate messenger RNAs," *Nucleic Acids Research*, 15(20): 8125–8148 (1987).

Lambert, et al, "T–type $Ca^{2+}$ current properties are not modified by $Ca^{2+}$ channel $\beta$ subunit depletion in nodosus ganglion neurons", *J. of Neurosc.* 17(17):6621–6628 (1997).

Lang, et al., "The effect of myasthenic syndrome antibody on presynaptic calcium channels in the mouse," *J.Physiol.*, 390: 257–270 (1987).

Lang et al., "The role of autoantibodies in Lambert–Eaton myasthenic syndrom[a]", *Ann.NY Acad. of Sci* 841:596–605 (1998).

Letts, et al., "The mouse stargazer gene encodes a neuronal $Ca^{2+}$–channel $\gamma$ subunit", *Nature Genetics* 19:340–347 (1998).

Leung, et al., "Structural characterization of the 1,4–dihydropyridine receptor of the voltage–dependent $Ca^{2+}$ channel from rabbit skeletal muscle," *J.Biol.Chem.*, 262(17): 7943–7946 (1987).

Leung, et al., "Monoclonal antibody characterization of the 1,4–dihydropyridine receptor of rabbit skeletal muscle," *Ann.N.Y.Acad.Sci.*, 522: 43–46 (1988).

Leung, et al., "Biochemical and ultrastructural characterization of the 1,4–dihydropyridine receptor from rabbit skeletal muscle," *J. of Biol.Chem.*, 263(2): 994–1001 (1988).

Leveque et al., "The synaptic vesicle protein synaptotagmim associates with calcium channels and is a putative Lambert–Eaton myasthenic syndrome antigen", *Proc.Natl.Acad. Sci.* 89:3625–3629 (1992).

Lotan, et al., "Specific block of calcium channel expression by a fragment of dihydropyridine receptor cDNA," *Science*, 243: 666–669 (1989).

Massa, et al., "Comparison of Fura–2 imaging and electrophysiological analysis of murine calcium channel α1 subunits coexpressed with Novel β2 subunit isoforms," *Molecular Pharmac* 47:707–716 (1995).

Meir et al., "Known calcium channel $\alpha^1$ subunits can form low threshold small conductance channels with similarities to native T–type channels", *Neuron* 20:341–351 (1998).

Mes–Masson et al., Overlapping cDNA clones define the complete coding region for the P210$^{c-abl}$ gene product associated with chronic myelogenous leukemia cells containing the Philadelphia chromosome, *Proc. Natl. Acad. Sci. USA 83*: 9768–9772 (1986).

Meshi, et al., "Nucleotide sequence of the 30K protein cistron of cowpea strain of tobacco mosaic virus," *Nucleic Acids Research*, 10(19): 6111–6117 (1982).

Mierendorf, et al., "Gene isolation by screening kgtll libraries with antibodies," *Methods in Enz.*, 152: 458–469 (1986).

Mikami, et al., "Primary structure and functional expression of the cardiac dihydropyridine–sensitive calcium channel," *Nature*, 340: 230–233 (1989).

Miljanich and Ramachandran, "Antagonists of neuronal calcium channels: structure, function, and therapeutic implication," *Ann. Rev. Pharm. and Toxicol.* 35:707–734 (1995).

Miller, R., "Voltage–sensitive $Ca^{2+}$ channels," *J. of Biol.Chem.*, 267(3): 1403–1406 (1992).

Miller, "Multiple calcium channels and neuronal function," *Science*, 235: 46–52 (1987).

Mori, et al., "Primary structure and functional expression from complementary DNA of a brain calcium channel," *Nature*, 350: 398–402 (1991).

Morton, et al. "Monoclonal antibody identifies a 200–kDA subunit of the dihydropyridine–sensitive calcium channel," *J.Biol.Chem.*, 262(25): 11904–11907 (1987).

Nakayama, et al., "Purification of a putative $Ca^{2+}$ channel protein from rabbit skeletal muscle," *J.Biol.Chem.*, 262: 6572–6576 (1987).

Niidome, et al., "Molecular cloning and characterization of a novel calcium channel from rabbit brain", *FEBS Lett* 308:7–13 (1992).

Nikaido, et al., "Molecular cloning of cDNA encoding human interleukin–2 receptor," *Nature*, 311: 631–636 (1984).

Noda, et al., "Existence of distinct sodium channel messenger RNAs in rat brain," *Nature*, 320: 188–192 (1986).

Nunoki, et al., "Activation of purified calcium channels by stoichiometric protein phosphorylation," *Proc.Natl.Acad. Sci. USA*, 86: 6816–6820 (1989).

Olivera, et al., "Conotoxins," *J. of Biol.Chem.*, 266(33): 22067–22070 (1991).

Peralta, et al., "Distinct primary structures, ligand–binding properties and tissue–specific expression of four human muscarinic acetylcholine receptors," *EMBO J.* 6(13):3923–3929 (1987).

Perez–Reyes, et al., "Induction of calcium currents by the expression of the $\alpha_1$–subunit of the dihydropyridine receptor from skeletal muscle," *Nature*, 340: 233–236 (1989).

Perez–Reyes, et al., "Cloning and expression of a cardiac/brain β subunit of the L–type calcium channel," *J. of Biol.Chem.*, 267(3): 1792–1797 (1992).

Perez–Reyes et al., "Molecular characterization of a neuronal low–voltage–activated T–type calcium channel", *Nature* 391:896–900 (1998).

Perez–Reyes et al., "Molecular characterisation of T–type calcium channels", Low Voltage–Act T–type Calcium Channels, Proc. Int. Electrophysiology Meeting, Oct. 21–22, 1996, Guest editors: Richard W. Tsien, Jean–Paul Clozel, Joël Nargeot.

Perez–Reyes, et al., "Molecular diversity of L–type calcium channels," *J. of Biol.Chem.*, 265(33): 20430–20436 (1990).

Perez–Reyes et al., "The use of PCR to probe calcium channel diversity", *J. of Rec Res* 11(1–4):553–576 (1991).

Piedras–Renteria, et al, "Antisense oligonucleotides against rat brain $\alpha_{1E}$ DNA and its atrial homologue decrease T–type calcium current in atrial myocytes", *Proc. Natl. Acad. Sci. USA* 94:14936–14941 (1997).

Pinto et al., "Differential effect of Lambert–Eaton myasthenic syndrom immunoglobulin on cloned neuronal voltage–gated calcium channels$^a$", *Ann. NY Acad Sci.* 841:687–690 (1998).

Pinto et al., "Human autoantibodies specific for the $\alpha_{1A}$ calcium channel subunit reduce both P–type adn Q–type calcium currents in cerebellar neurons", *Proc. Natl. Acad. Sci USA* 95:8328–8333 (1998).

Powers, et al., "Skeletal Muscle and Brain Isoforms of a β–Subunit of Human Voltage–dependent Calcium Channels Are Encoded by a Single Gene", *J. Biol. Chem.* 267:22967–22972 (1992).

Powers, et al., "Assignment of the human gene for the $\alpha_1$ subunit of the cardiac DHP–sensitive $Ca^{2+}$ channel (CCHL1A1) to Chromosome 12p12–pter," *Genomics*, 10: 835–839 (1991).

Pragnell et al, "Calcium channel β–subunit binds to a conserved motif in the I–II cytoplasmic linker of the $\alpha_1$–subunit", *Nature* 368:67–70 (1994).

Pragnell et al, "Cloning and tissue–specific expression of the brain calcium channel β–subunit", *Federation of Euro. Biochem. Soc.* 291(2):253–258 (1991).

Rampe, et al., "[$^3$H]Pn200–110 binding in a fibroblast cell line transformed with the $\alpha_1$ subunit of the skeletal muscle L–type $Ca^{2+}$ channel," *Bicohem. and Biophys.Research Communications*, 169(3): 825–831 (1990).

Randall, et al, "Contrasting biophysical and pharmacological properties of T–type and R–type calcium channels", *Neuropharmacology* 36(7):879–893 (1997).

Regulla, et al., "Identification of the site of interaction of the dihydropyridine channel blockers nitrendipine and azidopine with the calcium–channel $\alpha_1$ subunit," *EMBO Journal*, 10(1): 45–49 (1991).

Roberts, et al., "Paraneoplastic myasthenic syndrome IgG Inhibits $^{45}Ca^{2+}$ flux in a human small cell carcinoma line," *Nature*, 317: 737–739 (1985).

Rock et al., "Biophysical and pharmacological characterization of stably expressed class B and class E $Ca^{2+}$ channels in HEK 293 cells," *Soc. Neurosci. Abstr.* 21:508.1 (1995).

Rosenfield et al. , "Cloning and Characterization of a Lambert–Eaton Myasthenic Syndrome Antigen", *Annals of Neurology* 33:113–120 (1993).

Ruth, et al., "Primary structure of the β subunit of the DHP–sensitive calcium channel from skeletal muscle," *Science*, 245: 1115–1118 (1989).

Sakamoto, et al., "A monoclonal antibody to the β subunit of the skeletal muscle dihydropyridine receptor immunoprecipitates the brain w–conotoxin GVIA receptor," *J.Biol.Chem.,* 266: 18914 (1991).

Sakurai et al., "Immunochemical identification and differential phosphorylation of alternatively spliced forms of the $\alpha_{1A}$ subunit of brain calcium channels," *J. Biol. Chem.* 270(36):21234–21242 (1995).

Sambrook, et al., "Molecular cloning a laboratory manual", 2nd ed., 7.26–7.29, Chapter 8 (8.2–8.86), 9.47–9.57 and 16.3, Cold Spring Harbor Lab. Press (1989).

Sanes et al., "Use of a recombinant retrovirus to study post–implantation cell lineage in mouse embryos", *EMBO Journal* 5(12):3133–3142 (1986).

Scharf, Chapter 11: Cloning with PCR, *PCR Protocols A Guide To Methods and Applications,* Innis, M.A., et al., eds., New York: Academic Press, 1990, pp. 84–91.

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry,* 25: 3492–3495 (1986).

Seagar, et al., "Molecular properties of dehydropyrine–sensitive calcium channels," *Ann.N.Y.Acad.Sci.,* 552: 162–175 (1988).

Seino, et al., "Cloning of $\alpha_1$ subunit of a voltage–dependent calcium channel expressed in pancreatic β cells," *Proc.Natl.Acad.Sci. USA,* 89: 584–588 (1992).

Sharp and Campbell, "Characterization of the 1,4–dihydropyridine receptor using subunit–specific polyclonal antibodies," *J.Biol.Chem.,* 264(5): 2816–2825 (1989).

Sharp, et al., "Identification and characterization of the dihydropyridine–binding subunit of the skeletal muscle dihydropyridine receptor," *J.Biol.Chem.,* 62(25): 12309–12315 (1987).

Sher, et al., "w–Conotoxin binding and effects on calcium channel function in human neuroblastoma and rat pheochromocytoma cell lines," *FEBS Letters,* 235: (1,2): 178–182 (1988).

Sher, et al., "Voltage–operated calcium channels in small cell lung carcinoma cell lines: pharmacological, functional, and immunological properties," *Cancer Research,* 5: 3892–3896 (1990).

Sieber, et al., "The 165–kDa peptide of the purified skeletal muscle dihydropyridine receptor contains the known regulatory sites of the calcium channel," *Eur.J.Biochem.,* 167: 117–122 (1987).

Simerson et al., "Pharmacological characterization of recombinant cell lines stably expressing human voltage–gated calcium channel subunits $\alpha_{1A}$, $\alpha_{1B}$ and $\alpha_{1E}$," *Soc. Neurosci. Abstr.* 21 (1995).

Slish, et al., "Evidence for the existence of a cardiac specific isoform of the $\alpha_1$–subunit of the voltage dependent calcium channel," *FEBS Letters,* 250(2): 509–514 (1989).

Smith, et al., "Calcium channel activity in a purified dihydropyridine–receptor preparation of skeletal muscle," *Biochemistry,* 26: 7182–7188 (1987).

Snutch, et al., "Distinct calcium channels are generated by alternative splicing and are differentially expressed in the mammalian CNS," *Neuron,* 7: 45–57 (1991).

Snutch, et al., "Rat brain expresses a heterogeneous family of calcium channels," *Proc.Natl.Acad.Sci. USA,* 87: 3391–3395 (1990).

Soldatov, "Molecular diversity of L–type $Ca^{2+}$ channel transcripts in human fibroblasts", *Proc.Natl.Acad.Sci.* 89:4628–4632 (1992).

Soong, et al., "Structure and functional expression of a member of the low voltage–activated calcium channel family", *Science* 260:1133–1136 (1993).

Spedding, et al., 'Calcium antgonists': A class of drugs with a bright future. Part II. Determination of Basic Pharmacological Properties, *Life Sciences* 35:575–587 (1984).

Stanley, et al., "Characterization of a calcium current in a vertebrate cholinergic presynaptic nerve terminal," *J. Neurosci.,* 11: 985 (1991).

Starr, et al., "Primary structure of a calcium channel that is highly expressed in the rat cerebellum," *Proc.Natl.Acad. Sci.,* 88: 5621–5625 (1991).

Stefani, et al., "Action of GP 47779, the active metabolite of oxcarbazepine, on the corticostriatal system. II. Modulation of high–voltage–activated calcium currents," *Epilepsia* 336(10):997–1002 (1995).

Striessnig, et al., "Photoaffinity labelling of the phenylalkylamine receptor of the skeletal muscle transverse–tubule calcium channel," *FEBS Letters,* 212(2):247–253 (1987).

Stumpo et al., "Identification of c–fos sequences involved in induction by insulin and phorbol esters," *J. Biol. Chem.* 263(4):1611–1614 (1988).

Summarized Translation (from Japanese foreign associate) of Japanese Patent 60–40955, published Mar. 4, 1985.

Summarized Translation (from Japanese foreign associate) of Japanese Patent 2–59647, published Feb. 28, 1990.

Summarized Translation (from Japanese foreign associate) of Japanese Patent 3–85455, published Apr. 10, 1991.

Swandulla, et al., "Do calcium channel classifications account for neuronal calcium channel diversity?" *TINS,* 14(2): 46–51 (1991).

Takahashi, et al., "Identification of an α subunit of dihydropyridine–sensitive brain calcium channels," *Science,* 236: 88–91 (1987).

Takahashi, et al., "Subunit structure of dihydropyridine–sensitive calcium channels from skeletal muscle," *Proc.Natl.Acad.Sci. (USA),* 84: 5478–5482 (1987).

Takahashi, et al., Dihydropyridine–sensitive calcium channels in cardiac and skeletal muscle membranes: studies with antibodies against the alpha subunits, *Biochemistry* 26:5518–5526 (1987).

Tanabe, et al., "Cardiac–type excitation–contraction coupling in dysgenic skeletal muscle injected with cardiac dihydropyridine receptor cDNA," *Nature,* 344: 451–453 (1990).

Tanabe, et al., "Regions of the skeletal muscle dihydropyridine receptor critical for excitation–contraction coupling," *Nature,* 346: 567–569 (1991).

Tsien, et al., "Molecular diversity of voltage–dependent $Ca^{2+}$ channels," *Trends in Pharmacol.Sci.,* 12: 349 (1991).

Utz et al., "Inhibition of L–type calcium currents in guinea pig ventricular myocytes by the κ–opioid agonist U50488H does not involve binding to opiate receptors," *J. Pharm. Exp. Thera.* 274(2):627–633 (1995).

Vaghy, et al., "Identification of a novel 1,4–dihydropyridine– and phenylalkylamine–binding polypeptide in calcium channel preparations," *J.Biol.Chem.,* 262(29): 14337–14342 (1987).

Vaghy, et al., "Mechanism of action of calcium channel modulator drugs," *Ann.N.Y.Acad.Sci.,* 522: 176–186 (1988).

Varadi, et al., "Developmental regulation of expression of the $\alpha_1$ and $\alpha_2$ subunits mRNAs of the voltage–dependent calcium channel in a differentiating myogenic cell line," *FEBS Letters,* 250(2)CE: 515–518 (1989).

Varaldi et al., Acceleration of activation and inactivation by the β subunit of the skeletal muscle calcium channel, Nature 352: 159–162 (1991).

von Heijne, "Signal sequences: the limits of variation," *Jour. of Mol.Biol.,* 184: 99–105 (1985).

Washburn, "Electrophysiological and pharmacological properties of $\alpha^{1H}$ mediated low–voltage activated calcium currents recorded in Xenopus oocytes", SIBIA Neurosciences, Inc. 1998 Annual Meeting, Los Angeles, California Nov. 7–12, 1998.

Wei, et al., "Heterologous regulation of the cardiac $Ca^{2+}$ channel $\alpha_1$ subunit by skeletal muscle β and γ subunits," *J.Biol.Chem.,* 266: 21943–21947 (1991).

Westenbroek et al., "Immunochemical identification and subcellular distribution of the $\alpha_{1A}$ subunits of brain calcium channels," *J. Neurosci.* 15(10):6403–6418 (1995).

White et al, "Transient low–threshold $Ca^{2+}$ current triggers burst firing through an afterdepolarizing potential in an adult mammalian neuron", *Proc. Natl. Acad. Sci. USA* 86:6802–6806 (1989).

Williams, "Cloning and characterization of a novel human $Ca_{2+}$ channel $\alpha^1$ subunit associated with a low–voltage activated (LVA) $Ca_{2+}$", SIBIA Neurosciences, Inc. 1998 Annual Meeting, Los Angeles, California Nov. 7–12, 1998.

Williams et al., "Structure and Functional Expression of an ω–Conotoxin–Sensitive Human N–Type Calcium Channel", *Science* 257:389–395 (1992).

Williams, et al., "Structure and functional expression of $\alpha_1$, $\alpha_2$ and β subunits of a novel human neuronal calcium channel subtype," *Neuron,* 8:71–84 (1992).

Williams et al., "An essential structural domain that determines the biophysical properties of the human $\alpha_{1A}$ high–voltage activated calcium channel," *Soc. Neurosci. Abstr.* 21:508.3 (1995).

Wood, "Gene cloning based on long oligonucleotide probes," *Methods in Enzymology,* 152: 443–447 (1987).

Yokoyama et al., "Biochemical properties and subcellular distribution of the neuronal class E calcium channel $\alpha_1$ subunit," *J. Neurosci.* 15(10):6419–6432 (1995).

Yu et al., "Molecular characterization and nephron distribution of a family of transcripts encoding the pore–forming subunit of $Ca^{2+}$ channels in the kidney", *Proc.Natl.Acad.Sci.* 89:10494–10498 (1992).

Dzhura et al, "Characterization of Hypothalamic Low–Voltage–Activated Ca Channels Based On Their Functional Expression in Xenopus Oocytes," *Neuroscience* 70(3):729–738 (1996).

Harpold et al, "Human Neuronal Voltage–Gated Calcium Channels: Splice Variants, Subunit Interactions and Subtypes," in; *Low Voltage Activated T–type Calcium Channels,* Proceedings of the International Electrophysiology Meeting, Clozel, Nargeot, and Tsien eds, (1996).

Nooney et al, "Identifying neuronal non–L $Ca^{2+}$ channels—more than stamp collecting?", *TiPS* 18:363–371 (1997).

Williams et al, "Structure and Functional Characterization of a Novel Human Low–Voltage Activated Calcium Channel," *J. Neurochemistry* 72(2):791–799 (1999).

Williams, "Cloning and characterization of a novel human $Ca^{2+}$ channel $\alpha_1$ subunit associated with a low–voltage activated (LVA) $Ca^{2+}$", SIBIA Neurosciences, Inc. 1998 Annual Meeting, Los Angeles, California Nov. 7–12, 1998.

Davis et al. Basic Methods in Molecular Biology, Elsevier Science Publishing Co., New York (1986).

Gorman et al., *Nucleic Acids Res. 11*:1631 (1983).

\* cited by examiner

CALCIUM CHANNEL COMPOSITIONS AND METHODS

RELATED APPLICATIONS

This application is related to U.S. application Ser. No. 08/450,272, filed May 25, 1995, U.S. application Ser. No. 08/450,273, filed May 25, 1995, U.S. application Ser. No. 08/450,562, filed May 25, 1995. Each of these applications is a continuation-in-part of U.S. application Ser. No. 08/290,012. This application is also related to International PCT application No. PCT/US94/09230, filed Aug. 11, 1994, which claims priority to U.S. application Ser. Nos. 08/105,536 and 08/149,097.

This application is also related to U.S. application Ser. No. 08/404,354, filed Feb. 15, 1995, now U.S. Pat. No. 5,618,720, which is a continuation of U.S. application Ser. No. 07/914,231, filed Jul. 13, 1992, now U.S. Pat. No. 5,407,820, and also U.S. application Ser. No. 08/314,083, filed Sep. 28, 1994, now U.S. Pat. No. 5,686,241, which is a divisional of U.S. application Ser. No. 07/914,231. U.S. application Ser. No. 07/914,231 is a continuation of U.S. application Ser. No. 07/603,751, filed Nov. 8, 1990, now abandoned, which is the national stage of International PCT Application PCT/US89/01408, filed Apr. 4, 1989, which is a continuation-in-part of U.S. application Ser. No. 07/176,899, filed Apr. 4, 1988, now abandoned.

This application is also related to U.S. application Ser. No. 08/884,599, filed Jun. 27, 1997, which is a continuation of U.S. application Ser. No. 08/314,083.

This application is also related to U.S. application Ser. No. 08/290,012, filed Aug. 11, 1994, now abandoned, which is a continuation-in-part of allowed U.S. application Ser. No. 08/149,097, filed Nov. 5, 1993, and a continuation-in-part of U.S. application Ser. No. 08/105,536, filed Aug. 11, 1993. U.S. application Ser. No. 08/149,097 is a continuation-in-part of U.S. application Ser. No. 08/105,536, which is a continuation-in-part of the above-mentioned U.S. application Ser. No. 07/603,751, filed Nov. 8, 1990. 08/336,257

This application is also a related to allowed U.S. application Ser. No. 08/223,305, filed Apr. 4, 1994, which is a continuation of U.S. application Ser. No. 07/868,354, now abandoned, which is a continuation-in-part of U.S. application Ser. No. 07/745,206, filed Aug. 15, 1991, now U.S. Pat. No. 5,429,921, which is a continuation-in-part of the above-mentioned U.S. application Ser. No. 07/603,751, filed Nov. 8, 1990, and a continuation-in-part of U.S. application Ser. No. 07/620,250, filed Nov. 30, 1990, now abandoned. This application is also related to allowed application U.S. application Ser. No. 08/455,543, filed May 31, 1995, which is a continuation of U.S. application Ser. No. 07/868,354, filed Apr. 10, 1992.

This application is also a related to U.S. application Ser. No. 08/311,363, filed Sep. 23, 1994, which is a continuation of allowed U.S. application Ser. No. 07/745,206, filed Aug. 15, 1991.

This application is also related to allowed U.S. application Ser. No. 08/193,078, filed Feb. 7, 1994, which is the National Stage of International PCT Application No. PCT/US92/06903, filed Aug. 14, 1992 and which is a continuation-in-part of U.S. application Ser. Nos. 07/868,354, 07/745,206, 07/603,751, 07/176,899, 07/620,250, filed Nov. 30, 1990, now abandoned, and 07/482,384, now U.S. Pat. No. 5,386,025, filed Feb. 2, 1990.

This application is also related to allowed U.S. application Ser. No. 08/336,257, filed Nov. 7, 1994, which is a continuation of 07/482,384, now U.S. Pat. No. 5,386,025, filed Feb. 2, 1990.

The subject matter of each of the above-noted U.S. applications, patents and International PCT applications is incorporated herein in its entirety.

TECHNICAL FIELD

The present invention relates to molecular biology and pharmacology. More particularly, the invention relates to calcium channel compositions and methods of making and using the same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. All "excitable" cells in animals, such as neurons of the central nervous system (CNS), peripheral nerve cells and muscle cells, including those of skeletal muscles, cardiac muscles, and venous and arterial smooth muscles, have voltage-dependent calcium channels. "Opening" of a voltage-dependent channel to allow an influx of $Ca^{2+}$ ions into the cells requires a depolarization to a certain level of the potential difference between the inside of the cell bearing the channel and the extracellular environment bathing the cell. The rate of influx of $Ca^{2+}$ into the cell depends on this potential difference.

Multiple types of calcium channels have been identified in mammalian cells from various tissues, including skeletal muscle, cardiac muscle, lung, smooth muscle and brain, [see, e.g., Bean, B. P. (1989) *Ann. Rev. Physiol.* 51:367–384 and Hess, P. (1990) *Ann. Rev. Neurosci.* 56:337]. The different types of calcium channels have been broadly categorized into four classes, L-, T-, N-, and P-type, distinguished by current kinetics, holding potential sensitivity and sensitivity to calcium channel agonists and antagonists.

Calcium channels are multisubunit proteins that contain two large subunits, designated $\alpha_1$ and $\alpha_2$, which have molecular weights between about 130 and about 200 kilodaltons ("kD"), and one to three different smaller subunits of less than about 60 kD in molecular weight. At least one of the larger subunits and possibly some of the smaller subunits are glycosylated. Some of the subunits are capable of being phosphorylated. The $\alpha_1$ subunit has a molecular weight of about 150 to about 170 kD when analyzed by sodium dodecylsulfate (SDS)-polyacrylamide gel electrophoresis (PAGE) after isolation from mammalian muscle tissue and has specific binding sites for various 1,4-dihydropyridines (DHPs) and phenylalkylamines. Under non-reducing conditions (in the presence of N-ethylmaleimide), the $\alpha_2$ subunit migrates in SDS-PAGE as a band corresponding to a molecular weight of about 160–190 kD. Upon reduction, a large fragment and smaller fragments are released. The β subunit of the rabbit skeletal muscle calcium channel is a phosphorylated protein that has a molecular weight of 52–65 kD as determined by SDS-PAGE analysis. This subunit is insensitive to reducing conditions. The γ subunit of the calcium channel appears to be a glycoprotein with an apparent molecular weight of 30–33 kD, as determined by SDS-PAGE analysis.

In order to study calcium channel structure and function, large amounts of pure channel protein are needed. Because of the complex nature of these multisubunit proteins, the varying concentrations of calcium channels in tissue sources of the protein, the presence of mixed populations of calcium channels in tissues, difficulties in obtaining tissues of interest, and the modifications of the native protein that can occur during the isolation procedure, it is extremely difficult to obtain large amounts of highly purified, completely intact calcium channel protein.

Characterization of a particular type of calcium channel by analysis of whole cells is severely restricted by the presence of mixed populations of different types of calcium channels in the majority of cells. Single-channel recording methods that are used to examine individual calcium channels do not reveal any information regarding the molecular structure or biochemical composition of the channel. Furthermore, in performing this type of analysis, the channel is isolated from other cellular constituents that might be important for natural functions and pharmacological interactions.

Characterization of the gene or genes encoding calcium channels provides another means of characterization of different types of calcium channels. The amino acid sequence determined from a complete nucleotide sequence of the coding region of a gene encoding a calcium channel protein represents the primary structure of the protein. Furthermore, secondary structure of the calcium channel protein and the relationship of the protein to the membrane may be predicted based on analysis of the primary structure. For instance, hydropathy plots of the a, subunit protein of the rabbit skeletal muscle calcium channel indicate that it contains four internal repeats, each containing six putative transmembrane regions [Tanabe, T. et al. (1987) *Nature* 328:313].

Because calcium channels are present in various tissues and have a central role in regulating intracellular calcium ion concentrations, they are implicated in a number of vital processes in animals, including neurotransmitter release, muscle contraction, pacemaker activity, and secretion of hormones and other substances. These processes appear to be involved in numerous human disorders, such as CNS and cardiovascular diseases. Calcium channels, thus, are also implicated in numerous disorders. A number of compounds useful for treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

The results of studies of recombinant expression of rabbit calcium channel $\alpha_1$ subunit-encoding cDNA clones and transcripts of the cDNA clones indicate that the $\alpha_1$, subunit forms the pore through which calcium enters cells. The relevance of the barium currents generated in these recombinant cells to the actual current generated by calcium channels containing as one component the respective $\alpha_1$ subunits in vivo is unclear. In order to completely and accurately characterize and evaluate different calcium channel types, however, it is essential to examine the functional properties of recombinant channels containing all of the subunits as found in vivo.

In order to conduct this examination and to fully understand calcium channel structure and function, it is critical to identify and characterize as many calcium channel subunits as possible. Also in order to prepare recombinant cells for use in identifying compounds that interact with calcium channels, it is necessary to be able to produce cells that express uniform populations of calcium channels containing defined subunits.

An understanding of the pharmacology of compounds that interact with calcium channels in other organ systems, such as the CNS, may aid in the rational design of compounds that specifically interact with subtypes of human calcium channels to have desired therapeutic effects, such as in the treatment of neurodegenerative and cardiovascular disorders. Such understanding and the ability to rationally design therapeutically effective compounds, however, have been hampered by an inability to independently determine the types of human calcium channels and the molecular nature of individual subtypes, particularly in the CNS, and by the unavailability of pure preparations of specific channel subtypes to use for evaluation of the specificity of calcium channel-effecting compounds. Thus, identification of DNA encoding human calcium channel subunits and the use of such DNA for expression of calcium channel subunits and functional calcium channels would aid in screening and designing therapeutically effective compounds.

DNA encoding human $\alpha_1$-subunits, including $\alpha_{1A}$-, $\alpha_{1B}$-, $\alpha_{1C}$-, $\alpha_{1D}$- and $\alpha_{1E}$ subunits and splice variants thereof has been described (see, e.g., U.S. Pat. No. 5,429,921, published International PCT application No. PCT/US92/06903, International PCT application No. PCT/US94/09230). These subunits appear to participate in formation of high voltage calcium (HVA) channels, which in addition to one of these $\alpha_1$-subunits, includes β subunit and an $\alpha_2$-subunit, including δ, which is linked to $\alpha_2$ by a disulfide bridge and arises from the same precursor. The distinct biophysical and pharmacological properties of each channel derive primarily form the $\alpha_1$-subunit, but are modulated by the ancillary subunits, principally the β subunits associated with the channel. β-subunits have been shown to increase the peak current amplitude, to shift activation/inactivation curves toward more hyperpolarized potentials and to alter kinetics of activation and inactivation (see, e.g., Lambert et al. (1997) *J. Neurosci.* 17:6621–6625). The $\alpha_2\delta$ subunit, which is tissue-specific, increases the current generated by any $\alpha_1$ subunit and potentiates the stimulatory response of β subunits.

T-type or LVA Channels

Little is known about the channels that have been designated T-channels or LVA (low voltage activated) channels. In general it is believed that T-type currents do not differ fundamentally from other $Ca^{2+}$ currents. Like HVA channels, T-type channels are selectively permeable to divalent cations, as long as a minimal concentration of divalent cations is present in the external medium. For LVA (or T-type) currents, this minimal $Ca^{2+}$ concentration is about 25 μm, and for HVA currents it is about 1 μM. T-type current is reported to saturate with a $K_d$ of about 10 mM $Ca^{2+}$, which is similar to that reported for HVA currents. The channels, however, appear to exhibit certain differences. They differ in their relative permeability to divalent cations. In general, HVA channels are more permeable to $Ba^{2+}$ than to $Ca^{2+}$; T-type are equally or slightly less permeable to $Ba^{2+}$ than to $Ca^{2+}$. T-type channels also are believed to exhibit slower activation/inactivation and deactivation kinetics and have been reported to exhibit relatively higher sensitivity to $Ni^{2+}$. This type of channel is activated near the resting potential of the membrane, and is believed to be responsible for the generation of repetitive firing activity or intrinsic neuronal oscillations and for $Ca^{2+}$ entry accompanying the spike activity (see, e., Huguenard (1996) *Annual Rev. Physiol.* 58:329–348). Recent data suggests that, β-subunits identified to date may not be a constitutive T-type channel subunit (see, Lambert et al. (1997) *J. Neurosci.* 17:6621–6625). The structure of calcium channels that generate the various LVA currents is unknown. None of the $\alpha_1$ subunits previously cloned appear to have all properties that have been ascribed to the low voltage-activated T-type (or LVA) channels.

Therefore, it is an object herein, to provide nucleic acid encoding specific calcium channel subunits that have structural and functional properties that differ from the HVA type channels. It is also an object herein to provide nucleic acid encoding channels that have activities that have been ascribed to T-type channels and to provide eukaryotic cells bearing recombinant tissue-specific or subtype-specific calcium channels. It is also an object to provide assays for identification of potentially therapeutic compounds that act as modulators of calcium channel activity, particularly those specific for channels that exhibit properties of human T-type channels and other types of channels.

SUMMARY OF THE INVENTION

Isolated and purified nucleic acid fragments that encode calcium channel subunits are provided. DNA encoding $\alpha_1$ subunits of a human calcium channel, and RNA, encoding such subunits, made upon transcription of such DNA are provided. In particular, nucleic acid molecules encoding $\alpha_1$ subunits of voltage-dependent human calcium channels (VDCCs) type A, type B, type C, type D, type E and type T are provided. Also provided is nucleic acid that encodes an $\alpha_{1F}$-subunit of a calcium channel, parituclarly an animal calcium channel and more particularly a mammalian calcium channel.

Nucleic acid encoding $\alpha_{1A}$, $\alpha_{1B}$, $\alpha_{1C}$, $\alpha_{1D}$, $\alpha_{1E}$ and $\alpha_{1F}$ subunits is provided. Of particular interest herein is the nucleic acid that encodes the $\alpha_{1F}$ subunits of calcium channels, particularly mammalian calcium channels. Nucleic acid encoding an exemplary $\alpha_{1F}$ subunit is set forth in SEQ ID No. 49. This nucleic acid can be used to isolate minor variants, including splice variants of the nucleic acid encoding $\alpha_{1F}$ subunits and allelic variants. Such nucleic acid includes DNA encoding an $\alpha_{1F}$ subunit that has substantially the same sequence of amino acids as encoded by the DNA set forth in SEQ ID No. 49. This nucleic acid can also be used to isolate DNA encoding $\alpha_{1F}$ subunits from other species, particularly other mammals. Also included are any subunits that are encoded by nucleic acid comprising nucleotides nt 1506 to nt 2627 of SEQ ID No. 49 or subunits that are encoded by nucleic acid that hybridizes to a probe derived from this region.

The $\alpha_{1F}$ subunit differs from the $\alpha_{1A}$–$\alpha_{1E}$ calcium channel subunits in a number of aspects. First, the intracellular loop positioned between transmembrane Domains I and II is considerably longer than HVA calcium channels. For instance, as exemplified in SEQ ID No. 49 and described below, the intracellular loop between Domains I and II is greater than 1,100 nt (1122 nt), whereas the corresponding region in HVA calcium channels ranges from 351 to 381 nt in length. Thus, the intracellular loop of $\alpha_{1F}$ contains approximately 370 additional amino acid residues (aa 420 to aa 794 of SEQ ID No. 50) not found in HVA calcium channel $\alpha_1$ subunits. In addition, the encoded amino acid sequence of this loop region is highly proline rich and contains a poly-HIS region of 9 consecutive histidine residues.

Other distinguishing features of the $\alpha_{1F}$ subunit, include the absence of amino acid residues in the intracellular loop between transmembrane Domains I and II that are known to be critical (e.g., see De Waard et al. (1996) *FEBS Letters* 380:272–276; Pragnell et al. (1994) *Nature* 368:67–70) for the interaction between an $\alpha_1$ subunit and a $\beta$ subunit. The $\alpha_{1F}$ subunit also contains a notably large extracellular loop in Domain I between ISS and IS6. The HVA $\alpha_1$ calcium channel subunits provided herein contain 249–270 nucleotide residues in this loop. In contrast, the human $\alpha_{1F}$ subunit contains 426 nucleotide residues in this loop. The intracellular loop between transmembrane Domains III and IV is also slightly larger than the HVA $\alpha_1$ subunits (186 nt compared to 159–165 nt).

Nucleic acid encoding an $\alpha_{1D}$ subunit that includes the amino acids substantially as set forth as residues 10–2161 of SEQ ID No. 1 is also provided. DNA encoding an $\alpha_{1D}$ subunit that includes substantially the amino acids set forth as amino acids 1–34 in SEQ ID No. 2 in place of amino acids 373–406 of SEQ ID No. 1 is also provided. DNA encoding an $\alpha_{1C}$ subunit that includes the amino acids substantially as set forth in SEQ ID No. 3 or SEQ ID No. 6 and DNA encoding an $\alpha_{1B}$ subunit that includes an amino acid sequence substantially as set forth in SEQ ID No. 7 or in SEQ ID No. 8 is also provided.

Nucleic acid encoding $\alpha_{1A}$ subunits is also provided. Such DNA includes DNA encoding an $\alpha_{1A}$ subunit that has substantially the same sequence of amino acids as encoded by the DNA set forth in SEQ ID No. 22 or No. 23 or other splice variants of $\alpha_{1A}$ that include all or part of the sequence set forth in SEQ ID No. 22 or 23. The sequence set forth in SEQ ID NO. 22 is a splice variant designated $\alpha_{1A\text{-}1}$; and the sequence set forth in SEQ ID NO. 23 is a splice variant designated $\alpha_{1A\text{-}2}$. DNA encoding $\alpha_{1A}$ subunits also include DNA encoding subunits that can be isolated using all or a portion of the DNA having SEQ ID NO. 21, 22 or 23 or DNA obtained from the phage lysate of an *E. coli* host containing DNA encoding an $\alpha_{1A}$ subunit that has been deposited in the American Type Culture Collection, 12301 Parklawn Drive, Rockville, Md. 20852 U.S.A. under Accession No. 75293 in accord with the Budapest Treaty. The DNA in such phage includes a DNA fragment having the sequence set forth in SEQ ID No. 21. This fragment selectively hybridizes under conditions of high stringency to DNA encoding $\alpha_{1A}$ but not to DNA encoding $\alpha_{1B}$ and, thus, can be used to isolate DNA that encodes $\alpha_{1A}$ subunits.

Nucleic acid encoding $\alpha_{1E}$ subunits of a human calcium channel is also provided. This DNA includes DNA that encodes an $\alpha_{1E}$ splice variant designated $\alpha_{1E\text{-}1}$ encoded by the DNA set forth in SEQ ID No. 24, and a variant designated $\alpha_{1E\text{-}3}$ encoded by SEQ ID No. 25. This DNA also includes other splice variants thereof that encodes sequences of amino acids encoded by all or a portion of the sequences of nucleotides set forth in SEQ ID Nos. 24 and 25 and DNA that hybridizes under conditions of high stringency to the DNA of SEQ ID. No. 24 or 25 and that encodes an $\alpha_{1E}$ splice variant.

DNA encoding $\alpha_{2B}$ subunits of a human calcium channel, and RNA encoding such subunits, made upon transcription of such a DNA are provided. DNA encoding splice variants of the $\alpha_2$ subunit, including tissue-specific splice variants, are also provided. In particular, DNA encoding the $\alpha_{2a}$–$\alpha_{2e}$ subunit subtypes is provided. In particularly preferred embodiments, the DNA encoding the $\alpha_2$ subunit that is produced by alternative processing of a primary transcript that includes DNA encoding the amino acids set forth in SEQ ID 11 and the DNA of SEQ ID No. 13 inserted between nucleotides 1624 and 1625 of SEQ ID No. 11 is provided. The DNA and amino acid sequences of $\alpha_{2a}$–$\alpha_{2e}$ are set forth in SEQ ID Nos. 11 ($\alpha_{2b}$), 29 ($\alpha_{2a}$) and 30–32 ($\alpha_{2c}$–$\alpha_{2e}$, respectively), respectively. RNA encoding these subunits is also provided.

Isolated and purified DNA fragments encoding human calcium channel $\beta$ subunits, including DNA encoding $\beta_1$, $\beta_2$, $\beta_3$ and $\beta_4$ subunits, and splice variants of the $\beta$ subunits are provided. RNA encoding $\beta$ subunits, made upon transcription of the DNA is also provided.

DNA encoding a $\beta_1$ subunit that is produced by alternative processing of a primary transcript that includes DNA encoding the amino acids set forth in SEQ ID No. 9, but including the DNA set forth in SEQ ID No. 12 inserted in place of nucleotides 615–781 of SEQ ID No. 9 is also provided. DNA encoding $\beta_1$ subunits that are encoded by transcripts that have the sequence set forth in SEQ ID No. 9 including the DNA set forth in SEQ ID No. 12 inserted in place of nucleotides 615–781 of SEQ ID No. 9, but that lack one or more of the following sequences of nucleotides: nucleotides 14–34 of SEQ ID No. 12, nucleotides 13–34 of SEQ ID No. 12, nucleotides 35–55 of SEQ ID No. 12, nucleotides 56–190 of SEQ ID No. 12 and nucleotides 191–271 of SEQ ID No. 12 are also provided. In particular, $\beta_1$ subunit splice variants $\beta_{1-1}$–$\beta_{1-5}$ (see, SEQ ID Nos. 9, 10 and 33–35) described below, are provided.

$\beta_2$ subunit splice variants $\beta_{2c}$–$\beta_{2e}$, that include all or a portion of SEQ ID Nos. 26, 37 and 38 are provided; $\beta_3$ subunit splice variants, including $\beta_3$ subunit splice variants that have the sequences set forth in SEQ ID Nos 19 and 20, and DNA encoding the $\beta_4$ subunit that includes DNA having the sequence set forth in SEQ ID No. 27 and the amino acid sequence set forth in SEQ ID No. 28 are provided.

Also *Escherichia coli* (*E. coil*) host cells harboring plasmids containing DNA encoding $\beta_3$ have been deposited in accord with the Budapest Treaty under Accession No. 69048 at the American Type Culture Collection. The deposited clone encompasses nucleotides 122–457 in SEQ ID No. 19 and 112–447 in SEQ ID No. 20.

DNA encoding $\beta$ subunits that are produced by alternative processing of a primary transcript encoding a $\beta$ subunit, including a transcript that includes DNA encoding the amino acids set forth in SEQ ID No. 9 or including a primary transcript that encodes $\beta_3$ as deposited under ATCC Accession No. 69048, but lacking and including alternative exons are provided or may be constructed from the DNA provided herein.

DNA encoding $\gamma$ subunits of human calcium channels is also provided. RNA, encoding $\gamma$ subunits, made upon transcription of the DNA are also provided. In particular, DNA containing the sequence of nucleotides set forth in SEQ ID No. 14 is provided.

Full-length DNA clones and corresponding RNA transcripts, encoding $\alpha_1$, including splice variants of $\alpha_{1A}$, $\alpha_{1B}$, $\alpha_{1C}$, $\alpha_{1D}$, and $\alpha_{1E}$, $\alpha_2$ and $\beta$ subunits, including $\beta_{1-1}$–$\beta_{1-5}$, $\beta_{2C}$, $\beta_{2D}$, $\beta_{2E}$, $\beta_{3-1}$ and $\beta_4$ of human calcium channels are provided. Also provided are DNA clones encoding substantial portions of the certain $\alpha_{1C}$ subtype subunits and $\gamma$ subunits of voltage-dependent human calcium channels for the preparation of full-length DNA clones encoding the corresponding full-length subunits. Full-length clones may be readily obtained using the disclosed DNA as a probe as described herein.

The $\alpha_{1F}$ subunit and splice variants thereof and nucleic acids encoding these subunits are of particular interest herein.

Eukaryotic cells containing heterologous DNA encoding one or more calcium channel subunits, particularly human calcium channel subunits, or containing RNA transcripts of DNA clones encoding one or more of the subunits are provided. A single $\alpha_1$ subunit can form a channel. The requisite combination of subunits for formation of active channels in selected cells, however, can be determined empirically using the methods herein. For example, if a selected $\alpha_1$ subtype or variant does not form an active channel in a selected cell line, an additional subunit or subunits can be added until an active channel is formed.

In preferred embodiments, the cells contain DNA or RNA encoding an $\alpha_1$ subunit, preferably an $\alpha_{1F}$ subunit of an animal, preferably of a mammalian calcium channel. Embodiments in which the cells contain nucleic acid encoding an $\alpha_{1F}$ are of particular interest herein. In more preferred embodiments, the cells contain DNA or RNA encoding additional heterologous subunits, including an $\alpha_2\delta$. The cells may also include nucleic acid encoding a $\beta$ subunit and/or a $\gamma$ subunit. In such embodiments, eukaryotic cells stably or transiently transfected with any combination of one, two, three or four of the subunit-encoding DNA clones, such as DNA encoding any of $\alpha_1$, $\alpha_1+\beta$, $\alpha_1+\beta+\alpha_2$, are provided. The eukaryotic cells provided herein contain heterologous nucleic acid that encodes an $\alpha_1$ subunit and optionally a heterologous $\alpha_2$-subunit and/or a $\beta$ subunit and/or $\gamma$ subunit.

In preferred embodiments, the cells express such heterologous calcium channel subunits and include one or more of the subunits in membrane-spanning heterologous calcium channels. In more preferred embodiments, the eukaryotic cells express functional, heterologous calcium channels that are capable of gating the passage of calcium channel-selective ions and/or binding compounds that, at physiological concentrations, modulate the activity of the heterologous calcium channel. In certain embodiments, the heterologous calcium channels include at least one heterologous calcium channel subunit. In most preferred embodiments, the calcium channels that are expressed on the surface of the eukaryotic cells are composed substantially or entirely of subunits encoded by the heterologous DNA or RNA. In preferred embodiments, the heterologous calcium channels of such cells are distinguishable from any endogenous calcium channels of the host cell. Such cells provide a means to obtain homogeneous populations of calcium channels. Typically, the cells contain the selected calcium channel as the only heterologous ion channel expressed by the cell.

In certain embodiments the recombinant eukaryotic cells that contain the heterologous DNA encoding the calcium channel subunits are produced by transfection with DNA encoding one or more of the subunits or are injected with RNA transcripts of DNA encoding one or more of the calcium channel subunits. The DNA may be introduced as a linear DNA fragment or may be included in an expression vector for stable or transient expression of the subunit-encoding DNA. Vectors containing DNA encoding human calcium channel subunits are also provided.

The eukaryotic cells that express heterologous calcium channels may be used in assays for calcium channel function or, in the case of cells transformed with fewer subunit-encoding nucleic acids than necessary to constitute a functional recombinant human calcium channel, such cells may be used to assess the effects of additional subunits on calcium channel activity. The additional subunits can be provided by subsequently transfecting such a cell with one or more DNA clones or RNA transcripts encoding human calcium channel subunits.

The recombinant eukaryotic cells that express membrane spanning heterologous calcium channels may be used in methods for identifying compounds that modulate calcium channel activity. In particular, the cells are used in assays that identify agonists and antagonists of calcium channel activity in humans and/or assessing the contribution of the various calcium channel subunits to the transport and regulation of transport of calcium ions. Because the cells constitute homogeneous populations of calcium channels, they provide a means to identify agonists or antagonists of calcium channel activity that are specific for each such population.

The assays that use the eukaryotic cells for identifying compounds that modulate calcium channel activity are also provided. In practicing these assays the eukaryotic cell that expresses a heterologous calcium channel, containing at least one subunit encoded by the DNA provided herein, is in a solution containing a test compound and a calcium channel selective ion, the cell membrane is depolarized, and current flowing into the cell is detected. If the test compound is one that modulates calcium channel activity, the current that is detected is different from that produced by depolarizing the same or a substantially identical cell in the presence of the same calcium channel-selective ion but in the absence of the compound. In preferred embodiments, prior to the depolarization step, the cell is maintained at a holding potential which substantially inactivates calcium channels which are endogenous to the cell. Also in preferred embodiments, the cells are mammalian cells, most preferably HEK cells, or amphibian oöcytes.

Transcription based assays for identifying compounds that modulate the activity of calcium channels (see, U.S. Pat. Nos. 5,436,128 and 5,401,629), particularly calcium channels that contain an $\alpha_{1F}$ subunit are provided. These assays use cells that express calcium channels, particularly calcium channels containing an $\alpha_{1F}$-subunit, and more preferably an $\alpha_{1F}$-subunit encoded by heterologous DNA, and also contain nucleic acid encoding a reporter gene construct containing a reporter gene in operative linkage with one or more transcriptional control elements that is regulated by a calcium channel. The assays are effected by comparing the difference in the amount of transcription of a the reporter gene in the cells provided herein in the presence of the compound with the amount of transcription in the absence of the compound, or with the amount of transcription in the absence of the heterologous calcium channel, whereby compounds that modulate the activity of the heterologous calcium channel in the cell are identified. The reporter gene is any such gene known to those of skill in the art, including, but not limited to the gene encoding bacterial chloramphenicol acetyltransferase, the gene encoding firefly luciferase, the gene encoding bacterial luciferase, the gene encoding β-galactosidase or the gene encoding alkaline phosphatase, and the transcriptional control element is any such element known to those of skill in the art, including, but not limited to serum responsive elements, cyclic adenosine monophosphate responsive elements, the c-fos gene promoter, the vasoactive intestinal peptide gene promoter, the somatostatin gene promoter, the proenkephalin promoter, the phosphoenolpyruvate carboxykinase gene promoter or the nerve growth factor-1 A gene promoter and elements responsive to intracellular calcium ion levels.

Nucleic acid probes can be labeled, which if needed, for detection, containing at least about 14, preferably 16, or, if desired, 20 or 30 or more, contiguous nucleotides of $\alpha_{1D}$, $\alpha_{1C}$, $\alpha_{1B}$, $\alpha_{1A}$, $\alpha_{1E}$, $\alpha_{1F}$, $\alpha_2\delta$, β, including $β_1$, $β_2$, $β_3$ and $β_4$ and γ subunit-encoding nucleic acids and splice variants are provided. Methods using the probes for the isolation and cloning of calcium channel subunit-encoding DNA, including splice variants within tissues and inter-tissue variants are also provided.

Other assays in which receptor activity in response to test compounds is measured may also be practiced with the cells provided herein (see, e.g., U.S. Pat. No. 5,670,113).

Purified human calcium channel subunits and purified human calcium channels are provided. The subunits and channels can be isolated from a eukaryotic cell transfected with DNA that encodes the subunit.

In another embodiment, immunoglobulins or antibodies obtained from the serum of an animal immunized with a substantially pure preparation of a human calcium channel, human calcium channel subunit or epitope-containing fragment of a human calcium subunit are provided. Monoclonal antibodies produced using a human calcium channel, human calcium channel subunit or epitope-containing fragment thereof as an immunogen are also provided. E. coli fusion proteins including a fragment of a human calcium channel subunit may also be used as immunogen. Such fusion proteins may contain a bacterial protein or portion thereof, such as the E. coil TrpE protein, fused to a calcium channel subunit peptide. The immunoglobulins that are produced using the calcium channel subunits or purified calcium channels as immunogens have, among other properties, the ability to specifically and preferentially bind to and/or cause the immunoprecipitation of a human calcium channel or a subunit thereof which may be present in a biological sample or a solution derived from such a biological sample. Such antibodies may also be used to selectively isolate cells that express calcium channels that contain the subunit for which the antibodies are specific.

Methods for modulating the activity of ion channels by contacting the calcium channels with an effective amount of the above-described antibodies are also provided.

DETAILED DESCRIPTION OF THE INVENTION

Definitions:

Unless defined otherwise, all technical and scientific terms used herein have the same meaning as is commonly understood by one of skill in the art to which this invention belongs. All patents and publications referred to herein are incorporated by reference herein.

Reference to each of the calcium channel subunits includes the subunits that are specifically disclosed herein and human calcium channel subunits encoded by nucleic acid that can be isolated by using the nucleic acid disclosed as probes and screening an appropriate human cDNA or genomic library under at least low stringency. Such DNA also includes DNA that encodes proteins that have about 40% homology to any of the subunits proteins described herein or DNA that hybridizes under conditions of at least low stringency to the DNA provided herein and the protein encoded by such DNA exhibits additional identifying characteristics, such as function or molecular weight. In particular, reference to an $\alpha_{1F}$ subunit refers to subunits that can be isolated from nucleic acid libraries from any desired source using the nucleic acid disclosed herein as a probe. The encoded subunit is characterized by the presence of the notably long intracellular loop between transmembrane domains I and II, and/or properties ascribed to T-type or LVA type channels.

It is understood that subunits that are encoded by transcripts that represent splice variants of the disclosed subunits or other such subunits may exhibit less than 40% overall homology to any single subunit, but will include regions of such homology to one or more such subunits. It is also understood that 40% homology refers to proteins that share approximately 40% of their amino acids in common or that share somewhat less, but include conservative amino acid substitutions, whereby the activity of the protein is not substantially altered.

The subunits and DNA fragments encoding such subunits provided herein include any $\alpha_1$, $\alpha_2$, $\beta$ or $\gamma$ subunits of a human calcium channel. In particular, such DNA fragments include any isolated DNA fragment that (encodes a subunit of a human calcium channel, that (1) contains a sequence of nucleotides that encodes the subunit, and (2) is selected from among:

(a) a sequence of nucleotides that encodes a human calcium channel subunit and includes a sequence of nucleotides set forth in any of the SEQ ID's herein (i.e., SEQ ID Nos. 1–52) that encodes such subunit;

(b) a sequence of nucleotides that encodes the subunit and hybridizes under conditions of high stringency to DNA that is complementary to an mRNA transcript present in a human cell that encodes a subunit that includes the sequence of nucleotides set forth in any of SEQ ID No. 1–52;

(c) a sequence of nucleotides that encodes the subunit that includes a sequence of amino acids encoded by any of SEQ ID Nos. 1–52; and (d) a sequence of nucleotides that encodes a subunit that includes a sequence of amino acids encoded by a sequence of nucleotides that encodes such subunit and hybridizes under conditions of high stringency to DNA that is complementary to an mRNA transcript present in a human cell that encodes the subunit that includes the sequence of nucleotides set forth in any of SEQ ID Nos. 1–52.

As used herein, the $\alpha_1$ subunit types, encoded by different genes, are designated as type $\alpha_{1A}$, $\alpha_{1B}$, $\alpha_{1C}$, $\alpha_{1D}$, $\alpha_{1E}$ and $\alpha_{1F}$. These types have also been referred to as VDCC IV for $\alpha_{1B}$, VDCC II for $\alpha_{1C}$ and VDCC III for $\alpha_{1D}$. Subunit subtypes, which are splice variants, are referred to, for example as $\alpha_{1B-1}$, $\alpha_{1B-2}$, $\alpha_{1C-1}$ etc.

Thus, as used herein, DNA encoding the $\alpha_1$ subunit refers to DNA that hybridizes to the DNA provided herein under conditions of at least low stringency or encodes a subunit that has at least about 40% homology to protein encoded by DNA disclosed herein that encodes an $\alpha_1$ subunit of a human calcium channel. In particular, a splice variant of any of the $\alpha_1$ subunits (or any of the subunits particularly disclosed herein) will contain regions (at least one exon) of divergence and one or more regions (at least one exon, typically more than about 16 nucleotides, and generally substantially more) that have 100% homology with one or more of the $\alpha_1$ subunit subtypes provided herein, and will also contain a region that has substantially less homology, since it is derived from a different exon. It is well within the skill of those in this art to identify exons and splice variants. Thus, for example, an $\alpha_{1A}$ subunit will be readily identifiable, because it will share at least about 40% protein homology with one of the $\alpha_{1A}$ subunits disclosed herein, and will include at least one region (one exon) that is 100% homologous. It will also have activity, as discussed below, that indicates that it is an $\alpha_1$ subunit.

An $\alpha_1$ subunit may be identified by its ability to form a calcium channel. Typically, $\alpha_1$ subunits have molecular masses greater than at least about 120 kD. Also, hydropathy plots of deduced $\alpha_1$ subunit amino acid sequences indicate that the $\alpha_1$ subunits contain four internal repeats, each containing six putative transmembrane domains.

The activity of a calcium channel may be assessed in vitro by methods known to those of skill in the art, including the electrophysiological and other methods described herein. Typically, $\alpha_1$ subunits include regions with which one or more modulators of calcium channel activity, such as a 1,4-DHP or ω-CgTx, interact directly or indirectly. Types of $\alpha_1$ subunits may be distinguished by any method known to those of skill in the art, including on the basis of binding specificity. For example, it has been found herein that $\alpha_{1B}$ subunits participate in the formation of channels that have previously been referred to as N-type channels, $\alpha_{1D}$ subunits participate in the formation of channels that had previously been referred to as L-type channels, $\alpha_{1A}$ subunits appear to participate in the formation of channels that exhibit characteristics typical of channels that had previously been designated P-type channels, and $\alpha_{1F}$ subunits appear to participate in channels that exhibit activities associated with T-type channels. Thus, for example, the activity of channels that contain the $\alpha_{1B}$ subunit are insensitive to 1,4-DHPs; whereas the activity of channels that contain the $\alpha_{1D}$ subunit are modulated or altered by a 1,4-DHP. It is presently preferable to refer to calcium channels based on pharmacological characteristics and current kinetics and to avoid historical designations. Types and subtypes of $\alpha_1$ subunits may be characterized on the basis of the effects of such modulators on the subunit or a channel containing the subunit as well as differences in currents and current kinetics produced by calcium channels containing the subunit. The $\alpha_{1F}$ subunits may be further identified by the presence the notably long intracellular loop regions, such as between transmembrane domains I and II (e.g., nt 1506 to nt 2627 of SEQ ID No. 49), and also the loop in domain I.

As used herein, an $\alpha_2$ subunit is encoded by DNA that hybridizes to the DNA provided herein under conditions of low stringency or encodes a protein that has at least about 40% homology with that disclosed herein. Such DNA encodes a protein that typically has a molecular mass greater than about 120 kD, but does not form a calcium channel in the absence of an $\alpha_1$ subunit, and may alter the activity of a calcium channel that contains an $\alpha_1$ subunit. Subtypes of the $\alpha_2$ subunit that arise as splice variants are designated by lower case letter, such as $\alpha_{2a}$ ... $\alpha_{2e}$. In addition, the $\alpha_2$ subunit and the large fragment produced when the protein is subjected to reducing conditions appear to be glycosylated with at least N-linked sugars and do not specifically bind to the 1,4-DHPs and phenylalkylamines that specifically bind to the $\alpha_1$ subunit. The smaller fragment, the C-terminal fragment, is referred to as the $\delta$ subunit and includes amino acids from about 946 (SEQ ID No. 11) through about the C-terminus. This fragment may dissociate from the remaining portion of $\alpha_2$ when the $\alpha_2$ subunit is exposed to reducing conditions. For purposes herein $\alpha_2$ is also referred to as $\alpha_2\delta$. Thus, reference to $\alpha_2\delta$ means the $\alpha_2$ subunit, including the C-terminal $\delta$ portion.

As used herein, a $\beta$ subunit is encoded by DNA that hybridizes to the DNA provided herein under conditions of low stringency or encodes a protein that has at least about 40% homology with that disclosed herein and is a protein that typically has a molecular mass lower than the a subunits and on the order of about 50–80 kD, does not form a detectable calcium channel in the absence of an $\alpha_1$ subunit, but may alter the activity of a calcium channel that contains an $\alpha_1$ subunit or that contains an $\alpha_1$ and $\alpha_2$ subunit.

Types of the $\beta$ subunit that are encoded by different genes are designated with subscripts, such as $\beta_1$, $\beta_2$, $\beta_3$ and $\beta_4$. Subtypes of $\beta$ subunits that arise as splice variants of a particular type are designated with a numerical subscript referring to the type and to the variant. Such subtypes include, but are not limited to the $\beta_1$ splice variants, including $\beta_{1-1}$–$\beta_{1-5}$ and $\beta_2$ variants, including $\beta_{2C}$–$\beta_{2E}$.

As used herein, a $\gamma$ subunit is a subunit encoded by DNA disclosed herein as encoding the $\gamma$ subunit and may be isolated and identified using the DNA disclosed herein as a probe by hybridization or other such method known to those of skill in the art, whereby full-length clones encoding a γ subunit may be isolated or constructed. A γ subunit will be encoded by DNA that hybridizes to the DNA provided herein under conditions of low stringency or exhibits sufficient sequence homology to encode a protein that has at least about 40% homology with the γ subunit described herein.

Thus, one of skill in the art, in light of the disclosure herein, can identify DNA encoding $\alpha_1$, $\alpha_2$, $\beta$, $\delta$ and $\gamma$ calcium channel subunits, including types encoded by different genes and subtypes that represent splice variants. For example, DNA probes based on the DNA disclosed herein may be used to screen an appropriate library, including a genomic or cDNA library, for hybridization to the probe and obtain DNA in one or more clones that includes an open reading fragment that encodes an entire protein. Subsequent to screening an appropriate library with the DNA disclosed herein, the isolated DNA can be examined for the presence of an open reading frame from which the sequence of the encoded protein may be deduced. Determination of the molecular weight and comparison with the sequences herein should reveal the identity of the subunit as an $\alpha_1$, $\alpha_2$ etc. subunit. Functional assays may, if necessary, be used to determine whether the subunit is an $\alpha_1$, $\alpha_2$ subunit or $\beta$ subunit.

For example, DNA encoding an $\alpha_{1A}$ subunit may be isolated by screening an appropriate library with DNA, encoding all or a portion of the human $\alpha_{1A}$ subunit. Such DNA includes the DNA in the phage deposited under ATCC Accession No. 75293 that encodes a portion of an $\alpha_1$ subunit. DNA encoding an $\alpha_{1A}$ subunit may be obtained from an appropriate library by screening with an oligonucleotide having all or a portion of the sequence set forth in SEQ ID No. 21, 22 and/or 23 or with the DNA in the deposited phage. Alternatively, such DNA may have a sequence that encodes an $\alpha_{1A}$ subunit that is encoded by SEQ ID NO. 22 or 23.

Similarly, DNA encoding $\beta_3$ may be isolated by screening a human cDNA library with DNA probes prepared from the plasmid β1.42 deposited under ATCC Accession No. 69048 or may be obtained from an appropriate library using probes having sequences prepared according to the sequences set forth in SEQ ID Nos. 19 and/or 20. Also, DNA encoding $\beta_4$ may be isolated by screening a human cDNA library with DNA probes prepared according to DNA set forth in SEQ ID No. 27, which sets forth the DNA sequence of a clone encoding a $\beta_4$ subunit. The amino acid sequence is set forth in SEQ ID No. 28. Any method known to those of skill in the art for isolation and identification of DNA and preparation of full-length genomic or cDNA clones, including methods exemplified herein, may be used.

The subunit encoded by isolated DNA may be identified by comparison with the DNA and amino acid sequences of the subunits provided herein. Splice variants share extensive regions of homology, but include non-homologous regions, subunits encoded by different genes share a uniform distribution of non-homologous sequences.

As used herein, a splice variant refers to a variant produced by differential processing of a primary transcript of genomic DNA that results in more than one type of mRNA. Splice variants may occur within a single tissue type or among tissues (tissue-specific variants). Thus, cDNA clones that encode calcium channel subunit subtypes that have regions of identical amino acids and regions of different amino acid sequences are referred to herein as "splice variants".

As used herein, a "calcium channel-selective ion" is an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel-selective ion.

As used herein, a compound that modulates calcium channel activity is one that affects the ability of the calcium channel to pass calcium channel-selective ions or affects other detectable calcium channel features, such as current kinetics. Such compounds include calcium channel antagonists and agonists and compounds that exert their effect on the activity of the calcium channel directly or indirectly.

As used herein, a "substantially pure" subunit or protein is a subunit or protein that is sufficiently free of other polypeptide contaminants to appear homogeneous by SDS-PAGE or to be unambiguously sequenced.

As used herein, selectively hybridize means that a DNA fragment hybridizes to a second fragment with sufficient specificity to permit the second fragment to be identified or isolated from among a plurality of fragments. In general, selective hybridization occurs at conditions of high stringency.

As used herein, heterologous or foreign DNA and RNA are used interchangeably and refer to DNA or RNA that does not occur naturally as part of the genome in which it is present or which is found in a location or locations in the genome that differ from that in which it occurs in nature. It is DNA or RNA that is not endogenous to the cell and has been artificially introduced into the cell. Examples of heterologous DNA include, but are not limited to, DNA that encodes a calcium channel subunit and DNA that encodes RNA or proteins that mediate or alter expression of endogenous DNA by affecting transcription, translation, or other regulatable biochemical processes. The cell that expresses the heterologous DNA, such as DNA encoding a calcium channel subunit, may contain DNA encoding the same or different calcium channel subunits. The heterologous DNA need not be expressed and may be introduced in a manner such that it is integrated into the host cell genome or is maintained episomally.

As used herein, operative linkage of heterologous DNA to regulatory and effector sequences of nucleotides, such as promoters, enhancers, transcriptional and translational stop sites, and other signal sequences, refers to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art [see, e.g., Maniatis et al. (1982) *Molecular Cloning: A Laboratory Manual*, Cold Spring Harbor Laboratory Press, Cold Spring Harbor, N.Y.].

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Selection and use of such vectors and plasmids are well within the level of skill of the art.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or may integrate into the host cell genome.

As used herein, a promoter region refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, a recombinant eukaryotic cell is a eukaryotic cell that contains heterologous DNA or RNA.

As used herein, a recombinant or heterologous calcium channel refers to a calcium channel that contains one or more subunits that are encoded by heterologous DNA that has been introduced into and expressed in a eukaryotic cell that expresses the recombinant calcium channel. A recombinant calcium channel may also include subunits that are produced by DNA endogenous to the cell. In certain embodiments, the recombinant or heterologous calcium channel may contain only subunits that are encoded by heterologous DNA.

As used herein, "functional" with respect to a recombinant or heterologous calcium channel means that the channel is able to provide for and regulate entry of calcium channel-selective ions, including, but not limited to, $Ca^{2+}$ or $Ba^{2+}$, in response to a stimulus and/or bind ligands with affinity for the channel. Preferably such calcium channel activity is distinguishable, such as by electrophysiological, pharmacological and other means known to those of skill in the art, from any endogenous calcium channel activity that is in the host cell.

As used herein, a T-type channel or LVA type channel typically refers to a calcium channel that exhibits a low-threshold calcium current that is activated and inactivated at low voltages compared to calcium channels (such as those that include an $\alpha_{1D}$ subunit) referred to as high voltage activated (HVA) channels. In addition or alternatively, a T-type channel may be characterized by distinct biophysical features, such as slow deactivation rates, very low conductances (5–9 pS) and voltage-dependent inactivation. T channels may exhibit a relatively high degree of sensitivity to mibefradil and/or a relatively high degree of resistance to the Conus snail toxins GVIA and MVIIC as well as the arachnid toxins AgaIIIA and AgaIVA compared to HVA calcium channels. These channels also typically exhibit reduced affinity for cadmium. T-type channels or LVA type channels may also be characterized at the nucleic acid level by the presence of one or more extended intracellular loop (see, e.g., SEQ ID NO. 49) between transmembrane domains, such as between transmembrane domains I and II.

As used herein, a peptide having an amino acid sequence substantially as set forth in a particular SEQ ID No. 51 and 52 includes peptides that may have the same function but may include minor variations in sequence, such as conservative amino acid changes or minor deletions or insertions that do not alter the activity of the peptide. The activity of a calcium channel receptor subunit peptide refers to its ability to form functional calcium channels with other such subunits.

As used herein, a physiological concentration of a compound is that which is necessary and sufficient for a biological process to occur. For example, a physiological concentration of a calcium channel-selective ion is a concentration of the calcium channel-selective ion necessary and sufficient to provide an inward current when the channels open.

As used herein, activity of a calcium channel refers to the movement of a calcium channel-selective ion through a calcium channel. Such activity may be measured by any method known to those of skill in the art, including, but not limited to, measurement of the amount of current which flows through the recombinant channel in response to a stimulus.

As used herein, a "functional assay" refers to an assay that identifies functional calcium channels. A functional assay, thus, is an assay to assess function.

As understood by those skilled in the art, assay methods for identifying compounds, such as antagonists and agonists, that modulate calcium channel activity, generally require comparison to a control. One type of a "control" cell or "control" culture is a cell or culture that is treated substantially the same as the cell or culture exposed to the test compound except that the control culture is not exposed to the test compound. Another type of a "control" cell or "control" culture may be a cell or a culture of cells which are identical to the transfected cells except the cells employed for the control culture do not express functional calcium channels. In this situation, the response of test cell to the test compound is compared to the response (or lack of response) of the calcium channel-negative cell to the test compound, when cells or cultures of each type of cell are exposed to substantially the same reaction conditions in the presence of the compound being assayed. For example, in methods that use patch clamp electrophysiological procedures, the same cell can be tested in the presence and absence of the test compound, by changing the external solution bathing the cell as known in the art.

It is also understood that each of the subunits disclosed herein may be modified by making conservative amino acid substitutions and the resulting modified subunits are contemplated herein. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p.224). Such substitutions are preferably, although not exclusively, made in accordance with those set forth in TABLE 1 as follows:

TABLE 1

| Original residue | Conservative substitution |
| --- | --- |
| Ala (A) | Gly; Ser |
| Arg (R) | Lys |
| Asn (N) | Gln; His |

TABLE 1-continued

| Original residue | Conservative substitution |
|---|---|
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art. Mutation may be effected by any method known to those of skill in the art, including site-specific or site-directed mutagenesis of DNA encoding the protein and the use of DNA amplification methods using primers to introduce and amplify alterations in the DNA template.

Identification and Isolation of DNA Encoding Human Calcium Channel Subunits

Methods for identifying and isolating DNA encoding $\alpha_1$, $\alpha_2$, $\beta$ and $\gamma$ subunits of human calcium channels are provided. Identification and isolation of such DNA may be accomplished by hybridizing, under appropriate conditions, at least low stringency whereby DNA that encodes the desired subunit is isolated, restriction enzyme-digested human DNA with a labeled probe having at least 14, preferably 16 or more nucleotides and derived from any contiguous portion of DNA having a sequence of nucleotides set forth herein by sequence identification number. Once a hybridizing fragment is identified in the hybridization reaction, it can be cloned employing standard cloning techniques known to those of skill in the art. Full-length clones may be identified by the presence of a complete open reading frame and the identity of the encoded protein verified by sequence comparison with the subunits provided herein and by functional assays to assess calcium channel-forming ability or other function. This method can be used to identify genomic DNA encoding the subunit or cDNA encoding splice variants of human calcium channel subunits generated by alternative splicing of the primary transcript of genomic subunit DNA. For instance, DNA, cDNA or genomic DNA, encoding a calcium channel subunit may be identified by hybridization to a DNA probe and characterized by methods known to those of skill in the art, such as restriction mapping and DNA sequencing, and compared to the DNA provided herein in order to identify heterogeneity or divergence in the sequences of the DNA. Such sequence differences may indicate that the transcripts from which the cDNA was produced result from alternative splicing of a primary transcript, if the non-homologous and homologous regions are clustered, or from a different gene if the non-homologous regions are distributed throughout the cloned DNA. Splice variants share regions of 100% homology.

Any suitable method for isolating genes using the DNA provided herein may be used. For example, oligonucleotides corresponding to regions of sequence differences have been used to isolate, by hybridization, DNA encoding the full-length splice variant and can be used to isolate genomic clones. A probe, based on a nucleotide sequence disclosed herein, which encodes at least a portion of a subunit of a human calcium channel, such as a tissue-specific exon, may be used as a probe to clone related DNA, to clone a full-length cDNA clone or genomic clone encoding the human calcium channel subunit.

Labeled, including, but not limited to, radioactively or enzymatically labeled, RNA or single-stranded DNA of at least 14 substantially contiguous bases, preferably 16 or more, generally at least 30 contiguous bases of a nucleic acid which encodes at least a portion of a human calcium channel subunit, the sequence of which nucleic acid corresponds to a segment of a nucleic acid sequence disclosed herein by reference to a SEQ ID No. are provided. Such nucleic acid segments may be used as probes in the methods provided herein for cloning DNA encoding calcium channel subunits. See, generally, Sambrook et al. (1989) *Molecular Cloning: A Laboratory Manual*, 2nd Edition, Cold Spring Harbor Laboratory Press.

In addition, nucleic acid amplification techniques, which are well known in the art, can be used to locate splice variants of calcium channel subunits by employing oligonucleotides based on DNA sequences surrounding the divergent sequence primers for amplifying human RNA or genomic DNA. Size and sequence determinations of the amplification products can reveal splice variants. Furthermore, isolation of human genomic DNA sequences by hybridization can yield DNA containing multiple exons, separated by introns, that correspond to different splice variants of transcripts encoding human calcium channel subunits.

DNA encoding types and subtypes of each of the $\alpha_1$, $\alpha_2$, $\beta$ and $\gamma$ subunits of voltage-dependent human calcium channels has been cloned herein by nucleic acid amplication of cDNA from selected tissues or by screening human cDNA libraries prepared from isolated poly A+mRNA from cell lines or tissue of human origin having such calcium channels. Among the sources of such cells or tissue for obtaining mRNA are human brain tissue or a human cell line of neural origin, such as a neuroblastoma cell line, human skeletal muscle or smooth muscle cells, and the like. Methods of preparing cDNA libraries are well known in the art [see generally Ausubel et al. (1987) *Current Protocols in Molecular Biology*, Wiley-Interscience, New York; and Davis et al. (1986) *Basic Methods in Molecular Biology*, Elsevier Science Publishing Co., New York].

Preferred regions from which to construct probes include 5' and/or 3' coding sequences, sequences predicted to encode transmembrane domains, sequences predicted to encode cytoplasmic loops, signal sequences, ligand-binding sites, and other functionally significant sequences (see Table, below). Either the full-length subunit-encoding DNA or fragments thereof can be used as probes, preferably labeled with suitable label means for ready detection. When fragments are used as probes, preferably the DNA sequences will be typically from the carboxyl-end-encoding portion of the DNA, and most preferably will include predicted transmembrane domain-encoding portions based on hydropathy analysis of the deduced amino acid sequence [see, e.g., Kyte and Doolittle [(1982) *J. Mol. Biol.* 167:105].

Particularly preferred regions from which to construct probes for the isolation of DNA encoding a human $\alpha_{-1F}$ subunit include the nucleic acid sequence encoding the notably long intracellular loop located between transmembrane Domains I and II (e.g., nt 1506 to nt 2627 of SEQ ID No. 49). Probes for isolating DNA encoding a human $\alpha_{-1F}$ subunit are preferably 14 or 16 contiguous nucleotides in length. In some instances, probes of 30 or 50 nucleotides are preferred and in other instances probes between 50 to 100 nucleotides are preferred.

Riboprobes that are specific for human calcium channel subunit types or subtypes have been prepared. These probes are useful for identifying expression of particular subunits in selected tissues and cells. The regions from which the probes were prepared were identified by comparing the DNA and amino acid sequences of all known α or β subunit subtypes. Regions of least homology, preferably human-derived sequences, and generally about 250 to about 600 nucleotides were selected. Numerous riboprobes for α and β subunits have been prepared; some of these are listed in the following Table.

TABLE 2

SUMMARY OF RNA PROBES

| SUBUNIT SPECIFICITY | NUCLEOTIDE POSITION | PROBE NAME | PROBE TYPE | ORIEN-TATION |
|---|---|---|---|---|
| α1A generic | 3357–3840 | pGEM7Zα1A* | ribo-probe | n/a |
| | 761–790 | SE700 | oligo | antisense |
| | 3440–3464 | SE718 | oligo | antisense |
| | 3542–3565 | SE724 | oligo | sense |
| α1B generic | 3091–3463 | pGEM7Zα1B$_{cyt}$ | ribo-probe | n/a |
| | 6635–6858 | pGEM7Zα1B$_{cooh}$ | ribo-probe | n/a |
| α1B-1 specific | 6490–6676 | pCRII α1B-1/187 | ribo-probe | n/a |
| α1E generic | 3114–3462 | pGEM7Zα1E | ribo-probe | n/a |
| α2b | 1321–1603 | pCRIIα2b | ribo-probe | n/a |
| β generic (?) | 212–236 | SE300 | oligo | antisense |
| β1 generic | 1267–1291 | SE301 | oligo | antisense |
| β1-2 specific | 1333–1362 | SE17 | oligo | antisense |
| | 1682–1706 | SE23 | oligo | sense |
| | 2742–2766 | SE43 | oligo | antisense |
| | 27–56 | SE208 | oligo | antisense |
| | 340–364 | SE274 | oligo | antisense |
| | 340–364 | SE275 | oligo | sense |
| β3 specific | 1309–1509 | | ribo-probe | n/a |
| β4 specific | 1228–1560 | | ribo-probe | n/a |

*The pGEM series are available from Promega, Madison WI; see also, U.S. Pat. No. 4,766,072.

The above-noted nucleotide regions are also useful in selecting regions of the protein for preparation of subunit-specific antibodies, discussed below.

The DNA clones and fragments thereof provided herein thus can be used to isolate genomic clones encoding each subunit and to isolate any splice variants by hybridization screening of libraries prepared from different human tissues. Nucleic acid amplification techniques, which are well known in the art, can also be used to locate DNA encoding splice variants of human calcium channel subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human calcium channel subunits.

Once DNA encoding a calcium channel subunit is isolated, ribonuclease (RNase) protection assays can be employed to determine which tissues express mRNA encoding a particular calcium channel subunit or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualized by gel electrophoresis and autoradiography. In situ hybridization techniques can also be used to determine which tissues express mRNA encoding a particular calcium channel subunit. The labeled subunit-encoding DNA clones are hybridized to different tissue slices to visualize subunit mRNA expression.

With respect to each of the respective subunits ($\alpha_1$, $\alpha_2$, $\beta$ or $\gamma$) of human calcium channels, once the DNA encoding the channel subunit was identified by a nucleic acid screening method, the isolated clone was used for further screening to identify overlapping clones. Some of the cloned DNA fragments can and have been subcloned into an appropriate vector such as pIBI24/25 (IBI, New Haven, Conn.), M13mp 18/19, pGEM4, pGEM3, pGEM7Z, pSP72 and other such vectors known to those of skill in this art, and characterized by DNA sequencing and restriction enzyme mapping. A sequential series of overlapping clones may thus be generated for each of the subunits until a full-length clone can be prepared by methods, known to those of skill in the art, that include identification of translation initiation (start) and translation termination (stop) codons. For expression of the cloned DNA, the 5' noncoding region and other transcriptional and translational control regions of such a clone may be replaced with an efficient ribosome binding site and other regulatory regions as known in the art. Other modifications of the 5' end, known to those of skill in the art, that may be required to optimize translation and/or transcription efficiency may also be effected, if deemed necessary.

Examples II–VIII, below, describe in detail the cloning of each of the various subunits of a human calcium channel as well as subtypes and splice variants, including tissue-specific variants thereof. In the few instances in which partial sequences of a subunit are disclosed, it is well within the skill of the art, in view of the teaching herein, to obtain the corresponding full-length clones and sequence thereof encoding the subunit, subtype or splice variant thereof using the methods described above and exemplified below.

Identification and Isolation of DNA Encoding Additional $\alpha_1$ Human Calcium Channel Subunit Types and Subtypes DNA encoding additional $\alpha_1$ subunits can be isolated and identified using the DNA provided herein as described for the $\alpha_{1A}$, $\alpha_{1B}$, $\alpha_{1C}$, $\alpha_{1D}$, $\alpha_{1E}$ and $\alpha_{1F}$ subunits or using other methods known to those of skill in the art. In particular, the DNA provided herein may be used to screen appropriate libraries to isolate related DNA. Full-length clones can be constructed using methods, such as those described herein, and the resulting subunits characterized by comparison of their sequences and electrophysiological and pharmacological properties with the subunits exemplified herein.

A number of voltage-dependent calcium channel $\alpha_1$ subunit genes, which are expressed in the human CNS and in other tissues, have been identified and have been designated as $\alpha_{1A}$, $\alpha_{1B}$ (or VDCC IV), $\alpha_{1C}$ (or VDCC II), $\alpha_{1D}$ (or VDCC II), $\alpha_{1E}$ and $\alpha_{1F}$. DNA, isolated from a human DNA libraries that encodes each of the subunit types has been isolated. DNA encoding subtypes of each of the types, which arise as splice variants are also provided. Subtypes are herein designated, for example, as $\alpha_{1B-1}$, $\alpha_{1B-2}$. The $\alpha_{1F}$ subunit is of particular interest herein The $\alpha_1$ subunit types A, B, C, D, E and F of voltage-dependent calcium channels, and subtypes thereof, differ with respect to sensitivity to known classes of calcium channel agonists and antagonists, such as DHPs, phenylalkylamines, omega conotoxins ($\omega$-CgTx), the funnel web spider toxin $\omega$-Aga-IV, pyrazonoylguanidines and or in other physical and structural properties. These subunit types also appear to differ in the holding potential and in the kinetics of currents produced upon depolarization of cell membranes containing calcium channels that include different types of $\alpha_1$ subunits.

DNA that encodes an $\alpha_1$ subunit that binds to at least one compound selected from among dihydropyridines, phenylalkylamines, $\omega$-CgTx, components of funnel web spider toxin, and pyrazonoylguanidines is provided. For example, the $\alpha_{1B}$ subunit provided herein appears to specifically interact with $\omega$-CgTx in N-type channels, and the $\alpha_{1D}$ subunit provided herein interacts with DHPs in L-type channels.

Identification and Isolation of DNA Encoding the $\alpha_{1D}$ Human Calcium Channel Subunit The $\alpha_{1D}$ subunit cDNA has been isolated using fragments of the rabbit skeletal muscle calcium channel $\alpha_1$ subunit cDNA as a probe to screen a cDNA library of a human neuroblastoma cell line, IMR32, to obtain clone $\alpha$1.36. This clone was used as a probe to screen additional IMR32 cell cDNA libraries to obtain overlapping clones, which were then employed for screening until a sufficient series of clones to span the length of the nucleotide sequence encoding the human $\alpha_{1D}$ subunit was obtained. Full-length clones encoding $\alpha_{1D}$ were constructed by ligating portions of partial $\alpha_{1D}$ clones as described in Example II. SEQ ID No. 1 shows the 7,635 nucleotide sequence of the cDNA encoding the $\alpha_{1D}$ subunit. There is a 6,483 nucleotide sequence reading frame which encodes a sequence of 2,161 amino acids (as set forth in SEQ ID No. 1).

SEQ ID No. 2 provides the sequence of an alternative exon encoding the IS6 transmembrane domain [see Tanabe, T., et al. (1987) Nature 328:313–318 for a description of transmembrane domain terminology] of the $\alpha_{1D}$ subunit.

SEQ ID No. 1 also shows the 2,161 amino acid sequence deduced from the human neuronal calcium channel $\alpha_{1D}$ subunit DNA. Based on the amino acid sequence, the $\alpha_{1D}$ protein has a calculated Mr of 245,163. The $\alpha_{1D}$ subunit of the calcium channel contains four putative internal repeated sequence regions. Four internally repeated regions represent 24 putative transmembrane segments, and the amino- and carboxyl-termini extend intracellularly.

The $\alpha_{1D}$ subunit has been shown to mediate DHP-sensitive, high-voltage-activated, long-lasting calcium channel activity. This calcium channel activity was detected when oöcytes were co-injected with RNA transcripts encoding an $\alpha_{1D}$ and $\beta_{1-2}$ or $\alpha_{1D}$, $\alpha_{2b}$ and $\beta_{1-2}$ subunits. This activity was distinguished from $Ba^{2+}$ currents detected when oöcytes were injected with RNA transcripts encoding the $\beta_{1-2}\pm\alpha_{2b}$ subunits. These currents pharmacologically and biophysically resembled $Ca^{2+}$ currents reported for uninjected oöcytes.

Identification and Isolation of DNA Encoding the $\alpha_{1A}$ Human Calcium Channel Subunit Biological material containing DNA encoding a portion of the $\alpha_{1A}$ subunit had been deposited in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

A portion of an $\alpha_{1A}$ subunit is encoded by an approximately 3 kb insert in $\lambda$gt10 phage designated $\alpha$1.254 in E. coli host strain NM514. A phage lysate of this material has been deposited as at the American Type Culture Collection under ATCC Accession No. 75293, as described above. DNA encoding $\alpha_{1A}$ may also be identified by screening with a probe prepared from DNA that has SEQ ID No. 21:

5' CTCAGTACCATCTCTGATACCAGCCCCA 3'.

$\alpha_{1A}$ splice variants have been obtained. The sequences of two $\alpha_{1A}$ splice variants, $\alpha_{1a-1}$, and $\alpha_{1a-2}$ are set forth in SEQ. ID Nos. 22 and 23. Other splice variants may be obtained by screening a human library as described above or using all or a portion of the sequences set forth in SEQ ID Nos. 22 and 23.

Identification and Isolation of DNA Encoding the $\alpha_{1B}$ Human Calcium Channel Subunit DNA encoding the $\alpha_{1B}$ subunit was isolated by screening a human basal ganglia cDNA library with fragments of the rabbit skeletal muscle calcium channel $\alpha_1$ subunit-encoding cDNA. A portion of one of the positive clones was used to screen an IMR32 cell cDNA library. Clones that hybridized to the basal ganglia DNA probe were used to further screen an IMR32 cell cDNA library to identify overlapping clones that in turn were used to screen a human hippocampus cDNA library. In this way, a sufficient series of clones to span nearly the entire length of the nucleotide sequence encoding the human $\alpha_{1B}$ subunit was obtained. Nucleic acid amplification of specific regions of the IMR32 cell $\alpha_{1B}$ mRNA yielded additional segments of the $\alpha_{1B}$ coding sequence.

A full-length $\alpha_{1B}$ DNA clone was constructed by ligating portions of the partial cDNA clones as described in Example II.C. SEQ ID Nos. 7 and 8 show the nucleotide sequences of DNA clones encoding the $\alpha_{1B}$ subunit as well as the deduced amino acid sequences. The $\alpha_{1B}$ subunit encoded by SEQ ID No. 7 is referred to as the $\alpha_{1B-1}$ subunit to distinguish it from another $\alpha_{1B}$ subunit, $\alpha_{1B-2}$, encoded by the nucleotide sequence shown as SEQ ID No. 8, which is derived from alternative splicing of the $\alpha_{1B}$ subunit transcript.

Nucleic acid amplification of IMR32 cell mRNA using oligonucleotide primers designed according to nucleotide sequences within the $\alpha_{1B-1}$-encoding DNA has identified variants of the $\alpha_{1B}$ transcript that appear to be splice variants because they contain divergent coding sequences.

Identification and Isolation of DNA Encoding the $\alpha_{1C}$ Human Calcium Channel Subunit Numerous $\alpha_{1C}$-specific DNA clones were isolated. Characterization of the sequence revealed the $\alpha_{1C}$ coding sequence, the $\alpha_{1C}$ initiation of translation sequence, and an alternatively spliced region of $\alpha_{1C}$. Alternatively spliced variants of the $\alpha_{1C}$ subunit have been identified. SEQ ID No. 3 sets forth DNA encoding a substantial protion of an $\alpha_{1C}$ subunit. The DNA sequences set forth in SEQ ID No. 4 and No. 5 encode two possible amino terminal ends of the $\alpha_{1C}$ protein. SEQ ID No. 6 encodes an alternative exon for the IV S3 transmembrane domain. The sequences of substantial portions of two aid splice variants, designated $\alpha_{1C-1}$ and $\alpha_{1C-2}$, are set forth in SEQ ID NOs. 3 and 36, respectively.

The isolation and identification of DNA clones encoding portions of the $\alpha_{1C}$ subunit is described in detail in Example II.

Identification and Isolation of DNA Encoding the $\alpha_{1E}$ Human Calcium Channel Subunit DNA encoding $\alpha_{1E}$ human calcium channel subunits have been isolated from an oligo dT-primed human hippocampus library. The resulting clones, which are splice variants, were designated $\alpha_{1E\text{-}1}$ and $\alpha_{1E\text{-}3}$. The subunit designated $\alpha_{1E\text{-}1}$ has the amino acid sequence set forth in SEQ ID No. 24, and a subunit designated $\alpha_{1E\text{-}3}$ has the amino acid sequence set forth in SEQ ID No. 25. These splice variants differ by virtue of a 57 base pair insert between nucleotides 2405 and 2406 of SEQ. ID No. 24.

The $\alpha_{1E}$ subunits provided herein appear to participate in the formation of calcium channels that have properties of high-voltage activated calcium channels and low-voltage activated channels. These channels are rapidly inactivating compared to other high voltage-activated calcium channels. In addition these channels exhibit pharmacological profiles that are similar to voltage-activated channels, but are also sensitive to DHPs and ω-Aga-IVA, which block certain high voltage activated channels. Additional details regarding the electrophysiology and pharmacology of channels containing $\alpha_{1E}$ subunits is provided in Example VII. F.

Identification and Isolation of DNA Encoding the $\alpha_{1F}$ Human Calcium Channel Subunit Calcium channels that contain $\alpha_{1F}$ should exhibit properties that differ from known HVA channels, formed from the $\alpha_{1A}$–$\alpha_{1E}$ calcium channel subunits. Such differences may include low voltage activation, voltage-dependent inactivation, relatively high sensitivity to mibefradil and relatively high resistance to snail and arachnid toxins that inhibit most HVA channels (e.g., spider venom toxins ω-AgaIIIA and ω-AgaIVA and the Conus snail toxin GVIA). In addition $\alpha_{1F}$-subunits may be identified by homology with other $\alpha_1$-subunits and additionally by presence of an extended intracellular loop in the encoded subunit (see, e.g., SEQ No. 49, nucleotides 1506–2627) located between transmembrane domains I and II. This region in $\alpha_{1F}$ is extended compared to other calcium channel $\alpha_1$ subunits, such as $\alpha_{1A}$–$\alpha_{1E}$.

DNA encoding an $\alpha_{1F}$-subunit may be isolated using the DNA provided herein. In particular, probes of at least about 16 nucleotides or 30 nucleotides or other suitable length, such 14, 30, 100 etc. bases, may be used to screen selected libraries, including mammalian DNA libraries. The selected libraries are preferably prepared from mammalian tissue or cell sources known to express T-type channels. The seqeuence of the probe is preferably based on the sequence of the intracellular loop located between transmembrane domains I and II (see, e.g., SEQ ID No. 49).

The DNA encoding the $\alpha_{1F}$ subunit was isolated by amplifying a region of genes encoding an $\alpha_1$ subunit expressed in a human thyroid carcinoma cell line (TT cells) using degenerate oligonucleotide primers. A portion of one of the positive clones was used to further screen a human thyroid carcinoma cDNA library to identify overlapping clones that span the entire length of the nucleotide sequence encoding the human $\alpha_{1F}$ subunit. A full-length $\alpha_{1F}$ DNA clone can be constructed by ligating portions of the partial cDNA clones as described in Example II. SEQ ID No. 49 set forth the nucleotide sequence of a clone encoding an $\alpha_{1F}$ subunit as well as the deduced amino acid sequence.

A comparison of the nucleic acid and deduced amino acid sequences of this $\alpha_{1F}$ calcium channel subunit with other human $\alpha_1$ subunits reveals several distinct features. First, the intracellular loop between transmembrane Domains I and II is notably long. As exemplified in SEQ ID No. 49, the intracellular loop of human $\alpha_{1F}$ subunit is 1,122 nt in length whereas the corresponding intracellular loops in the other human $\alpha_1$ subunits described herein range from 351 to 381 nt in length. Thus, the intracellular loop of human $\alpha_{1F}$ is nearly 250 amino acids longer than human $\alpha_1$ subunits found in HVA calcium channels. The deduced amino acid sequence of this region (aa 420 to aa 794 of SEQ ID No. 50) contains a large number of proline residues and includes a poly-HIS region of 9 contiguous histidine residues (aa 52 to aa 528 of SEQ ID No. 50) and a region where 8 of 10 residues are alanine. The large intracellular loop located between transmembrane Domains I and II resembles the large intracellular loops found in a corresponding location in sodium channel a subunits some of which may function as homomers. It has been proposed that T-type channels have an activity that is a hybrid between HVA calcium channels and sodium channel. The $\alpha_{1F}$ subunits provided herein may also function as sodium channels. Thus, subunits with sodium channel activity are provided.

Second, the isolated human $\alpha_{1F}$ subunit lacks amino acid residues that are generally known to be critical (e.g., see De Waard et al. (1996) *FEBS Letters* 380:272–276; Pragnell et al. (1994) *Nature* 368:67–70) for the interaction between $\alpha_1$ subunits and the β subunits. There are at least thirteen residues located in this intracellular loop between transmembrane Domains I and II that form a motif that is highly conserved among $\alpha_1$ subunits, such as $\alpha_{1A}$–$\alpha_{1E}$ described herein (see, also Pragnell et al. (1994) *Nature* 368:67–70).

Third, the human $\alpha_{1F}$ subunit has another notably long extracellular loop in Domain I located between IS5 and IS6. This extracellular loop ranges from 249 to 270 nucleotide residues in other human $\alpha_1$ subunits whereas the human $\alpha_{1F}$ subunit has 426 nucleotide residues. Other distinguishing features may be ascertained by expressing the subunit in cells as described herein.

The nucleic acid encoding the $\alpha_{1F}$ subunit can be used to screen appropriate libraries, particularly mammaliain libraries, and more particularly mammalian libraries from tissues or cells that exhibit T-type channel activity. The encoded subunit can be identified by the above-noted distinguishing properties.

Identification and Isolation of DNA Encoding β Human Calcium Channel Subunits

DNA encoding $\beta_1$

To isolate DNA encoding the $\beta_1$ subunit, a human hippocampus cDNA library was screened by hybridization to a DNA fragment encoding a rabbit skeletal muscle calcium channel $\beta_1$ subunit. A hybridizing clone was selected and was in turn used to isolate overlapping clones until the overlapping clones encompassing DNA encoding the entire human calcium channel β subunit were isolated and sequenced.

Five alternatively spliced forms of the human calcium channel $\beta_1$ subunit have been identified and DNA encoding a number of forms have been isolated. These forms are designated $\beta_{1\text{-}1}$, expressed in skeletal muscle, $\beta_{1\text{-}2}$, expressed in the CNS, $\beta_{1\text{-}3}$, also expressed in the in the CNS, $\beta_{1\text{-}4}$, expressed in aorta tissue and HEK 293 cells, and $\beta_{1\text{-}5}$, expressed in HEK 293 cells. Full-length DNA clones encoding the $\beta_{1\text{-}2}$ and $\beta_{1\text{-}3}$ subunits have been constructed. The subunits $\beta_{1\text{-}1}$, $\beta_{1\text{-}2}$, $\beta_{1\text{-}4}$ and $\beta_{1\text{-}5}$ have been identified by nucleic acid amplification analysis as alternatively spliced forms of the β subunit. Sequences of the $\beta_1$ splice variants are set forth in SEQ ID Nos. 9, 10 and 33–35.

DNA encoding $\beta_2$

DNA encoding the $\beta_2$ splice variants has been obtained. These splice variants include $\beta_{2C}$–$\beta_{2E}$. Splice variants $\beta_{2C}$–$\beta_{2E}$ include all of sequence set forth in SEQ ID No. 26, except for the portion at the 5' end (up to nucleotide 182), which differs among splice variants. The sequence set forth in SEQ ID No. 26 encodes $\beta_{2D}$. Additional splice variants may be isolated using the methods described herein and oligonucleotides including all or portions of the DNA set forth in SEQ ID. No. 26 or may be prepared or obtained as described in the Examples. The sequences of $\beta_2$ splice variants $\beta_{2C}$ and $\beta_{2E}$ are set forth in SEQ ID Nos. 37 and 38, respectively.

DNA encoding $\beta_3$

DNA encoding the $\beta_3$ subunit and any splice variants thereof may be isolated by screening a library, as described above for the $\beta_1$ subunit, using DNA probes prepared according to SEQ ID Nos. 19, 20 or using all or a portion of the deposited $\beta_3$ clone plasmid $\beta$1.42 (ATCC Accession No. 69048).

The *E. coli* host containing plasmid $\beta$1.42 that includes DNA encoding a $\beta_3$ subunit has been deposited as ATCC Accession No. 69048 in the American Type Culture Collection, 12301 Parklawn Drive, Rockville, Md. 20852 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

The $\beta_3$ encoding plasmid is designated $\beta$1.42. The plasmid contains a 2.5 kb EcoRI fragment encoding $\beta_3$ inserted into vector pGem®7zF(+) and has been deposited in *E. coli* host strain DH5$\alpha$. The sequences of $\beta_3$ splice variants, designated $\beta_{3-1}$ and $\beta_{3-2}$ are set forth in SEQ ID Nos. 19 and 20, respectively.

Identification and Isolation of DNA Encoding the $\alpha$2 Human Calcium Channel Subunit DNA encoding a human neuronal calcium channel $\alpha_2$ subunit was isolated in a manner substantially similar to that used for isolating DNA encoding an $\alpha_1$ subunit, except that a human genomic DNA library was probed under low and high stringency conditions with a fragment of DNA encoding the rabbit skeletal muscle calcium channel $\alpha_2$ subunit. The fragment included nucleotides having a sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, which corresponds to U.S. application Ser. No. 07/620,520 (now allowed U.S. application Ser. No. 07/914,231), which is a continuation-in-part of U.S. Ser. No. 176,899, filed Apr. 4, 1988, which applications have been incorporated herein by reference. Example IV describes the isolation of DNA clones encoding $\alpha_2$ subunits of a human calcium channel from a human DNA library using genomic DNA and cDNA clones, identified by hybridization to the genomic DNA, as probes.

SEQ ID Nos. 11 and 29–32 show the sequence of DNA encoding $\alpha_2$ subunits. As described in Example V, nucleic acid amplification analysis of RNA from human skeletal muscle, brain tissue and aorta using oligonucleotide primers specific for a region of the human neuronal $\alpha_2$ subunit cDNA that diverges from the rabbit skeletal muscle calcium channel $\alpha_2$ subunit cDNA identified splice variants of the human calcium channel $\alpha_2$ subunit transcript.

Identification and Isolation of DNA Encoding $\gamma$ Human Calcium Channel Subunits DNA encoding a portion of a human neuronal calcium channel $\gamma$ subunit has been isolated as described in detail in Example VI. SEQ ID No. 14 shows the nucleotide sequence at the 3'-end of this DNA which includes a reading frame encoding a sequence of 43 amino acid residues. Since the portion that has been obtained is homologous to the rabbit clone, described in allowed co-owned U.S. application Ser. No. 07/482,384, the remainder of the clone can be obtained using routine methods.

Antibodies

Antibodies, monoclonal or polyclonal, specific for calcium channel subunit subtypes or for calcium channel types can be prepared employing standard techniques, known to those of skill in the art, using the subunit proteins or portions thereof as antigens. Anti-peptide and anti-fusion protein antibodies can be used [see, for example, Bahouth et al. (1991) *Trends Pharmacol. Sci.* 12:338–343; *Current Protocols in Molecular Biology* (Ausubel et al., eds.) John Wiley and Sons, New York (1984)]. Factors to consider in selecting portions of the calcium channel subunits for use as immunogens (as either a synthetic peptide or a recombinantly produced bacterial fusion protein) include antigenicity accessibility (i.e., extracellular and cytoplasmic domains), uniqueness to the particular subunit, and other factors known to those of skill in this art.

The availability of subunit-specific antibodies makes possible the application of the technique of immunohistochemistry to monitor the distribution and expression density of various subunits (e.g., in normal vs diseased brain tissue). Such antibodies could also be employed in diagnostic, such as LES diagnosis, and therapeutic applications, such as using antibodies that modulate activities of calcium channels.

The antibodies can be administered to a subject employing standard methods, such as, for example, by intraperitoneal, intramuscular, intravenous, or subcutaneous injection, implant or transdermal modes of administration. One of skill in the art can empirically determine dosage forms, treatment regiments, and other paremeters, depending on the mode of administration employed.

Subunit-specific monoclonal antibodies and polyclonal antisera have been prepared. The regions from which the antigens were derived were identified by comparing the DNA and amino acid sequences of all known a or $\beta$ subunit subtypes. Regions of least homology, preferably human-derived sequences were selected. The selected regions or fusion proteins containing the selected regions are used as immunogens. Hydrophobicity analyses of residues in selected protein regions and fusion proteins are also performed; regions of high hydrophobicity are avoided. Also, and more importantly, when preparing fusion proteins in bacterial hosts, rare codons are avoided. In particular, inclusion of 3 or more successive rare codons in a selected host is avoided. Numerous antibodies, polyclonal and monoclonal, specific for $\alpha$ or $\beta$ subunit types or subtypes have been prepared; some of these are listed in the following Table. Exemplary antibodies and peptide antigens used to prepare the antibodies are set forth Table 3:

TABLE 3

| SPECIFICITY | AMINO ACID NUMBER | ANTIGEN NAME | ANTIBODY TYPE |
| --- | --- | --- | --- |
| $\alpha$1 generic | 112–140 | peptide 1A#1 | polyclonal |
| $\alpha$1 generic | 1420–1447 | peptide 1A#2 | polyclonal |
| $\alpha$1A generic | 1048–1208 | $\alpha$1A#2 (b) GST fusion* | polyclonal monoclonal |

TABLE 3-continued

| SPECIFICITY | AMINO ACID NUMBER | ANTIGEN NAME | ANTIBODY TYPE |
|---|---|---|---|
| α1B generic | 983–1106 | α1B#2 (b) GST fusion | polyclonal monoclonal |
| α1B-1 | 2164–2339 | α1B-1#3 GST fusion | polyclonal |
| α1B-2 | 2164–2237 | α1B-2#4 GST fusion | polyclonal |
| α1E generic | 985–1004 (α1E-3) | α1E#2 (a) GST fusion | polyclonal |

*GST gene fusion system is available from Pharmacia; see also, Smith et al. (1988) Gene 67:31. The system provides pGEX plasmids that are designed for inducible, high-level expression of genes or gene fragments as fusions with *Schistosoma japonicum* GST. Upon expression in a bacterial host, the resulting fusion proteins are purified from bacterial lysates by affinity chromatography.

The GST fusion proteins are each specific for the cytoplasmic loop region IIS6-IIS1, which is a region of low subtype homology for all subtypes, including $\alpha_{1C}$ and $\alpha_{1D}$, for which similar fusions and antisera can be prepared.

Preparation of Recombinant Eukaryotic Cells Containing DNA Encoding Heterologous Calcium Channel Subunits DNA encoding one or more of the calcium channel subunits or a portion of a calcium channel subunit may be introduced into a host cell for expression or replication of the DNA. Such DNA may be introduced using methods described in the following examples or using other procedures well known to those skilled in the art. Incorporation of cloned DNA into a suitable expression vector, transfection of eukaryotic cells with a plasmid vector or a combination of plasmid vectors, each encoding one or more distinct genes or with linear DNA, and selection of transfected cells are also well known in the art [see, e.g., Sambrook et al. (1989) *Molecular Cloning: A Laboratory Manual, Second Edition*, Cold Spring Harbor Laboratory Press].

Cloned full-length nucleic acid encoding any of the subunits of a calcium channel may be introduced into a plasmid vector for expression in a eukaryotic cell. Such nucleic acid may be genomic DNA or cDNA or RNA. Presently preferred cells are those containing heterologous DNA encoding an $\alpha_{1F}$ subunit. Host cells may be transfected with one or a combination of the plasmids, each of which encodes at least one calcium channel subunit. Alternatively, host cells may be transfected with linear DNA using methods well known to those of skill in the art.

While the DNA provided herein may be expressed in any eukaryotic cell, including yeast cells such as *P. pastoris* [see, e.g., Cregg et al. (1987) *Bio/Technology* 5:479], mammalian expression systems for expression of the DNA encoding the human calcium channel subunits provided herein are preferred.

The heterologous DNA may be introduced by any method known to those of skill in the art, such as transfection with a vector encoding the heterologous DNA. Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCDNA1, or pcDNA-amp and MMTV promoter-based vectors. DNA encoding the human calcium channel subunits has been inserted in the vector pCDNA1 at a position immediately following the CMV promoter. The vector pCDNA1 is presently preferred.

Stably or transiently transfected mammalian cells may be prepared by methods known in the art by transfecting cells with an expression vector having a selectable marker gene such as the gene for thymidine kinase, dihydrofolate reductase, neomycin resistance or the like, and, for transient transfection, growing the transfected cells under conditions selective for cells expressing the marker gene. Functional voltage-dependent calcium channels have been produced in HEK 293 cells transfected with a derivative of the vector pCDNA1 that contains DNA encoding a human calcium channel subunit.

The heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Eukaryotic cells in which DNA or RNA may be introduced, include any cells that are transfectable by such DNA or RNA or into which such DNA may be injected. Virtually any eukaryotic cell can serve as a vehicle for heterologous DNA. Preferred cells are those that can also express the DNA and RNA and most preferred cells are those that can form recombinant or heterologous calcium channels that include one or more subunits encoded by the heterologous DNA. Such cells may be identified empirically or selected from among those known to be readily transfected or injected. Preferred cells for introducing DNA include those that can be transiently or stably transfected and include, but are not limited to, cells of mammalian origin, such as COS cells, mouse L cells, CHO cells, human embryonic kidney cells, African green monkey cells and other such cells known to those of skill in the art, amphibian cells, such as *Xenopus laevis* oöcytes, or those of yeast such as *Saccharomyces cerevisiae* or *Pichia pastoris*. Preferred cells for expressing injected RNA transcripts or cDNA include *Xenopus laevis* oöbcytes. Cells that are preferred for transfection of DNA are those that can be readily and efficiently transfected. Such cells are known to those of skill in the art or may be empirically identified. Preferred cells include DG44 cells and HEK 293 cells, particularly HEK 293 cells that can be frozen in liquid nitrogen and then thawed and regrown. Such HEK 293 cells are described, for example in U.S. Pat. No. 5,024,939 to Gorman [see, also Stillman et al. (1985) *Mol. Cell. Biol.* 5:2051–2060].

The cells may be used as vehicles for replicating heterologous DNA introduced therein or for expressing the heterologous DNA introduced therein. In certain embodiments, the cells are used as vehicles for expressing the heterologous DNA as a means to produce substantially pure human calcium channel subunits or heterologous calcium channels. Host cells containing the heterologous DNA may be cultured under conditions whereby the calcium channels are expressed. The calcium channel subunits may be purified using protein purification methods known to those of skill in the art. For example, antibodies, such as those provided herein, that specifically bind to one or more of the subunits may be used for affinity purification of the subunit or calcium channels containing the subunits.

Substantially pure subunits of a human calcium channel $\alpha_1$ subunits of a human calcium channel, $\alpha_2$ subunits of a human calcium channel, β subunits of a human calcium channel and γ subunits of a human calcium channel are provided. Substantially pure isolated calcium channels that contain at least one of the human calcium channel subunits are also provided. Substantially pure calcium channels that contain a mixture of one or more subunits encoded by the host cell and one or more subunits encoded by heterologous DNA or RNA that has been introduced into the cell are also provided. Substantially pure subtype- or tissue-type specific calcium channels are also provided.

In one embodiment, eukaryotic cells that contain heterologous DNA encoding at least one of $\alpha_1$ subunit of a calcium channel, preferably an $\alpha_{1F}$ subunit, that express the $\alpha_{1F}$ subunit and form functional homomeric human $\alpha_{1F}$-containing calcium channels are provided. These cells may be used to screen for compounds that modulate the activity of T-type channels and LVA type calcium channels.

In other embodiments, eukaryotic cells that contain heterologous DNA encoding at least one of an $\alpha_1$ subunit of a human calcium channel, an $\alpha_2$ subunit of a human calcium channel, a $\beta$ subunit of a human calcium channel and a $\gamma$ subunit of a human calcium channel are provided. In accordance with one preferred embodiment, the heterologous DNA is expressed in the eukaryotic cell and preferably encodes a human calcium channel $\alpha_1$ subunit.

Expression of Heterologous Calcium Channels: Electrophysiology and Pharmacology

Electrophysiological methods for measuring calcium channel activity are known to those of skill in the art and are exemplified herein. Any such methods may be used in order to detect the formation of functional calcium channels and to characterize the kinetics and other characteristics of the resulting currents. Pharmacological studies may be combined with the electrophysiological measurements in order to further characterize the calcium channels.

With respect to measurement of the activity of functional heterologous calcium channels, preferably, endogenous ion channel activity and, if desired, heterologous channel activity of channels that do not contain the desired subunits, of a host cell can be inhibited to a significant extent by chemical, pharmacological and electrophysiological means, including the use of differential holding potential, to increase the S/N ratio of the measured heterologous calcium channel activity.

Thus, various combinations of subunits encoded by the DNA provided herein are introduced into eukaryotic cells. The resulting cells can be examined to ascertain whether functional channels are expressed and to determine the properties of the channels. In particularly preferred aspects, the eukaryotic cell which contains the heterologous DNA expresses it and forms a recombinant functional calcium channel activity. In more preferred aspects, the recombinant calcium channel activity is readily detectable because it is a type that is absent from the untransfected host cell or is of a magnitude and/or pharmacological properties or exhibits biophysical properties not exhibited in the untransfected cell.

The eukaryotic cells can be transfected with various combinations of the subunit subtypes provided herein. The resulting cells will provide a uniform population of calcium channels for study of calcium channel activity and for use in the drug screening assays provided herein. Experiments that have been performed have demonstrated the inadequacy of prior classification schemes.

Preferred among transfected cells is a recombinant eukaryotic cell with a functional heterologous calcium channel. The recombinant cell can be produced by introduction of and expression of heterologous DNA or RNA transcripts encoding an $\alpha_1$ subunit of a human calcium channel as a homomer, more preferably also expressing, a heterologous DNA encoding a $\beta$ subunit of a human calcium channel and/or heterologous DNA encoding an $\alpha_2$ subunit of a human calcium channel. Especially preferred is the expression in such a recombinant cell of each of the $\alpha_1$, $\beta$ and $\alpha_2$ subunits encoded by such heterologous DNA or RNA transcripts, and optionally expression of heterologous DNA or an RNA transcript encoding a $\gamma$ subunit of a human calcium channel. The functional calcium channels may preferably include at least an $\alpha_1$ subunit and a $\beta$ subunit of a human calcium channel. Eukaryotic cells expressing these two subunits and also cells expressing additional subunits, have been prepared by transfection of DNA and by injection of RNA transcripts. Such cells have exhibited voltage-dependent calcium channel activity attributable to calcium channels that contain one or more of the heterologous human calcium channel subunits. For example, eukaryotic cells expressing heterologous calcium channels containing an $\alpha_2$ subunit in addition to the $\alpha_1$ subunit and a $\beta$ subunit have been shown to exhibit increased calcium selective ion flow across the cellular membrane in response to depolarization, indicating that the $\alpha_2$ subunit may potentiate calcium channel function. Cells that have been co-transfected with increasing ratios of $\alpha_2$ to $\alpha_1$ and the activity of the resulting calcium channels has been measured. The results indicate that increasing the amount of $\alpha_2$-encoding DNA relative to the other transfected subunits increases calcium channel activity.

Eukaryotic cells that express heterologous calcium channels containing a human $\alpha_1$ subunit as a homomer, particularly the $\alpha_{1F}$ subunit, or at least a human $\alpha_1$ subunit and optionally an $\alpha_2\delta$ subunit and/or a human $\beta$ subunit are preferred. Eukaryotic cells transformed with a composition containing DNA or an RNA transcript that encodes an $\alpha_1$ subunit alone or in combination with a $\beta$ and/or an $\alpha_2$ subunit may be used to produce cells that express functional calcium channels. Since recombinant cells expressing human calcium channels containing all of the human subunits encoded by the heterologous DNA or RNA are especially preferred, it is desirable to inject or transfect such host cells with a sufficient concentration of the subunit encoding nucleic acids to form calcium channels that contain the human subunits encoded by heterologous DNA or RNA. The precise amounts and ratios of DNA or RNA encoding the subunits may be empirically determined and optimized for a particular combination of subunits, cells and assay conditions.

In particular, mammalian cells have been transiently and stably transfected with DNA encoding one or more human calcium channel subunits. Such cells express heterologous calcium channels that exhibit pharmacological and electrophysiological properties that can be ascribed to human calcium channels. Such cells, however, represent homogeneous populations and the pharmacological and electrophysiological data provides insights into human calcium channel activity heretofore unattainable. For example, HEK cells that have been transiently transfected with DNA encoding the $\alpha_{1E-1}$, $\alpha_{2b}$, and $\beta_{1-3}$ subunits. The resulting cells transiently express these subunits, which form calcium channels that have properties that appear to be a pharmacologically distinct class of voltage-activated calcium channels distinct from those of L-, N-, T- and P-type channels. The observed $\alpha_{1E}$ currents were insensitive to drugs and toxins previously used to define other classes of voltage-activated calcium channels.

HEK cells that have been transiently transfected with DNA encoding $\alpha_{1B-1}$, $\alpha_{2b}$, and $\beta_{1-2}$ express heterologous calcium channels that exhibit sensitivity to $\omega$-conotoxin and currents typical of N-type channels. It has been found that alteration of the molar ratios of $\alpha_{1B-1}$, $\alpha_{2b}$ and $\beta_{1-2}$ introduced into the cells to achieve equivalent mRNA levels significantly increased the number of receptors per cell, the current density, and affected the $K_d$ for $\omega$-conotoxin.

The electrophysiological properties of these channels produced from $\alpha_{1B-1}$, $\alpha_{2b}$, and $\beta_{1-2}$ was compared with those of channels produced by transiently transfecting HEK cells with DNA encoding $\alpha_{1B\text{-}1}$, $\alpha_{2b}$ and $\beta_{1\text{-}3}$. The channels exhibited similar voltage dependence of activation, substantially identical voltage dependence, similar kinetics of activation and tail currents that could be fit by a single exponential. The voltage dependence of the kinetics of inactivation was significantly different at all voltages examined.

In certain embodiments, the eukaryotic cell with a heterologous calcium channel is produced by introducing into the cell a first composition, which contains at least one RNA transcript that is translated in the cell into a subunit of a human calcium channel. In preferred embodiments, the subunits that are translated include an $\alpha_1$ subunit of a human calcium channel. More preferably, the composition that is introduced contains an RNA transcript which encodes an $\alpha_1$ subunit of a human calcium channel and also contains (1) an RNA transcript which encodes a $\beta$ subunit of a human calcium channel and/or (2) an RNA transcript which encodes an $\alpha_2$ subunit of a human calcium channel. Especially preferred is the introduction of RNA encoding an $\alpha_1$, a $\beta$ and an $\alpha_2$ human calcium channel subunit, and, optionally, a $\gamma$ subunit of a human calcium channel. Methods for in vitro transcription of a cloned DNA and injection of the resulting RNA into eukaryotic cells are well known in the art. Transcripts of any of the full-length DNA encoding any of the subunits of a human calcium channel may be injected alone or in combination with other transcripts into eukaryotic cells for expression in the cells. Amphibian oocytes are particularly preferred for expression of in vitro transcripts of the human calcium channel subunit cDNA clones provided herein. Amphibian oocytes that express functional heterologous calcium channels have been produced by this method.

Assays and Clinical uses of the Cells and Calcium Channels
Assays
Assays for Identifying Compounds that Modulate Calcium Channel Activity Among the uses for eukaryotic cells which recombinantly express one or more subunits are assays for determining whether a test compound has calcium channel agonist or antagonist activity. These eukaryotic cells may also be used to select from among known calcium channel agonists and antagonists those exhibiting a particular calcium channel subtype specificity and to thereby select compounds that have potential as disease- or tissue-specific therapeutic agents.

In vitro methods for identifying compounds, such as calcium channel agonist and antagonists, that modulate the activity of calcium channels using eukaryotic cells that express heterologous human calcium channels are provided.

In particular, the assays use eukaryotic cells that express homomeric or heteromeric human calcium channel subunits encoded by heterologous DNA provided herein, for screening potential calcium channel agonists and antagonists which are specific for human calcium channels and particularly for screening for compounds that are specific for particular human calcium channel subtypes. Such assays may be used in conjunction with methods of rational drug design to select among agonists and antagonists, which differ slightly in structure, those particularly useful for modulating the activity of human calcium channels, and to design or select compounds that exhibit subtype- or tissue-specific calcium channel antagonist and agonist activities. These assays should accurately predict the relative therapeutic efficacy of a compound for the treatment of certain disorders in humans. In addition, since subtype-and tissue-specific calcium channel subunits are provided, cells with tissue-specific or subtype-specific recombinant calcium channels may be prepared and used in assays for identification of human calcium channel tissue- or subtype-specific drugs.

Desirably, the host cell for the expression of calcium channel subunits does not produce endogenous calcium channel subunits of the type or in an amount that substantially interferes with the detection of heterologous calcium channel subunits in ligand binding assays or detection of heterologous calcium channel function, such as generation of calcium current, in functional assays. Also, the host cells preferably should not produce endogenous calcium channels which detectably interact with compounds having, at physiological concentrations (generally nanomolar or picomolar concentrations), affinity for calcium channels that contain one or all of the human calcium channel subunits provided herein.

With respect to ligand binding assays for identifying a compound which has affinity for calcium channels, cells are employed which express, preferably, at least a heterologous $\alpha_1$ subunit. Transfected eukaryotic cells which express at least an $\alpha_1$ subunit may be used to determine the ability of a test compound to specifically bind to heterologous calcium channels by, for example, evaluating the ability of the test compound to inhibit the interaction of a labeled compound known to specifically interact with calcium channels. Such ligand binding assays may be performed on intact transfected cells or membranes prepared therefrom.

The capacity of a test compound to bind to or otherwise interact with membranes that contain heterologous calcium channels or subunits thereof, preferably $\alpha_{1F}$ subunit-containing calcium channels, may be determined by using any appropriate method, such as competitive binding analysis, such as Scatchard plots, in which the binding capacity of such membranes is determined in the presence and absence of one or more concentrations of a compound having known affinity for the calcium channel. Where necessary, the results may be compared to a control experiment designed in accordance with methods known to those of skill in the art. For example, as a negative control, the results may be compared to those of assays of an identically treated membrane preparation from host cells which have not been transfected with one or more subunit-encoding nucleic acids.

The assays involve contacting the cell membrane of a recombinant eukaryotic cell which expresses at least one subunit of a human calcium channel, preferably at least an $\alpha_1$ subunit of a human calcium channel, with a test compound and measuring the ability of the test compound to specifically bind to the membrane or alter or modulate the activity of a heterologous calcium channel on the membrane.

In preferred embodiments, the assay uses a recombinant cell that has a calcium channel containing an $\alpha_1$ subunit of a human calcium channel. In other preferred embodiments, the assay uses a recombinant cell that has a calcium channel containing an $\alpha_1$ subunit of a human calcium channel in combination with a $\beta$ subunit of a human calcium channel and/or an $\alpha_2$ subunit of a human calcium channel. Recombinant cells expressing heterologous calcium channels containing each of the $\alpha_1$ and optionally a $\beta$ and/or $\alpha_2$ human subunits, and, optionally, a $\gamma$ subunit of a human calcium channel are especially preferred for use in such assays.

In certain embodiments, the assays for identifying compounds that modulate calcium channel activity are practiced by measuring the calcium channel activity of a eukaryotic cell having a heterologous, functional calcium channel when such cell is exposed to a solution containing the test compound and a calcium channel-selective ion and comparing the measured calcium channel activity to the calcium channel activity of the same cell or a substantially identical control cell in a solution not containing the test compound. The cell is maintained in a solution having a concentration of calcium channel-selective ions sufficient to provide an inward current when the channels open. Recombinant cells expressing calcium channels that include each of the $\alpha_1$, $\beta$ and $\alpha_2$ human subunits, and, optionally, a $\gamma$ subunit of a human calcium channel, are especially preferred for use in such assays. Methods for practicing such assays are known to those of skill in the art. For example, for similar methods applied with *Xenopus laevis* oöcytes and acetylcholine receptors, see, Mishina et al. [(1985) Nature 313:364] and, with such oöcytes and sodium channels [see, Noda et al. (1986) *Nature* 322:826–828]. For similar studies which have been carried out with the acetylcholine receptor, see, e.g., Claudio et al. [(1987) *Science* 238:1688–1694]. Transcription based assays are also contemplated herein.

Functional recombinant or heterologous calcium channels may be identified by any method known to those of skill in the art. For example, electrophysiological procedures for measuring the current across an ion-selective membrane of a cell, which are well known, may be used. The amount and duration of the flow of calcium-selective ions through heterologous calcium channels of a recombinant cell containing DNA encoding one or more of the subunits provided herein has been measured using electrophysiological recordings using a two electrode and the whole-cell patch clamp techniques. In order to improve the sensitivity of the assays, known methods can be used to eliminate or reduce non-calcium currents and calcium currents resulting from endogenous calcium channels, when measuring calcium currents through recombinant channels. For example, the DHP Bay K 8644 specifically enhances L-type calcium channel function by increasing the duration of the open state of the channels [see, e.g., Hess, J. B., et al. (1984) *Nature* 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of test compounds, including compounds having unknown activity, for calcium channel agonist or antagonist activity to determine if the test compound potentiates, inhibits or otherwise alters the flow of calcium ions or other ions through a human calcium channel can be accomplished by (a) maintaining a eukaryotic cell which is transfected or injected to express a heterologous functional calcium channel capable of regulating the flow of calcium channel-selective ions into the cell in a medium containing calcium channel-selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel-selective ions; and (d) comparing the amount and duration of current flow into the cell in the presence of the test compound to that of the current flow into the cell, or a substantially similar cell, in the absence of the test compound.

The assays thus use cells, provided herein, that express heterologous functional calcium channels and measure functionally, such as electrophysiologically, the ability of a test compound to potentiate, antagonize or otherwise modulate the magnitude and duration of the flow of calcium channel-selective ions, such as $Ca^{2+}$ or $Ba^{2+}$, through the heterologous functional channel. The amount of current which flows through the recombinant calcium channels of a cell may be determined directly, such as electrophysiologically, or by monitoring an independent reaction which occurs intracellularly and which is directly influenced in a calcium (or other) ion dependent manner. Any method for assessing the activity of a calcium channel may be used in conjunction with the cells and assays provided herein. For example, in one embodiment of the method for testing a compound for its ability to modulate calcium channel activity, the amount of current is measured by its modulation of a reaction which is sensitive to calcium channel-selective ions and uses a eukaryotic cell which expresses a heterologous calcium channel and also contains a transcriptional control element operatively linked for expression to a structural gene that encodes an indicator protein. The transcriptional control element used for transcription of the indicator gene is responsive in the cell to a calcium channel-selective ion, such as $Ca^{2+}$ and $Ba^{2+}$. The details of such transcriptional based assays are described in commonly owned PCT International Patent Application No. PCT/US91/5625, filed Aug. 7, 1991, which claims priority to copending commonly owned allowed U.S. application Ser. No. 07/563,751, filed Aug. 7, 1990; see also, commonly owned published PCT International Patent Application PCT US92/11090, which corresponds to co-pending U.S. applications Ser. Nos. 08/229,150 and 08/244,985. The contents of these applications are herein incorporated by reference thereto.

Assays for Diagnosis of LES

LES is an autoimmune disease characterized by an insufficient release of acetylcholine from motor nerve terminals which normally are responsive to nerve impulses. Immunoglobulins (IgG) from LES patients block individual voltage-dependent calcium channels and thus inhibit calcium channel activity [Kim and Neher, *Science* 239:405–408 (1988)]. A diagnostic assay for Lambert Eaton Syndrome (LES) is provided herein. The diagnostic assay for LES relies on the immunological reactivity of LES IgG with the human calcium channels or particular subunits alone or in combination or expressed on the surface of recombinant cells. For example, such an assay may be based on immunoprecipitation of LES IgG by the human calcium channel subunits and cells that express such subunits provided herein.

Clinical applications

In relation to therapeutic treatment of various disease states, the availability of DNA encoding human calcium channel subunits permits identification of any alterations in such genes (e.g., mutations) which may correlate with the occurrence of certain disease states. In addition, the creation of animal models of such disease states becomes possible, by specifically introducing such mutations into synthetic DNA fragments that can then be introduced into laboratory animals or in vitro assay systems to determine the effects thereof.

Also, genetic screening can be carried out using the nucleotide sequences as probes. Thus, nucleic acid samples from subjects having pathological conditions suspected of involving alteration/modification of any one or more of the calcium channel subunits can be screened with appropriate probes to determine if any abnormalities exist with respect to any of the endogenous calcium channels. Similarly, subjects having a family history of disease states related to calcium channel dysfunction can be screened to determine if they are also predisposed to such disease states.

EXAMPLES

The following examples are included for illustrative purposes only and are not intended to limit the scope of the invention.

Example I

PREPARATION OF LIBRARIES USED FOR ISOLATION OF DNA ENCODING HUMAN VOLTAGE-DEPENDENT CALCIUM CHANNEL SUBUNITS

A. RNA Isolation

1. IMR32 cells

IMR32 cells were obtained from the American Type Culture Collection (ATCC Accession No. CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H.C. Birnboim [(1988) *Nucleic Acids Research* 16:1487–1497]. Poly(A$^+$) RNA was selected according to standard procedures [see, e.g., Sambrook et al. (1 989) *Molecular Cloning, A Laboratory Manual*, Cold Spring Harbor Laboratory Press; pg. 7.26–7.29].

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5 M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7 M CsCl, 0.1 M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25 M NaCl and two volumes of 95% ethanol.

The precipitate was collected by centrifugation and resuspended in 4 ml PK buffer (0.05 M TRIS, pH 8.4, 0.14 M NaCl, 0.01 M EDTA, 1% SDS). Proteinase K was added to the sample to a final concentration of 200 µg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 µl of ETS buffer. The yield of total RNA was approximately 1.0 mg. Poly A$^+$ RNA (30 µg) was isolated from the total RNA according to standard methods as stated in Example I.A.1.

B. Library Construction

Double-stranded cDNA was synthesized according to standard methods [see, e.g., Sambrook et al. (1989) IN: *Molecular Cloning, A Laboratory Manual*, Cold Spring Harbor Laboratory Press, Chapter 8]. Each library was prepared in substantially the same manner except for differences in: 1) the oligonucleotide used to prime the first strand cDNA synthesis, 2) the adapters that were attached to the double-stranded cDNA, 3) the method used to remove the free or unused adapters, and 4) the size of the fractionated cDNA ligated into the λ phage vector.

1. IMR32 cDNA library #1

Single-stranded cDNA was synthesized using IMR32 poly(A$^+$) RNA (Example I.A.1.) as a template and was primed using oligo (dT)$_{12-18}$ (Collaborative Research Inc., Bedford, Mass.). The single-stranded cDNA was converted to double-stranded cDNA and the yield was approximately 2 µg. EcoI adapters:

5'-AATTCGGTACGTACACTCGAGC-3'=22-mer (SEQ ID No.15)

3'-GCCATGCATGTGAGCTCG-5'=18-mer (SEQ ID No.16)

also containing SnaBI and XhoI restriction sites were then added to the double-stranded cDNA according to the following procedure.

a. Phosphorylation of 18-mer

The 18-mer was phosphorylated using standard methods [see, e.g., Sambrook et al. (1989) IN: *Molecular Cloning, A Laboratory Manual*, Cold Spring Harbor Laboratory Press, Chapter 8] by combining in a 10 µl total volume the 18-mer (225 pmoles) with [$^{32}$P]γ-ATP (7000 Ci/mmole; 1.0 µl) and kinase (2 U) and incubating at 37° C. for 15 minutes. After incubation, 1 µl 10 mM ATP and an additional 2 U of kinase were added and incubated at 37° C. for 15 minutes. Kinase was then inactivated by boiling for 10 minutes.

b. Hybridization of 22-mer

The 22-mer was hybridized to the phosphorylated 18-mer by addition of 225 pmoles of the 22-mer (plus water to bring volume to 15 µl), and incubation at 65° C. for 5 minutes. The reaction was then allowed to slow cool to room temperature.

The adapters were thus present at a concentration of 15 pmoles/µl, and were ready for cDNA-adapter ligation.

c. Ligation of Adapters to cDNA

After the EcoRI, SnaBI, XhoI adapters were ligated to the double-stranded cDNA using a standard protocol [see, e.g., Sambrook et al. (1989) IN: *Molecular Cloning, A Laboratory Manual*, Cold Spring Harbor Laboratory Press, Chapter 8], the ligase was inactivated by heating the mixture to 72° C. for 15 minutes. The following reagents were added to the cDNA ligation reaction and heated at 37° C. for 30 minutes: cDNA ligation reaction (20 µl), water (24 µl), 10× kinase buffer (3 µl), 10 mM ATP (1 µl) and kinase (2 µl of 2 U/µl). The reaction was stopped by the addition of 2 µl 0.5M EDTA, followed by one phenol/chloroform extraction and one chloroform extraction.

d. Size Selection and Packaging of cDNA

The double-stranded cDNA with the EcoRI, SnaBI, XhoI adapters ligated was purified away from the free or unligated adapters using a 5 ml Sepharose CL-4B column (Sigma, St.

Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λgt11 in a 5 μl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA library #2

This library was prepared as described (Example I.B.1.) with the exception that 3 to 9 kb cDNA fragments were ligated into the λgt11 phage vector rather than the 1 to 3 kb fragments.

3. IMR32 cDNA library #3

IMR32 cell poly(A$^+$) RNA (Example I.A.1.) was used as a template to synthesize single-stranded cDNA. The primers for the first strand cDNA synthesis were random primers (hexadeoxy-nucleotides [pd(N)$_6$] Cat #5020-1, Clontech, Palo Alto, Calif.). The double-stranded cDNA was synthesized, EcoRI, SnaBI, XhoI adapters were added to the cDNA, the unligated adapters were removed, and the double-stranded cDNA with the ligated adapters was fractionated on an agarose gel, as described in Example I.B.1. The cDNA fraction greater than 1.8 kb was eluted from the agarose, ligated into λgt11, packaged, and plated into a bacterial lawn of Y1088 (as described in Example I.B.1.).

4. IMR32 cDNA library #4

IMR32 cell poly(A$^+$) RNA (Example I.A.1.) was used as a template to synthesize single-stranded cDNA. The primers for the first strand cDNA synthesis were oligonucleotides: 89–365a specific for the $\alpha_{1D}$ (VDCC III) type $\alpha_1$-subunit (see Example II.A.) coding sequence (the complementary sequence of nt 2927 to 2956, SEQ ID No. 1), 89–495 specific for the $\alpha_{1C}$ (VDCC II) type $\alpha_1$-subunit (see Example II.B.) coding sequence (the complementary sequence of nt 852 to 873, SEQ ID No. 3), and 90–12 specific for the $\alpha_{1C}$-subunit coding sequence (the complementary sequence of nt 2496 to 2520, SEQ ID No. 3). The cDNA library was then constructed as described (Example I.B.3), except that the cDNA size-fraction greater than 1.5 kb was eluted from the agarose rather than the greater than 1.8 kb fraction.

5. IMR32 cDNA library #5

The cDNA library was constructed as described (Example I.B.3.) with the exception that the size-fraction greater than 1.2 kb was eluted from the agarose rather than the greater than 1.8 kb fraction.

6. Human thalamus cDNA library #6

Human thalamus poly (A$^+$) RNA (Example I.A.2.) was used as a template to synthesize single-stranded cDNA. Oligo (dT) was used to prime the first strand synthesis (Example I.B.1.). The double-stranded cDNA was synthesized (Example I.B.1.) and EcoRI, KpnI, NcoI adapters of the following sequence:

5' CCATGGTACCTTCGTTGACG 3'=20-mer (SEQ ID NO. 17)

3' GGTACCATGGAAGCAACTGCTTAA 5'=24-mer (SEQ ID NO. 18)

were ligated to the double-stranded cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [hybridization: 50% deionized formamide, 200 μg/ml sonicated herring sperm DNA (Cat #223646, Boehringer Mannheim Biochemicals, Indianapolis, Ind.), 5×SSPE, 5×Denhardt's, 42° C.; wash :0.2×SSPE, 0.1% SDS, 65° C.]. The recipes for SSPE and Denhardt's and the preparation of deionized formamide are described, for example, in Sambrook et al. (1989) *Molecular Cloning, A Laboratory Manual*, Cold Spring Harbor Laboratory Press, Chapter 8). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

It is understood that equivalent stringencies may be achieved using alternative buffers, salts and temperatures.

Example II

ISOLATION OF DNA ENCODING THE HUMAN CALCIUM CHANNEL $\alpha_{1F}$ SUBUNIT

A. RNA Isolation

Human medullary thyroid carcinoma cells (TT cells; ATCC Accession No. CRL1803) were grown in DMEM medium supplemented with 10% fetal calf serum at 37° C. in 5% CO$_2$ atmosphere and total cytoplasmic RNA was isolated from forty 10 cm plates using a "midi-prep" RNA isolation kit (Qiagen) as per the manufacturer's instructions. The protocol entails the use of the detergent NP40 which lyses the cell membrane under mild conditions such that the nuclear membrane remains intact thereby eliminating incompletely spliced RNA transcripts from the preparation.

PolyA+RNA was isolated from total cytoplasmic RNA using two passes over an oligo(dT)-cellulose column. Briefly, 2–3 mg of total cytoplasmic RNA was resuspended in NETS buffer (500 mM NaCl 10 mM EDTA, 10 mM Tris, pH 7.4, 0.2% SDS) and passed slowly over a column containing 0.5 g of oligo(dT)-cellulose (Collaborative Research) equilibrated in NETS buffer. The column was washed with 30 mls of NETS buffer and polyA+RNA was eluted using about 3 mls of ETS buffer (10 mM EDTA, 10 mM Tris, pH 7.4, 0.2% SDS). The ionic strength of the polyA+RNA-containing buffer was adjusted to 500 mM NaCl and passed over a second oligo(dT)-cellulose column essentially as described above. Following elution from the second column, the polyA+RNA was precipitated twice in ethanol and resuspended in H$_2$O.

B. Library Construction

Double stranded cDNA (dscDNA) was synthesized according to standard methods [Gubler et al. (1985) *Gene* 25:263–269; Lapeyre et al. (1985) *Gene* 37:215–220]. Briefly, first strand cDNA synthesis was initiated using TT cell polyA+RNA as a template and using random primers and Moloney Murine Leukemia Virus reverse transcriptase (MMLV-RT). The second strand was synthesized using a combination of *E. coli* DNA polymerase, *E. coli* DNA ligase and RNase H.

Regions of single stranded DNA were converted to double-stranded DNA using T4 DNA polymerase generating blunt-ended double stranded fragments. EcoRI restriction endonuclease site adapters:

5' CGTGCACGTCACGCTAG 3' (SEQ ID NO. 39)

3' GCACGTGCAGTGCGATCTTAA 5' (SEQ ID NO. 40)

were ligated to the double-stranded cDNA using a standard protocol [see, e.g., Sambrook et al. (1989) IN: *Molecular Cloning, A Laboratory Manual*, Cold Spring Harbor Laboratory Press, Chapter 8]. The double-stranded cDNA with the EcoRI adapters ligated was purified away from the free or unligated adapters by column chromatography using Sepharose CL-4B resin followed by size selection of the cDNA on a 1.2% agarose gel. After visualizing the resolved DNA using ethidium bromide, two fractions of cDNA, >3.5 kb and 1.0–3.5 kb, were isolated from the gel and inserted into the vector λgt10.

The ligated λgt10 containing the cDNA insert was packaged into λ phage virions in vitro using the Gigapack III Gold packaging (Stratagene, La Jolla, Calif.) kit. Using this method, phage libraries of ~1.5×10$^6$ recombinants for cDNA>3.5 kb fraction and ~10×10$^6$ recombinants for DNA fraction between 1.0 and 3.5 kB were obtained.

C. Isolation of DNA Encoding a Portion of Human $\alpha_1$ Calcium Channel Subunits DNA encoding a small region of human $\alpha_1$ subunits encoded in TT cells was isolated using degenerate PCR-based amplification (e.g., see Williams et al. (1994) *J. Biol. Chem.* 269:22347–22357). These amplified DNAs were used to generate DNA probes for the isolation of DNA encoding a full-length human $\alpha_{1F}$ calcium channel subunit.

Two sets of degenerate oligonucleotides were synthesized based on the flanking regions of the II–III loop known to share a high degree of sequence identity amongst known human $\alpha_1$ calcium channel subunits: 1) two degenerate oligonucleotides complementary to the regions of the IIS5–IIS6 loop were synthesized as 5' upstream primers (SEQ ID NOs. 41 & 42); and 2) two degenerate oligonucleotides complementary to a portion of the IIIS5 transmembrane segment were synthesized as 3' downstream primers (SEQ ID NOs. 43 & 44).

These degenerate oligonucleotides were used as primer pairs in nested PCR amplification reactions using Pfu DNA polymerase (Stratagene, La Jolla, Calif.) and reactions were performed according to the manfacturer's instructions. Samples were placed in a commercially available thermocycler (Perkin-Elmer) and the amplification reactions were set as follows: 1 cycle, 5 min @ 95° C.; 5 cycles, 20 sec @ 95° C./20 sec @ 42° C./2.5 min @ 72° C.; 30 cycles, 20 sec @ 95° C./20 sec @ 50° C./2.5 min @ 72° C.; and 1 cycle, 7 min @ 72° C. Amplified DNA products were subjected to electrophoresis on an agarose gel and gel purified using standard methods.

D. Amplification of DNA Encoding a Portion of Human $\alpha_{1F}$ Calcium Channel Subunit To amplify DNA encoding a portion of human $\alpha_{1F}$ calcium channel subunit, three degenerate oligonucleotides (SEQ ID NOs. 45–47) that share partial complementarity to a region of Domain III were synthesized as 5' primers. This region is encompassed within all of the amplified $\alpha_1$-encoding fragments of Section C above. Two oligonucleotides based on sequences in IIIS2 (SEQ ID NOs. 45 & 47) were used as 5' primers in conjunction with the 3'IIIS5 transmembrane primers used in the initial PCR reactions (SEQ ID NOs. 43 & 44) to amplify DNA encoding a portion of the human $\alpha_1$ subunit using the amplified products as templates.

The amplified DNA products were subcloned into the pCR-Blunt vector (Invitrogen), plasmid DNA was purified from isolated transformants and the DNA sequence of each insert was determined. A 340 bp fragment (SEQ ID NO. 48; nt 4271 to 4610 of SEQ ID NO. 49) was identified that shares approximately 55–60% sequence identity to known human $\alpha_1$ calcium channel subunits. This DNA fragment, designated PCR1, was used DNA probe to isolate DNA encoding a human $\alpha_{1F}$ calcium channels subunit.

E. Isolation of DNA Encoding a Human $\alpha_{1F}$ Calcium Channel Subunit and Construction of DNA Encoding a Full-length $\alpha_{1F}$ Subunit 1. Reference list of partial human $\alpha_{1F}$ clones The full-length $\alpha_{1F}$ cDNA sequence is set forth in SEQ ID NO. 49. A list of partial cDNA clones used to characterize the $\alpha_{1F}$ sequence and the nucleotide position of each clone relative to the full-length $\alpha_{1F}$ cDNA sequence is shown below. The isolation and characterization of these clones are described below.

1.305 nt 1 to 3530 of SEQ ID No. 49
1.205 nt 2432 to 4658 of SEQ ID No. 49
1.204 nt 3154 to 5699 of SEQ ID NO. 49
PCR1 nt 4271 to 4610 of SEQ ID NO. 49
1.202 nt 4372 to 5476 of SEQ ID No. 49
1.203 nt 3891 to 7898 of SEQ ID No. 49

2. Isolation and characterization of individual clones

Approximately 1.5×10$^5$ recombinants of the TT cell phage library containing inserts >3.5 kb were plated and duplicate lifts prepared from each plate. The lifts were probed with radiolabelled PCR1 using standard hybridization conditions, the filters were washed and approximately 100 positive plaques were identified. Initially, 5 positives, λ1.201–λ1.205, were selected for plaque purification and characterization.

Restriction endonuclease digestion of purified DNA isolated from λ1.201–λ1.205 with EcoRI indicated that clone 1.201 contains the original insert of ~350bp PCR1 fragment, whereas clones 1.202, 1.203, 1.204 and 1.205 contain inserts of ~1100, ~4000, ~2600 and ~2200 nt, respectively.

DNA sequencing of each insert revealed that clone 1.202 contains 1,105 bp insert corresponding to nt 4372 to 5476 of SEQ ID No. 49; clone 1.203 contains 4,008 bp insert corresponding to nt 3891 to 7898 of SEQ ID No. 49; clone 1.204 contains 2,546 bp insert corresponding to nt 3154 to 5699 of SEQ ID NO. 49; and clone 1.205 contains 2,227 bp insert corresponding to nt 2432 to 4658 of SEQ ID No. 49. These four DNA clones contain overlapping sequences that encode an open reading frame of approximately 6.6 kb that encodes a majority of the $\alpha_{1F}$ subunit, including the entire carboxy terminus and the in-frame translational stop codon.

DNA encoding the 5'-end of the human $\alpha_{1F}$ calcium channel subunit was isolated using a 548 bp EcoRI-NcoI restriction endonuclease fragment from the 5'-end of clone 1.205 (nt 2432 to nt 2979 SEQ ID No. 49) to rescreen the TT cell cDNA library under high stringency conditions. Briefly, DNA encoding the amino terminus of human $\alpha_{1F}$ calcium containing inserts of >3.5 kb was incubated with the purified restriction fragment and hybridized at 42° C. and washed under high stringency conditions as described above in EXAMPLE 1C.

One recombinant, clone 1.305, was identified that contains a 3,530 nucleotide insert that shares at its 3' end approximately 1.1 kb of sequence identity with the 5'-end of clone 1.205 (~nt 2432 to nt 3530 SEQ ID No. 49) and also contains 2.4 kb of sequence upstream of the EcoRI site located at the 5'-end of clone 1.205 (nt 2433 to 2438 SEQ ID No. 49). This sequence encodes the ATG initiation codon (nt 249 to nt 251 SEQ ID No. 49) and 1,094 amino acids of the amino terminus of the $\alpha_{1F}$ subunit as well as 248 bp of 5'-untranslated sequence, including a consensus ribosome binding site (nt 244 to nt 248 of SEQ ID No. 49).

Two other recombinants were also identified (SEQ ID NOs. 51 & 52) that share approximately 1.1 kb of sequence identity with the 3'-end of clone 1.305 but differ in the length of the DNA sequence corresponding to the extended intracellular loop located between transmembrane Domains I and II.

3. Construction of a full-length $\alpha_{1F}$-encoding DNA clone

Portions of these partial cDNA clones can be ligated to generate a full-length $\alpha_{1F}$ cDNA using common restriction endonuclease sites shared amongst the $\alpha_{1F}$-encoding fragments. For example, the construction of a full-length $\alpha_{1F}$ cDNA can be prepared in two steps as described in detail below: 1) DNA encoding the 5'-end of $\alpha_{1F}$ present in clone 1.305 can be combined with clone 1.205 using a common EcoRI site (nt 2433 to 2438 SEQ ID No. 49); and 2) the DNA of step 1) encoding the amino terminus of $\alpha_{1F}$ can be combined with the carboxyl terminal sequences of $\alpha_{1F}$ encoded in clone 1.203 using the common EcoRV restriction endonuclease site shared between clone 1.205 and 1.203 (nt 4517–4522 of SEQ ID NO. 49). The resulting full-length human $\alpha_{1F}$ calcium channel subunit is 2,353 amino acid residues in length (SEQ ID NO. 50).

Example III

RECOMBINANT EXPRESSION OF HUMAN NEURONAL CALCIUM CHANNEL SUBUNIT-ENCODING cDNA AND RNA TRANSCRIPTS IN MAMMALIAN CELLS

The methods and assays described in this example, may be employed using the DNA encoding an $\alpha_{1F}$ subunit in place of the $\alpha_1$ subunits exemplified below. Of particular interest are cells that express the $\alpha_{1F}$ subunit alone or in combination with selected $\alpha_2$ subunits.

A. Recombinant Expression of the Human Neuronal Calcium Channel $\alpha_2$ subunit cDNA in DG44 Cells 1. Stable transfection of DG44 cells DG44 cells [dhfr Chinese hamster ovary cells; see, e.g., Urlaub, G. et al. (1986) *Som. Cell Molec. Genet.* 12:555–566] obtained from Lawrence Chasin at Columbia University were stably transfected by $CaPO_4$ precipitation methods [Wigler et al. (1979) *Proc. Natl. Acad. Sci. USA* 76:1373–1376] with pSV2dhfr vector containing the human neuronal calcium channel $\alpha_2$-subunit cDNA for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$ subunit cDNA expression in transfected DG44 cells

Total RNA was extracted according to the method of Birnboim [(1988) *Nuc. Acids Res.* 16:1487–1497] from four of the DG44 cell lines that had been stably transfected with pSV2dhfr containing the human neuronal calcium channel $\alpha_2$ subunit cDNA. RNA (~15 µg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5×Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$ subunit cDNA revealed that one of the four cell lines contained hybridizing mRNA the size expected for the transcript of the $\alpha_2$ subunit cDNA (5000 nt based on the size of the cDNA) when grown in the presence of 10 mM sodium butyrate for two days. Butyrate nonspecifically induces transcription and is often used for inducing the SV40 early promoter [Gorman, C. and Howard, B. (1983) *Nucleic Acids Res.* 11:1631]. This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$ subunit coding sequence and therefore should yield a full-length $\alpha_2$ subunit protein. A weakly hybridizing 8000-nucleotide transcript was present in untransfected and transfected DG44 cells. Apparently, DG44 cells transcribe a calcium channel $\alpha_2$ subunit or similar gene at low levels. The level of expression of this endogenous $\alpha_2$ subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$ subunit cDNA. Approximately $10^7$ cells were sonicated in 300 µl of a solution containing 50 mM HEPES, 1 mM EDTA, 1 mM PMSF. An equal volume of 2× loading dye [Laemmli, U.K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha_2$ subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$ subunit of the human neuronal calcium channel (130–150 kDa). The level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110 kD immunoreactive protein that may be either a product of proteolytic degradation of the full-length $\alpha_2$ subunit or a product of translation of one of the shorter (<5000 nt) mRNAs produced in this cell line that hybridized to the $\alpha_2$ subunit cDNA probe.

B. Expression of DNA Encoding Human Neuronal Calcium Channel $\alpha_1$, $\alpha_2$ and $\beta_1$ Subunits in HEK Cells Human embryonic kidney cells (HEK 293 cells) were transiently and stably transfected with human neuronal DNA encoding calcium channel subunits. Individual transfectants were analyzed electrophysiologically for the presence of voltage-activated barium currents and functional recombinant voltage-dependent calcium channels were analyzed.

1. Transfection of HEK 293 cells

Separate expression vectors containing DNA encoding human neuronal calcium channel $\alpha_{1D}$, $\alpha_2$ and $\beta_1$ subunits, plasmids pVDCCIII(A), pHBCaCH$\alpha_2$A, and pHBCaCH$\beta_{1a}$RBS(A), respectively, were constructed as described in International PCT application No. PCT/US94/09230, see, also allowed U.S. application Ser. No. 08/149,097. These three vectors were used to transiently co-transfect HEK 293 cells. For stable transfection of HEK 293 cells, vector pHBCaCH$\beta_{1b}$RBS(A) was used in place of pHBCaCH$\beta_{1a}$RBS(A) to introduce the DNA encoding the $\beta_1$ subunit into the cells along with pVDCCIII(A) and pHBCaCH$\alpha_2$A.

a. Transient Transfection

Expression vectors pVDCCIII(A), pHBCaCH$\alpha_2$A and pHBCaCH$\beta_{1a}$RBS(A) were used in two sets of transient transfections of HEK 293 cells (ATCC Accession No. CRL1573). In one transfection procedure, HEK 293 cells were transiently cotransfected with the $\alpha_1$ subunit cDNA expression plasmid, the $\alpha_2$ subunit cDNA expression plasmid, the $\beta_1$ subunit cDNA expression plasmid and plasmid pCMVβgal (Clontech Laboratories, Palo Alto, Calif.). Plasmid pCMVβgal contains the lacZ gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$ subunit cDNA expression plasmid pVDCCIII(A) and pCMVβgal. In both transfections, $2-4\times10^6$ HEK 293 cells in a 10-cm tissue culture plate were transiently co-transfected with 5 μg of each of the plasmids included in the experiment according to standard $CaPO_4$ precipitation transfecfion procedures (Wigler et al. (1979) *Proc. Natl. Acad. Sci. USA* 76:1373–1376). The transfectants were analyzed for β-galactosidase expression by direct staining of the product of a reaction involving β-galactosidase and the X-gal substrate [Jones, J. R. (1986) *EMBO* 5:3133–3142] and by measurement of β-galactosidase activity [Miller, J. H. (1972) Experiments in Molecular Genetics, pp.352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable Transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 μg pVDCCIII(A), 5 μg pHBCaCH$\alpha_2$A, 5 μg pHBCaCH$\beta_{1b}$RBS(A), 5 μg pCMVBgal and 1 μg pSV2neo (as a selectable marker). After 10–20 days of growth in media containing 500 μg G418, colonies had formed and were isolated using cloning cylinders.

2. Analysis of HEK 293 cells transiently transfected with DNA encoding human neuronal calcium channel subunits a. Analysis of β-galactosidase Expression Transient transfectants were assayed for β-galactosidase expression by β-galactosidase activity assays (Miller, J. H., (1972) Experiments in Molecular Genetics, pp. 352–355, Cold Spring Harbor Press) of cell lysates (prepared as described in International PCT application No. PCT/US94/09230, see, also allowed U.S. application Ser. No. 08/149, 097.) and staining of fixed cells (Jones, J. R. (1986) EMBO 5:3133–3142). The results of these assays indicated that approximately 30% of the HEK 293 cells had been transfected.

b. Northern Analysis

PolyA+RNA was isolated using the Invitrogen Fast Trak Kit (InVitrogen, San Diego, Calif.) from HEK 293 cells transiently transfected with DNA encoding each of the $\alpha_1$, $\alpha_2$ and $\beta_1$ subunits and the lacZ gene or the $\alpha_1$ subunit and the lacZ gene. The RNA was subjected to electrophoresis on an agarose gel and transferred to nitrocellulose. The nitrocellulose was then hybridized with one or more of the following radiolabeled probes: the lacZ gene, human neuronal calcium channel $\alpha_{1D}$ subunit-encoding cDNA, human neuronal calcium channel $\alpha_2$ subunit-encoding cDNA or human neuronal calcium channel $\beta_1$ subunit-encoding cDNA. Two transcripts that hybridized with the $\alpha_1$ subunit-encoding cDNA were detected in HEK 293 cells transfected with the DNA encoding the $\alpha_1$, $\alpha_2$, and $\beta_1$ subunits and the lacZ gene as well as in HEK 293 cells transfected with the $\alpha_1$ subunit cDNA and the lacZ gene. One mRNA species was the size expected for the transcript of the $\alpha_1$ subunit cDNA (8000 nucleotides). The second RNA species was smaller (4000 nucleotides) than the size expected for this transcript. RNA of the size expected for the transcript of the lacZ gene was detected in cells transfected with the $\alpha_1$, $\alpha_2$ and $\beta_1$ subunit-encoding cDNA and the lacZ gene and in cells transfected with the $\alpha_1$ subunit cDNA and the lacZ gene by hybridization to the lacZ gene sequence.

RNA from cells transfected with the $\alpha_1$, $\alpha_2$ and $\beta_1$ subunit-encoding cDNA and the lacZ gene was also hybridized with the $\alpha_2$ and $\beta_1$ subunit cDNA probes. Two mRNA species hybridized to the $\alpha_2$ subunit cDNA probe. One species was the size expected for the transcript of the $\alpha_2$ subunit cDNA (4000 nucleotides). The other species was larger (6000 nucleotides) than the expected size of this transcript. Multiple RNA species in the cells co-transfected with $\alpha_1$, $\alpha_2$ and $\beta_1$ subunit-encoding cDNA and the lacZ gene hybridized to the $\beta_1$ subunit cDNA probe. Multiple β subunit transcripts of varying sizes were produced since the β subunit cDNA expression vector contains two potential polyA$^+$ addition sites.

c. Electrophysiological Analysis

Individual transiently transfected HEK 293 cells were assayed for the presence of voltage-dependent barium currents using the whole-cell variant of the patch clamp technique [Hamill et al. (1981). *Pflugers Arch.* 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio.) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 $\mu$M in 15 mM $Ba^{2+}$-containing bath solution before they were applied.

Twenty-one negative control HEK 293 cells (transiently transfected with the lacZ gene expression vector pCMV$\beta$gal only) were analyzed by the whole-cell variant of the patch clamp method for recording currents. Only one cell displayed a discernable inward barium current; this current was not affected by the presence of 1 $\mu$M Bay K 8644. In addition, application of Bay K 8644 to four cells that did not display $Ba^{2+}$ currents did not result in the appearance of any currents.

Two days after transient transfection of HEK 293 cells with $\alpha_1$, $\alpha_2$ and $\beta_1$ subunit-encoding cDNA and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Inward barium currents were detected in two of these nine transfectants. In these assays, the holding potential of the membrane was −90 mV. The membrane was depolarized in a series of voltage steps to different test potentials and the current in the presence and absence of 1 $\mu$M Bay K 8644 was recorded. The inward barium current was significantly enhanced in magnitude by the addition of Bay K 8644. The largest inward barium current (~160 pA) was recorded when the membrane was depolarized to 0 mV in the presence of 1 $\mu$M Bay K 8644. A comparison of the I–V curves, generated by plotting the largest current recorded after each depolarization versus the depolarization voltage, corresponding to recordings conducted in the absence and presence of Bay K 8644 illustrated the enhancement of the voltage-activated current in the presence of Bay K 8644.

Pronounced tail currents were detected in the tracings of currents generated in the presence of Bay K 8644 in HEK 293 cells transfected with $\alpha_1$, $\alpha_2$ and $\beta_1$ subunit-encoding cDNA and the lacZ gene, indicating that the recombinant calcium channels responsible for the voltage-activated barium currents recorded in this transfected appear to be DHP-sensitive.

The second of the two transfected cells that displayed inward barium currents expressed a ~50 pA current when the membrane was depolarized from −90 mV. This current was nearly completely blocked by 200 $\mu$M cadmium, an established calcium channel blocker.

Ten cells that were transiently transfected with the DNA encoding the $\alpha_1$ subunit and the lacZ gene were analyzed by whole-cell patch clamp methods two days after transfection. One of these cells displayed a 30 pA inward barium current. This current amplified 2-fold in the presence of 1 $\mu$M Bay K 8644. Furthermore, small tail currents were detected in the presence of Bay K 8644. These data indicate that expression of the human neuronal calcium channel $\alpha_{1D}$ subunit-encoding cDNA in HEK 293 yields a functional DHP-sensitive calcium channel.

3. Analysis of HEK 293 cells stably transfected with DNA encoding human neuronal calcium channel subunits Individual stably transfected HEK 293 cells were assayed electrophysiologically for the presence of voltage-dependent barium currents as described for electrophysiological analysis of transiently transfected HEK 293 cells (International PCT application No. PCT/US94/09230, see, also allowed U.S. application Ser. No. 08/149,097). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 $\mu$M) was added to the pipet solution and forskolin (10 $\mu$M) was added to the bath solution in some of the recordings. Qualitatively similar results were obtained whether these compounds were present or not.

Barium currents were recorded from stably transfected cells in the absence and presence of Bay K 8644 (1 $\mu$M). When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The peak magnitude of currents recorded from this same cell as a function of a series of depolarizing voltages were assessed. The responses in the presence of Bay K 8644 not only increased, but the entire current-voltage relation shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-based Vectors and pcDNA1-based Vectors for Expression of DNA Encoding Human Neuronal Calcium Channel Subunits 1. Preparation of constructs Additional expression vectors were constructed using pCMV. The full-length $\alpha_{1D}$ cDNA from pVDCCIII(A) (see International PCT application No. PCT/US94/09230, see, also allowed U.S. application Ser. No. 08/149,097), the full-length $\alpha_2$ cDNA, contained on a 3600 bp EcoRI fragment from HBCaCH$\alpha_2$ (International PCT application No. PCT/US94/09230, see, also allowed U.S. application Ser. No. 08/149,097.) and a full-length $\beta_1$ subunit cDNA from pHBCaCH$\beta_{1b}$RBS(A) (see International PCT application No. PCT/US94/09230, see, also allowed U.S. application Ser. No. 08/149,097) were separately subcloned into plasmid pCMV$\beta$gal. Plasmid pCMV$\beta$gal was digested with NotI to remove the lacZ gene. The remaining vector portion of the plasmid, referred to as pCMV, was blunt-ended at the NotI sites. The full-length $\alpha_2$-encoding DNA and $\beta_1$-encoding DNA, contained on separate EcoRI fragments, were isolated, blunt-ended and separately ligated to the blunt-ended vector fragment of pCMV locating the DNA between the CMV promoter and SV40 polyadenylation sites in pCMV. To ligate the $\alpha_{1D}$-encoding cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence of restriction enzyme recognition sites:

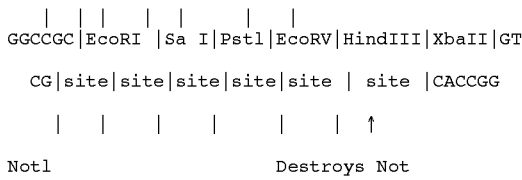

The $\alpha_{1D}$-encoding DNA, isolated as a BamHI/XhoI fragment from pVDCCIII(A), was then ligated to XbaII/SalI-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit-encoding DNA. After inserting the subunit-encoding DNA into pCMV, the splice donor/splice acceptor sites are located 3' of the CMV promoter and 5' of the subunit-encoding DNA start codon. After inserting the subunit-encoding DNA into pcDNA1, the splice donor/splice acceptor sites are located 3' of the subunit cDNA stop codon.

2. Transfection of HEK 293 cells

HEK 293 cells were transiently co-transfected with the $\alpha_{1D}$, $\alpha_2$ and $\beta_1$ subunit-encoding DNA in pCMV or with the $\alpha_{1D}$, $\alpha_2$ and $\beta$ subunit-encoding DNA in pcDNA1 (vectors pVDCCIII(A), pHBCaCH$\alpha_2$A and pHBCaCH$\beta_{1b}$RBS(A), respectively (see, International PCT application No. PCT/US94/09230, see, also allowed U.S. application Ser. No. 08/149,097). Plasmid pCMVβgal was included in each transfection as a measure of transfection efficiency. The results of β-galactosidase assays of the transfectants (International PCT application No. PCT/US94/09230, see, also allowed U.S. application Ser. No. 08/149,097), indicated that HEK 293 cells were transfected equally efficiently with pCMV- and pcDNA1 -based plasmids. The pcDNA1-based plasmids, however, are presently preferred for expression of calcium channel receptors.

D. Expression in *Xenopus laevis* Oöcytes of RNA Encoding Human Neuronal Calcium Channel Subunits Various combinations of the transcripts of DNA encoding the human neuronal $\alpha_{1D}$, $\alpha_2$ and $\beta_1$ subunits prepared in vitro were injected into *Xenopus laevis* oöcytes. Those injected with combinations that included $\alpha_{1D}$ exhibited voltage-activated barium currents.

1. Preparation of transcripts

Transcripts encoding the human neuronal calcium channel $\alpha_{1D}$, $\alpha_2$ and $\beta_1$ subunits were synthesized according to the instructions of the mCAP mRNA CAPPING KIT (Strategene, La Jolla, Calif. catalog #200350). As described in International PCT application No. PCT/US94/09230, see, also allowed U.S. application Ser. No. 08/149,097, plasmids PVDCC III.RBS(A), containing pcDNA1 and the $\alpha_{1D}$ cDNA that begins with a ribosome binding site and the eighth ATG codon of the coding sequence plasmid pHBCaCH$\alpha_1$A containing pcDNA1 and an $\alpha_2$ subunit cDNA, and plasmid pHBCaCH$\beta_{1b}$RBS(A) containing pcDNA1 and the $\beta_1$ DNA lacking intron sequence and containing a ribosome binding site were linearized by restriction digestion. The $\alpha_{1D}$ cDNA- and $\alpha_2$ subunit-encoding plasmids were digested with XhoI, and the $\beta_1$ subunit-encoding plasmid was digested with EcoRV. The DNA insert was transcribed with T7 RNA polymerase.

2. Injection of oöcytes

*Xenopus laevis* oöcytes were isolated and defolliculated by collagenase treatment and maintained in 100 mM NaCl, 2 mM KCl, 1.8 mM CaCl$_2$, 1 mM MgCl$_2$, 5 mM HEPES, pH 7.6, 20 μg/ml ampicillin and 25 μg/ml streptomycin at 19–25° C. for 2 to 5 days after injection and prior to recording. For each transcript that was injected into the oöcyte, 6 ng of the specific mRNA was injected per cell in a total volume of 50 nl.

3. Intracellular voltage recordings

Injected oöcytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution contained of the following: 40 mM BaCl$_2$, 36 mM tetraethylammonium chloride (TEA-Cl), 2 mM KCl, 5 mM 4-aminopyridine, 0.15 mM niflumic acid, 5 mM HEPES, pH 7.6.

a. Electrophysiological Analysis of Oöcytes Injected with Transcripts Encoding the Human Neuronal Calcium Channel $\alpha_1$, $\alpha_2$ and $\beta_1$-subunits Uninjected oöcytes were examined by two-electrode voltage clamp methods and a very small (25 nA) endogenous inward Ba$^{2+}$ current was detected in only one of seven analyzed cells.

Oöcytes coinjected with $\alpha_{1D}$, $\alpha_2$ and $\beta_1$ subunit transcripts expressed sustained inward barium currents upon depolarization of the membrane from a holding potential of −90 mV or −50 mV (154±129 nA, n=21). These currents typically showed little inactivation when test pulses ranging from 140 to 700 msec. were administered. Depolarization to a series of voltages revealed currents that first appeared at approximately −30 mV and peaked at approximately 0 mV.

Application of the DHP Bay K 8644 increased the magnitude of the currents, prolonged the tail currents present upon repolarization of the cell and induced a hyperpolarizing shift in current activation. Bay K 8644 was prepared fresh from a stock solution in DMSO and introduced as a 10× concentrate directly into the 60 μl bath while the perfusion pump was turned off. The DMSO concentration of the final diluted drug solutions in contact with the cell never exceeded 0.1%. Control experiments showed that 0.1% DMSO had no effect on membrane currents.

Application of the DHP antagonist nifedipine (stock solution prepared in DMSO and applied to the cell as described for application of Bay K 8644) blocked a substantial fraction (91±6%, n=7) of the inward barium current in oöcytes coinjected with transcripts of the $\alpha_{1D}$, $\alpha_2$ and $\beta_1$ subunits. A residual inactivating component of the inward barium current typically remained after nifedipine application. The inward barium current was blocked completely by 50 μM Cd$^{2+}$, but only approximately 15% by 100 μM Ni$^{2+}$.

The effect of ω-CgTX-GVIA on the inward barium currents in oöcytes co-injected with transcripts of the $\alpha_{1D}$, $\alpha_2$, and $\beta_1$ subunits was investigated. ω-CgTX-GVIA (Bachem, Inc., Torrance Calif.) was prepared in the 15 mM BaCl$_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ω-CgTX binding by divalent cations, recordings were made in 15 mM BaCl$_2$, 73.5 mM tetraethylammonium chloride, and the remaining ingredients identical to the 40 mM Ba$^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 μM) of ω-CgTX. The test currents and the accompanying tail currents were blocked progressively within two to three minutes after application of ωCgTX, but both recovered partially as the ωCgTX was flushed from the bath.

b. Analysis of Oöcytes Injected with Transcripts Encoding the Human Neuronal Calcium Channel $\alpha_{1D}$ or Transcripts Encoding an $\alpha_{1D}$ and other Subunits The contribution of the $\alpha_2$ and $\beta_1$ subunits to the inward barium current in oöcytes injected with transcripts encoding the $\alpha_{1D}$, $\alpha_2$ and $\beta_1$ subunits was assessed by expression of the $\alpha_{1D}$ subunit alone or in combination with either the $\beta_1$ subunit or the $\alpha_2$ subunit. In oöcytes injected with only the transcript of a $\alpha_{1D}$ cDNA, no $Ba^{2+}$ currents were detected (n=3). In oöcytes injected with transcripts of $\alpha_{1D}$ and $\beta_1$ encoding DNA, small (108±39 nA) $Ba^{2+}$ currents were detected upon depolarization of the membrane from a holding potential of –90 mV that resembled the currents observed in cells injected with transcripts of $\alpha_{1D}$, $\alpha_2$ and $\beta_1$ encoding DNA, although the magnitude of the current was less. In two of the four oöcytes injected with transcripts of the $\alpha_{1D}$-encoding and $\beta_1$-encoding DNA, the $Ba^{2+}$ currents exhibited a sensitivity to Bay K 8644 that was similar to the Bay K 8644 sensitivity of $Ba^{2+}$ currents expressed in oöcytes injected with transcripts encoding the $\alpha_{1D}$ $\alpha_1$-, $\alpha_2$- and $\beta_1$ subunits.

Three of five oöcytes injected with transcripts encoding the $\alpha_{1D}$ and $\alpha_2$ subunits exhibited very small $Ba^{2+}$ currents (15–30 nA) upon depolarization of the membrane from a holding potential of –90 mV. These barium currents showed little or no response to Bay K 8644.

c. Analysis of oöcytes Injected with Transcripts Encoding the Human Neuronal Calcium Channel $\alpha_2$ and/or $\beta_1$ Subunit To evaluate the contribution of the $\alpha_{1D}\alpha_1$-subunit to the inward barium currents detected in oöcytes co-injected with transcripts encoding the $\alpha_{1D}$, $\alpha_2$ and $\beta_1$ subunits, oöcytes injected with transcripts encoding the human neuronal calcium channel $\alpha_2$ and/or $\beta_1$ subunits were assayed for barium currents. Oöcytes injected with transcripts encoding the $\alpha_2$ subunit displayed no detectable inward barium currents (n=5). Oöcytes injected with transcripts encoding a $\beta_1$ subunit displayed measurable (54±23 nA, n=5) inward barium currents upon depolarization and oöcytes injected with transcripts encoding the $\alpha_2$ and $\beta_1$ subunits displayed inward barium currents that were approximately 50% larger (80±61 nA, n=18) than those detected in oöcytes injected with transcripts of the $\beta_1$-encoding DNA only.

The inward barium currents in oöcytes injected with transcripts encoding the $\beta_1$ subunit or $\alpha_2$ and $\beta_1$ subunits typically were first observed when the membrane was depolarized to –30 mV from a holding potential of –90 mV and peaked when the membrane was depolarized to 10 to 20 mV. Macroscopically, the currents in oöcytes injected with transcripts encoding the $\alpha_2$ and $\beta_1$ subunits or with transcripts encoding the $\beta_1$ subunit were indistinguishable. In contrast to the currents in oöcytes co-injected with transcripts of $\alpha_{1D}$, $\alpha_2$ and $\beta_1$ subunit encoding DNA, these currents showed a significant inactivation during the test pulse and a strong sensitivity to the holding potential. The inward barium currents in oöcytes co-injected with transcripts encoding the $\alpha_2$ and $\beta_1$ subunits usually inactivated to 10–60% of the peak magnitude during a 140-msec pulse and were significantly more sensitive to holding potential than those in oöcytes co-injected with transcripts encoding the $\alpha_{1D}$, $\alpha_2$ and $\beta_1$ subunits. Changing the holding potential of the membranes of oöcytes co-injected with transcripts encoding the $\alpha_2$ and $\beta_1$ subunits from –90 to –50 mV resulted in an approximately 81% (n=11) reduction in the magnitude of the inward barium current of these cells. In contrast, the inward barium current measured in oöcytes co-injected with transcripts encoding the $\alpha_{1D}$, $\alpha_2$ and $\beta_1$ subunits were reduced approximately 24% (n=11) when the holding potential was changed from –90 to –50 mV.

The inward barium currents detected in oöcytes injected with transcripts encoding the $\alpha_2$ and $\beta_1$ subunits were pharmacologically distinct from those observed in oöcytes co-injected with transcripts encoding the $\alpha_{1D}$, $\alpha_2$ and $\beta_1$ subunits. Oöcytes injected with transcripts encoding the $\alpha_2$ and $\beta_1$ subunits displayed inward barium currents that were insensitive to Bay K 8644 (n=11). Nifedipine sensitivity was difficult to measure because of the holding potential sensitivity of nifedipine and the current observed in oöcytes injected with transcripts encoding the $\alpha_2$ and $\beta_1$ subunits. Nevertheless, two oöcytes that were co-injected with transcripts encoding the $\alpha_2$ and $\beta_1$ subunits displayed measurable (25 to 45 nA) inward barium currents that were insensitive to nifedipine (5 to 10 μM), when depolarized from a holding potential of –50 mV. The inward barium currents in oöcytes injected with transcripts encoding the $\alpha_2$ and $\beta_1$ subunits showed the same sensitivity to heavy metals as the currents detected in oöcytes injected with transcripts encoding the $\alpha_{1D}$, $\alpha_2$ and $\beta_1$ subunits.

The inward barium current detected in oöcytes injected with transcripts encoding the human neuronal $\alpha_2$ and $\beta_1$ subunits has pharmacological and biophysical properties that resemble calcium currents in uninjected Xenopus oöcytes. Because the amino acids of this human neuronal calcium channel $\beta_1$ subunit lack hydrophobic segments capable of forming transmembrane domains. It is unlikely that recombinant $\beta_1$ subunits alone form an ion channel, but rather that an endogenous $\alpha_1$ subunit exists in oöcytes and that the activity mediated by such an $\alpha_1$ subunit is enhanced by expression of a human neuronal $\beta_1$ subunit.

E. Expression of DNA Encoding Human Neuronal Calcium Channel $\alpha_{1B}$, $\alpha_{2B}$ and $\beta_{1-2}$ Subunits in HEK Cells 1. Transfection of HEK cells The transient expression of the human neuronal $\alpha_{1B-1}$, $\alpha_{2b}$ and $\beta_{1-2}$ subunits was studied in HEK293 cells. The HEK293 cells were grown as a monolayer in Dulbecco's modified Eagle's medium (Gibco) containing 5% defined-supplemented bovine calf serum (Hyclone) plus penicillin G (100 U/ml) and steptomycin sulfate (100 μg/ml). HEK293 cell transfections were mediated by calcium phosphate as described above. Transfected cells were examined for inward $Ba^{2+}$ currents ($I_{Ba}$) mediated by voltage-dependent $Ca^{2+}$ channels.

Cells were transfected ($2\times10^6$ per polylysine-coated plate). Standard transfections (10-cm dish) contained 8 μg of pcDNA$\alpha_{1B-1}$, 5 μg of pHBCaCH$\alpha_2$A, 2 μg pHBCaCH$\beta_{1b}$RBS(A) (see, International PCT application No. PCT/US94/09230, see, also allowed U.S. application Ser. No. 08/149,097), 2 μg of CMVβ (Clontech) β-galactosidase expression plasmid, and pUC18 to maintain a constant mass of 20 μg/ml. Cells were analyzed 48 to 72 hours after transfection. Transfection efficiencies (±10%), which were determined by in situ histochemical staining for β-galactosidase activity (Sanes et al. (1986) EMBO J., 5:3133), generally were greater than 50%.

2. Electrophysiological analysis of transfectant currents
a. Materials and Methods Properties of recombinantly expressed $Ca^{2+}$ channels were studied by whole cell patch-clamp techniques. Recordings were performed on transfected HEK293 cells 2 to 3 days after transfection. Cells were plated at 100,000 to 300,000 cells per polylysine-coated, 35-mm tissue culture dishes (Falcon, Oxnard, Calif.) 24 hours before recordings. Cells were perfused with 15 mM $BaCl_2$, 125 mM choline chloride, 1 mM $MgCl_2$, and 10 mM Hepes (pH=7.3) adjusted with tetraethylammonium hydroxide (bath solution). Pipettes were filled with 135 mM CsCl, 10 mM EGTA, 10 mM Hepes, 4 mM Mg-adenosine triphosphate (pH=7.5) adjusted with tetraethylammonium hydroxide. Sylgard (Dow-Corning, Midland, Mich.)-coated, firepolished, and filled pipettes had resistances of 1 to 2 megohm before gigohm seals were established to cells.

Bay K 8644 and nifedipine (Research Biochemicals, Natick, Mass.) were prepared from stock solutions (in dimethyl sulfoxide) and diluted into the bath solution. The dimethyl sulfoxide concentration in the final drug solutions in contact with the cells never exceeded 0.1%. Control experiments showed that 0.1% dimethyl sulfoxide had no effect on membrane currents. ωCgTX (Bachem, Inc., Torrance Calif.) was prepared in the 15 mM $BaCl_2$ bath solution plus 0.1% cytochrome C (Sigma, St. Louis Mo.) to serve as a carrier protein. Control experiments showed that cytochrome C had no effect on currents. These drugs were dissolved in bath solution, and continuously applied by means of puffer pipettes as required for a given experiment. Recordings were performed at room temperature (22° to 25° C.). Series resistance compensation (70 to 85%) was employed to minimize voltage error that resulted from pipette access resistance, typically 2 to 3.5 megohm. Current signals were filtered (−3 dB, 4-pole Bessel) at a frequency of ¼ to ⅕ the sampling rate, which ranged from 0.5 to 3 kHz. Voltage commands were generated and data were acquired with CLAMPEX (pClamp, Axon Instruments, Foster City, Calif.). All reported data are corrected for linear leak and capacitive components. Exponential fitting of currents was performed with CLAMPFIT (Axon Instruments, Foster City, Calif.).

b. Results

Transfectants were examined for inward $Ba^{2+}$ currents ($I_{Ba}$). Cells cotransfected with DNA encoding $\alpha_{1B-1}$, $\alpha_{2b}$, and $\beta_{1-2}$ subunits expressed high-voltage-activated $Ca^{2+}$ channels. $I_{Ba}$ first appeared when the membrane was depolarized from a holding potential of −90 mV to −20 mV and peaked in magnitude at 10 mV. Thirty-nine of 95 cells (12 independent transfections) had $I_{Ba}$ that ranged from 30 to 2700 pA, with a mean of 433 pA. The mean current density was 26 pA/pF, and the highest density was 150 pA/pF. The $I_{Ba}$ typically increased by 2- to 20-fold during the first 5 minutes of recording. Repeated depolarizations during long records often revealed rundown of $I_{Ba}$ usually not exceeding 20% within 10 min. $I_{Ba}$ typically activated within 10 ms and inactivated with both a fast time constant ranging from 46 to 105 ms and a slow time constant ranging from 291 to 453 ms (n=3). Inactivation showed a complex voltage dependence, such that $I_{Ba}$ elicited at $\geq 20$ mV inactivated more slowly than $I_{Ba}$ elicited at lower test voltages, possibly a result of an increase in the magnitude of slow compared to fast inactivation components at higher test voltages.

Recombinant $\alpha_{1B-1}\alpha_{2b}\beta_{1-2}$ channels were sensitive to holding potential. Steady-state inactivation of $I_{Ba}$ measured after a 30- to 60-s conditioning at various holding potentials, was approximately 50% at holding potential between −60 and −70 mV and approximately 90% at −40 mV. Recovery of $I_{Ba}$ from inactivation was usually incomplete, measuring 55 to 75% of the original magnitude within 1 min. after the holding potential was returned to more negative potentials, possibly indicating some rundown or a slow recovery rate.

Recombinant $\alpha_{1B-1}\alpha_{2b}\beta_{1-2}$ channels were also blocked irreversibly by ω-CgTx concentrations ranging from 0.5 to 10 μM during the time scale of the experiments. Application of 5 μM toxin (n=7) blocked the activity completely within 2 min., and no recovery of $I_{Ba}$ was observed after washing ω-CgTx from the bath for up to 15 min. $d^{2+}$ blockage (50 μM) was rapid, complete, and reversible; the DHPs Bay K 8644 (1 μM; n=4) or nifedipine (5 μM; n=3) had no discernable effect.

Cells cotransfected with DNA encoding $\alpha_{1B-1}$, $\alpha_{2b}$, and $\beta_{1-2}$ subunits predominantly displayed a single class of saturable, high-affinity ω-CgTx binding sites. The determined dissociation constant ($K_d$) value was 54.6±14.5 pM (n=4). Cells transfected with the vector containing only β-galactosidase-encoding DNA or $\alpha_{2b}\beta$-encoding DNA showed no specific binding. The binding capacity ($B_{max}$) of the $\alpha_{1B-1}\alpha_{2b}\beta$-transfected cells was 28,710±11,950 sites per cell (n=4).

These results demonstrate that $\alpha_{1B-1}\alpha_{2b}\beta_{1-2}$-transfected cells express high-voltage-activated, inactivating $Ca^{2+}$ channel activity that is irreversibly blocked by ω-CgTx, insensitive to DHPs, and sensitive to holding potential. The activation and inactivation kinetics and voltage sensitivity of the channel formed in these cells are generally consistent with previous characterizations of neuronal N-type $Ca^{2+}$ channels.

F. Expression of DNA Encoding Human Neuronal Calcium Channel $\alpha_{1B-1}$, $\alpha_{1B-2}$, $\alpha_{2B}$, $\beta_{1-2}$ and $\beta_{1-3}$ Subunits in HEK Cells Significant $Ba^{2+}$ currents were not detected in untransfected HEK293 cells. Furthermore, untransfected HEK293 cells do not express detectable ω-CgTx GVIA binding sites. In order to approximate the expression of a homogeneous population of trimeric $\alpha_{1B}$, $\alpha_{2b}$ and $\beta_1$ protein complexes in transfected HEK293 cells, the $\alpha_{1B}$, $\alpha_{2b}$ and $\beta_1$ expression levels were altered. The efficiency of expression and assembly of channel complexes at the cell surface were optimized by adjusting the molar ratio of $\alpha_{1B}$, $\alpha_{2b}$ and $\beta_1$ expression plasmids used in the transfections. The transfectants were analyzed for mRNA levels, ω-CgTx GVIA binding and $Ca^{2+}$ channel current density in order to determine near optimal channel expression in the absence of immunological reagents for evaluating protein expression. Higher molar ratios of $\alpha_{2b}$ appeared to increase calcium channel activity.

1. Transfections

HEK293 cells were maintained in DMEM (Gibco #320-1965AJ), 5.5% Defined/Supplemented bovine calf serum (Hyclone #A-2151-L), 100 U/ml penicillin G and 100 μg/ml streptomycin. $Ca^{2+}$-phosphate based transient transfections were performed and analyzed as described above. Cells were co-transfected with either 8 μg pcDNA1$\alpha_{1B-1}$ (described in International PCT application No. PCT/US94/09230, see, also allowed U.S. application Ser. No. 08/149,097), 5 μg pHBCaCH$\alpha_2$A (see, Example IV.B.), 2 μg pHBCaCH$\beta_{1b}$RBS(A) ($\beta_{1-2}$ expression plasmid; see Examples III.A. and IX.E.), and 2 μg pCMVβ-gal [Clontech, Palo Alto, Calif.] (2:1.8:1 molar ratio of $Ca^{2+}$ channel subunit expression plasmids) or with 3 μg pcDNA1$\alpha_{1B-1}$ or pcDNA1$\alpha_{1B-2}$, 11.25 μg pHBCaCH$\alpha_2$A, 0.75 or 1.0 μg pHBCaCH$\beta_{1b}$RBS(A) or pcDNA1$\beta_{1-3}$ and 2 μg pCMVβ-gal (2:10.9:1 molar ratio of $Ca^{2+}$ channel subunit expression plasmids). Plasmid pCMVβ-gal, a β-galactosidase expression plasmid, was included in the transfections as a marker to permit transfection efficiency estimates by histochemical staining. When less than three subunits were expressed, pCMVPL2, a pCMV promoter-containing vector that lacks a cDNA insert, was substituted to maintain equal moles of pCMV-based DNA in the transfection. pUC18 DNA was used to maintain the total mass of DNA in the transfection at 20 μg/plate.

RNA from the transfected cells was analyzed by Northern blot analysis for calcium channel subunit mRNA expression using random primed $^{32}$P-labeled subunit specific probes. HEK293 cells co-transfected with $\alpha_{1B-1}$, $\alpha_{2b}$ and $\beta_{1-2}$ expression plasmids (8, 5 and 2 µg, respectively; molar ratio=2:1.8:1) did not express equivalent levels of each Ca$^{2+}$ channel subunit mRNA. Relatively high levels of $\alpha_{1B-1}$ and $\beta_{1-2}$ mRNAs were expressed, but significantly lower levels of $\alpha_{2b}$ mRNA were expressed. Based on autoradiograph exposures required to produce equivalent signals for all three mRNAs, $\alpha_{2b}$ transcript levels were estimated to be 5 to 10 times lower than $\alpha_{1B-1}$ and $\beta_{1-2}$ transcript levels. Untransfected HEK293 cells did not express detectable levels of $\alpha_{1B-1}$, $\alpha_{2b}$, or $\beta_{1-2}$ mRNAs.

To achieve equivalent Ca$^{2+}$ channel subunit mRNA expression levels, a series of transfections was performed with various amounts of $\alpha_{1B-1}$, $\alpha_{2b}$ and $\beta_{1-2}$ expression plasmids. Because the $\alpha_{1B-1}$ and $\beta_{1-2}$ mRNAs were expressed at very high levels compared to $\alpha_{2b}$ mRNA, the mass of $\alpha_{1B-1}$ and $\beta_{1-2}$ plasmids was lowered and the mass of $\beta_{2b}$ plasmid was increased in the transfection experiments. Co-transfection with 3, 11.25 and 0.75 µg of $\alpha_{1B-1}$, $\alpha_{2b}$ and $\beta_{1-2}$ expression plasmids, respectively (molar ratio= 2:10.9:1), approached equivalent expression levels of each Ca$^{2+}$ channel subunit mRNA. The relative molar quantity of $\alpha_{2b}$ expression plasmid to $\alpha_{1B-1}$ and $\beta_{1-2}$ expression plasmids was increased 6-fold. The mass of $\alpha_{1B-1}$ and $\beta_{1-2}$ plasmids in the transfection was decreased 2.67-fold and the mass of $\alpha_{2b}$ plasmid was increased 2.25-fold. The 6-fold molar increase of $\alpha_{2b}$ relative to $\alpha_{1B-1}$ and $\beta_{1-2}$ required to achieve near equal abundance mRNA levels is consistent with the previous 5- to 10-fold lower estimate of relative $\alpha_{2b}$ mRNA abundance. ω-CgTx GVIA binding to cells transfected with various amounts of expression plasmids indicated that the 3, 11.25 and 0.75 µg of $\alpha_{1B-1}$, $\alpha_{2b}$ and $\beta_{1-2}$ plasmids, respectively, improved the level of cell surface expression of channel complexes. Further increases in the mass of $\alpha_{2b}$ and $\beta_{1-2}$ expression plasmids while $\alpha_{1B-1}$ was held constant, and alterations in the mass of the $\alpha_{1B-1}$ expression plasmid while $\alpha_{2b}$ and $\beta_{1-2}$ were held constant, indicated that the cell surface expression of ω-CgTx GVIA binding sites per cell was nearly optimal. All subsequent transfections were performed with 3, 11.25 and 0.75 µg or 1.0 µg of $\alpha_{1B-1}$ or $\alpha_{1B-2}$, $\alpha_{2b}$ and $\beta_{1-2}$ or $\beta_{1-3}$ expression plasmids, respectively.

2. $^{125}$I-ω-CgTx GVIA binding to transfected cells

Statistical analysis of the $K_d$ and $B_{max}$ values was performed using one-way analysis of variance (ANOVA) followed by the Tukey-Kramer test for multiple pairwise comparisons (p≤0.05).

Combinations of human voltage-dependent Ca$^{2+}$ channel subunits, $\alpha_{1B-1}$, $\alpha_{1B-2}$, $\alpha_{2b}$, $\beta_{1-2}$ and $\beta_{1-3}$, were analyzed for saturation binding of $^{125}$I-ω-CgTx GVIA. About 200,000 cells were used per assay, except for the $\alpha_{1B-1}$, $\alpha_{1B-2}$, $\alpha_{1B-1}\alpha_{2b}$ and $\alpha_{1B-2}\alpha_{2b}$ combinations which were assayed with 1×10$^6$ cells per tube. The transfected cells displayed a single-class of saturable, high-affinity binding sites. The values for the dissociation constants ($K_d$) and binding capacities ($B_{max}$) were determined for the different combinations. The results are summarized as follows:

| Subunit Combination | $K_d$ (pM) | $B_{max}$ (sites/cell) |
| --- | --- | --- |
| $\alpha_{1B-1}\alpha_{2b}\beta_{1-2}$ | 54.9 ± 11.1 (n = 4) | 45,324 ± 15,606 |
| $\alpha_{1B-1}\alpha_{2b}\beta_{1-3}$ | 53.2 ± 3.6 (n = 3) | 91,004 ± 37,654 |
| $\alpha_{1B-1}\beta_{1-2}$ | 17.9 ± 1.9 (n = 3) | 5,756 ± 2,163 |
| $\alpha_{1B-1}\beta_{1-3}$ | 17.9 ± 1.6 (n = 3) | 8,729 ± 2,980 |
| $\alpha_{1B-1}\alpha_{2b}$ | 84.6 ± 15.3 (n = 3) | 2,256 ± 356 |
| $\alpha_{1B-1}$ | 31.7 ± 4.2 (n = 3) | 757 ± 128 |
| $\alpha_{1B-2}\alpha_{2b}\beta_{1-2}$ | 53.0 ± 4.8 (n = 3) | 19,371 ± 3,798 |
| $\alpha_{1B-2}\alpha_{2b}\beta_{1-3}$ | 44.3 ± 8.1 (n = 3) | 37,652 ± 8,129 |
| $\alpha_{1B-2}\beta_{1-2}$ | 16.4 ± 1.2 (n = 3) | 2,126 ± 412 |
| $\alpha_{1B-2}\beta_{1-3}$ | 22.2 ± 5.8 (n = 3) | 2,944 ± 1,168 |
| $\alpha_{1B-2}\alpha_{2b}$ | N.D.* (n = 3) | N.D. |
| $\alpha_{1B-2}$ | N.D. | N.D. |

* N.D. = not detectable

Cells transfected with subunit combinations lacking either the $\alpha_{1B-1}$ or the $\alpha_{1B-2}$ subunit did not exhibit any detectable $^{125}$I-ω-CgTx GVIA binding (≤600 sites/cell). $^{125}$I-ω-CgTx GVIA binding to HEK293 cells transfected with $\alpha_{1B-2}$ alone or $\alpha_{1B-2}\alpha_{2b}$ was too low for reliable Scatchard analysis of the data. Comparison of the $K_d$ and $B_{max}$ values revealed several relationships between specific combinations of subunits and the binding affinities and capacities of the transfected cells. In cells transfected with all three subunits, ($\alpha_{1B-1}\alpha_{2b}\beta_{1-2}$-, $\alpha_{1B-1}\alpha_{2b}\beta_{1-3}$-, $\alpha_{1B-2}\alpha_{2b}\beta_{1-2}$-, or $\alpha_{1B-2}\alpha_{2b}\beta_{1-3}$-transfectants) the $K_d$ values were indistinguishable (p>0.05), ranging from 44.3±8.1 pM to 54.9±11.1 pM. In cells transfected with two-subunit combinations lacking the $\alpha_{2b}$ subunit ($\alpha_{1B-1}\beta_{1-2}$, $\alpha_{1B-1}\beta_{1-3}$, $\alpha_{1B-2}\beta_{1-2}$ or $\alpha_{1B-2}\beta_{1-3}$) the $K_d$ values were significantly lower than the three-subunit combinations (p<0.01), ranging from 16.4±1.2 to 22.2±5.8 pM. Cells transfected with only the $\alpha_{1B-1}$ subunit had a $K_d$ value of 31.7±4.2 pM, a value that was not different from the two-subunit combinations lacking $\alpha_{2b}$ (p<0.05). As with the comparison between the four $\alpha_{1B}\alpha_{2b}\beta_1$ versus $\alpha_{1B}\beta_1$ combinations, when the $\alpha_{1B-1}$ was co-expressed with $\alpha_{2b}$, the $K_d$ increased significantly (p<0.05) from 31.7±4.2 to 84.6±5.3 pM. These data demonstrate that co-expression of the $\alpha_{2b}$ subunit with $\alpha_{1B-1}$, $\alpha_{1B-1}\beta_{1-2}$, $\alpha_{1B-1}\beta_{13}$, $\alpha_{1B-2}\beta_{1-2}$ or $\alpha_{1B-2\beta1-3}$ subunit combinations results in lower binding affinity of the cell surface receptors for $^{125}$I-ω-CgTx GVIA. The $B_{max}$ values of cells transfected with various subunit combinations also differed considerably. Cells transfected with the $\alpha_{1B-1}$ subunit alone expressed a low but detectable number of binding sites (approximately 750 binding sites/cell). When the $\alpha_{1B-1}$ subunit was co-expressed with the $\alpha_{2b}$ subunit, the binding capacity increased approximately threefold while co-expression of $\alpha_{1-2}$ or $\beta_{1-3}$ subunit with $\alpha_{1B-1}$ resulted in 8- to 10-fold higher expression of surface binding. Cells transfected with all three subunits expressed the highest number of cell surface receptors. The binding capacities of cells transfected with $\alpha_{1B-1}\alpha_{2b}\beta_{1-3}$ or $\alpha_{1B-2}\alpha_{2b}\beta_{1-3}$ combinations were approximately two-fold higher than the corresponding combinations containing the $\beta_{1-2}$ subunit. Likewise, cells transfected with $\alpha_{1B-1}\alpha_{2b}\beta_{1-2}$ or $\alpha_{1B-1}\alpha_{2b}\beta_{1-3}$ combinations expressed approximately 2.5-fold more binding sites per cell than the corresponding combinations containing $\alpha_{1B-2}$. In all cases, co-expression of the $\alpha_{2b}$ subunit with $\alpha_{1B}$ and $\beta_1$ increased the surface receptor density compared to cells transfected with only the corresponding $\alpha_{1B}$ and $\beta_1$ combinations; approximately 8-fold for $\alpha_{1B-1}\alpha_{2b}\beta_{1-2}$, 10-fold for $\alpha_{1B-1}\alpha_{2b}\beta_{1-3}$, 9-fold for $\alpha_{1B-2}\alpha_{2b}\beta_{1-2}$, and 13-fold for $\alpha_{1B-2}\alpha_{2b}\beta_{1-3}$. Thus, comparison of the $B_{max}$ values suggests that the toxin-binding subunit, $\alpha_{1B-1}$ or $\alpha_{1B-2}$, is more efficiently expressed and assembled on the cell surface when co-ex-pressed with either the $\alpha_{2b}$ or the $\beta_{1-2}$ or $\beta_{1-3}$ subunit, and most efficiently expressed when $\alpha_{2b}$ and $\beta_1$ subunits are present.

3. Electrophysiology

Functional expression of $\alpha_{1B-1}\alpha_{2b}\beta_{1-2}$ and $\alpha_{1B-1}\beta_{1-2}$ subunit combinations was evaluated using the whole-cell recording technique. Transfected cells that had no contacts with surrounding cells and simple morphology were used approximately 48 hours after transfection for recording. The pipette solution was (in mM) 135 CsCl, 10 EGTA, 1 MgCl$_2$, 10 HEPES, and 4 mM Mg-ATP (pH 7.3, adjusted with TEA-OH). The external solution was (in mM) 15 BaCl$_2$, 125 Choline Cl, 1 MgCl$_2$, and 10 HEPES (pH 7.3, adjusted with TEA-OH). ω-CgTx GVIA (Bachem) was prepared in the external solution with 0.1% cytochrome C (Sigma) to serve as a carrier. Control experiments showed that cytochrome C had no effect on the Ba$^{2+}$ current.

The macroscopic electrophysiological properties of Ba$^{2+}$ currents in cells transfected with various amounts of the $\alpha_{2b}$ expression plasmid with the relative amounts of $\alpha_{1B-1}$ and $\beta_{1-2}$ plasmids held constant were examined. The amplitudes and densities of the Ba$^{2+}$ currents (15 mM BaCl$_2$) recorded from whole cells of these transfectants differed dramatically. The average currents from 7 to 11 cells of three types of transfections (no $\alpha_{2b}$; 2:1.8:1 [$\alpha_{1B-1}$:$\alpha_{2b}$:$\beta_{1-2}$] molar ratio; and 2:10.9:1 [$\alpha_{1B-1}$:$\alpha_{2b}$:$\beta_{1-2}$] molar ratio) were determined. The smallest currents (range: 10 to 205 pA) were recorded when $\alpha_{2b}$ was not included in the transfection, and the largest currents (range: 50 to 8300 pA) were recorded with the 2:10.9:1 ratio of $\alpha_{1B-1}\alpha_{2b}\beta_{1-2}$ plasmids, the ratio that resulted in near equivalent mRNA levels for each subunit transcript. When the amount of $\alpha_{2b}$ plasmid was adjusted to yield approximately an equal abundance of subunit mRNAs, the average peak Ba$^{2+}$ current increased from 433 pA to 1,824 pA (4.2-fold) with a corresponding increase in average current density from 26 pA/pF to 127 pA/pF (4.9-fold). This increase is in the presence of a 2.7-fold decrease in the mass of $\alpha_{1B-1}$ and $\beta_{1-2}$ expression plasmids in the transfections. In all transfections, the magnitudes of the Ba$^{2+}$ currents did not follow a normal distribution.

To compare the subunit combinations and determine the effects of $\alpha_{2b}$, the current-voltage properties of cells transfected with $\alpha_{1B-1}\beta_{1-2}$ or with $\alpha_{1B-1}\alpha_{2b}\beta_{1-2}$ in either the 2:1.8:1 ($\alpha_{1B-1}$:$\alpha_{2b}$:$\beta_{1-2}$) molar ratio or the 2:10.9:1 ($\alpha_{1B-1}$:$\alpha_{2b}$:$\beta_{1-2}$) molar ratio transfectants were examined. The extreme examples of no $\alpha_{2b}$ and 11.25 μg $\alpha_{2b}$ (2:10.9:1 molar ratio) showed no significant differences in the current voltage plot at test potentials between 0 mV and +40 mV (p<0.05). The slight differences observed at either side of the peak region of the current voltage plot were likely due to normalization. The very small currents observed in the $\alpha_{1B-1}\beta_{1-2}$ transfected cells have a substantially higher component of residual leak relative to the barium current that is activated by the test pulse. When the current voltage plots are normalized, this leak is a much greater component than in the $\alpha_{1B-1}\alpha_{2b}\beta_{1-2}$ transfected cells and as a result, the current-voltage plot appears broader. This is the most likely explanation of the apparent differences in the current voltage plots, especially given the fact that the current-voltage plot for the $\alpha_{1B-1}\beta_{1-2}$ transfected cells diverge on both sides of the peak. Typically, when the voltage-dependence activation is shifted, the entire current-voltage plot is shifted, which was not observed. To qualitatively compare the kinetics of each, the average responses of test pulses from −90 mV to 10 mV were normalized and plotted. No significant differences in activation or inactivation kinetics of whole-cell Ba$^{2+}$ currents were observed with any combination.

G. Expression of DNA Encoding Human Neuronal Calcium Channel $\alpha_{1E-3}\alpha_{2B}\beta_{1-3}$ and $\alpha_{1E-1}\alpha_{2B}\beta_{1-3}$ Subunits in HEK Cells Functional expression of the $\alpha_{1E-1}\alpha_{2B}\beta_{1-3}$ and $\alpha_{1E-3}\alpha_{2B}\beta_{1-3}$, as well as $\alpha_{1E-3}$ was evaluated using the whole cell recording technique.

1. Methods

Recordings were performed on transiently transfected HEK 293 cells, which had no contacts with surrounding cells and which had simple morphology, two days following the transfection. The internal solution used to fill pipettes for recording the barium current from the transfected recombinant calcium channels was (in mM) 135 CsCl, 10 EGTA, 1 MgCl$_2$, 10 HEPES, and 4 mM Mg-ATP (pH 7.4–7.5, adjusted with TEA-OH). The external solution for recording the barium current was (in mM) 15 BaCl$_2$, 150 Choline Cl, 1 MgCl$_2$, and 10 HEPES and 5 TEA-OH (pH 7.3, adjusted with TEA-OH). In experiments in which Ca$^{2+}$ was replaced for Ba$^{2+}$, a Laminar flow chamber was used in order to completely exchange the extracellular solution and prevent any mixing of Ba$^{2+}$ and Ca$^{2+}$. ω-CgTx GVIA was prepared in the external solution with 0.1% cytochrome C to serve as a carrier, the toxin was applied by pressurized puffer pipette. Series resistance was compensated 70–85% and currents were analyzed only if the voltage error from series resistance was less than 5 mV. Leak resistance and capacitance was corrected by subtracting the scaled current observed with the P/-4 protocol as implemented by pClamp (Axon Instruments).

2. Electrophysiology Results

Cells transfected with $\alpha_{1E-1}\alpha_{2b}\beta_{1-3}$ or $\alpha_{1E-3}\alpha_{2b}\beta_{1-3}$ showed strong barium currents with whole cell patch clamp recordings. Cells expressing $\alpha_{1E-3}\alpha_{2B}\beta_{1-3}$ had larger peak currents than those expressing $\alpha_{1B-1}\alpha_{2b}\beta_{1-3}$. In addition, the kinetics of activation and inactivation are clearly substantially faster in the cells expressing $\alpha_{1E}$ calcium channels. HEK 293 cells expressing $\alpha_{1E-3}$ alone have a significant degree of functional calcium channels, with properties similar to those expressing $\alpha_{1E}\alpha_{2b}\beta_{1-3}$ but with substantially smaller peak barium currents. Thus, with $\alpha_{1E}$, the $\alpha_2$ and $\beta_1$ subunits are not required for functional expression of $\alpha_{1E}$ mediated calcium channels, but do substantially increase the number of functional calcium channels.

Examination of the current voltage properties of $\alpha_{1E}\alpha_{2b}\beta_{1-3}$ expressing cells indicates that $\alpha_{1E-3}\alpha_{2b}\beta_{1-3}$ is a high-voltage activated calcium channel arid the peak current is reached at a potential only slightly less positive than other neuronal calcium channels also expressing $\alpha_{2b}$ and $\beta_1$, and $\alpha_{1B}$ and $\alpha_{1D}$. Current voltage properties of $\alpha_{1E-1}\alpha_{2b}\beta_{1-3}$ and $\alpha_{1E-3}\alpha_{2b}\beta_{1-3}$ are statistically different from those of $\alpha_{1B}\alpha_{2b}\beta_{1-3}$. Current voltage curves for $\alpha_{1E-1}\alpha_{2b}\beta_{1-3}$ and $\alpha_{1E-3}\alpha_{2b}\beta_{1-3}$ peak at approximately +5mV, as does the current voltage curve for $\alpha_{1E-3}$ alone.

The kinetics and voltage dependence of inactivation using both prepulse (200 ms) and steady-state inactivation was examined. $\alpha_{1E}$ mediated calcium channels are rapidly inactivated relative to previously cloned calcium channels and other high voltage-activated calcium channels. $\alpha_{1E-3}\alpha_{2b}\beta_{1-3}$ mediated calcium channels are inactivated rapidly and are thus sensitive to relatively brief (200 ms) prepulses as well as long prepulses (>20s steady state inactivation), but recover rapidly from steady state inactivation. The kinetics of the rapid inactivation has two components, one with a time constant of approximately 25 ms and the other approximately 400 ms.

To determine whether $\alpha_{1E}$ mediated calcium channels have properties of low voltage activated calcium channels, the details of tail currents activated by a test pulse ranging −60 to +90 mV were measured at −60 mV. Tail currents recorded at −60 mV could be well fit by a single exponential of 150 to 300 μs; at least an order of magnitude faster than those typically observed with low voltage-activated calcium channels.

HEK 293 cells expressing $\alpha_{1E-3}\beta_{2b}\beta_{1-3}$ flux more current with Ba$^{2+}$ as the charge carrier and currents carried by Ba$^{2+}$ and Ca$^{2+}$ have different current-voltage properties. Furthermore, the time course of inactivation is slower and the amount of prepulse inactivation less with Ca$^{2+}$ as the charge carrier.

While the invention has been described with some specificity, modifications apparent to those with ordinary skill in the art may be made without departing from the scope of the invention. Since such modifications will be apparent to those of skill in the art, it is intended that this invention be limited only by the scope of the appended claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6528630B1). An electronic copy of the "Sequence Listing" will also be available from the USPTO upon request and payment of the fee set forth in 37 CFR 1.19(b)(3).

What is claimed is:

1. An isolated nucleic acid that encodes a subunit of a calcium channel, comprising a sequence of nucleotides selected from the group consisting of:
   (a) the coding portion of the sequence of nucleotides set forth in SEQ ID NOs: 49, 51 or 52;
   (b) a sequence of nucleotides that hybridizes under conditions of high stringency to the complement of the coding portion of the sequence of nucleotides set forth in SEQ ID NOs: 49, 51 or 52;
   (c) a sequence of nucleotides that encodes the sequence of amino acids encoded by SEQ ID NOs: 49, 51 or 52; and
   (d) a sequence of nucleotides that is degenerate with any of (a), (b) or (c).

2. The isolated nucleic acid of claim 1, comprising the coding portion of the sequence of nucleotides set forth in SEQ ID NOs: 49, 51 or 52.

3. An isolated nucleic acid molecule that is a splice variant of the nucleic acid molecule of claim 2.

4. A eukaryotic cell, comprising heterologous nucleic acid where the hetrologous nucleic acid is a nucleic acid of claim 1.

5. A eukaryotic cell, comprising hetrologous nucleic acid where the heterologous nucleic acid is a nucleic acid of claim 2.

6. The cell of claim 4, further comprising heterologous nucleic acid that encodes an $\alpha_2$-subunit of a calcium channel comprising an amino acid sequence selected from the group consisting of the coding regions of SEQ ID NOs: 11, 29, 30, 31, and 32.

7. The cell of claim 5, further comprising heterologous nucleic acid that encodes an $\alpha_2$-subunit of a calcium channel comprising an amino acid sequence selected from the group consisting of the coding regions of SEQ ID NOs: 11, 29, 30, 31, and 32.

8. The eukaryotic cell of claim 5 that has a functional heterologous calcium channel that contains at least one subunit encoded by the heterologous nucleic acid.

9. The eukaryotic cell of claim 7 selected from the group consisting of HEK 293 cells, Chinese hamster ovary cells, African green monkey cells, and mouse L cells.

10. A eukaryotic cell with a functional, heterologous calcium channel, produced by a process comprising:
    introducing into the cell heterologous nucleic acid that encodes at least one subunit of a calcium channel, wherein the subunit is encoded by the nucleic acid of claim 2.

11. The eukaryotic cell of claim 10 that is an amphibian oöcyte.

12. The eukaryotic cell of claim 8, further comprising an $\alpha_2$-subunit of a calcium channel comprising an amino acid sequence selected from the group consisting of the coding regions of SEQ ID NOs: 11, 29, 30, 31, and 32.

13. The eukaryotic cell of claim 8 with a functional, heterologous calcium channel, produced by a process comprising:
    introducing into the cell RNA that encodes a subunit of a calcium channel having an amino acid sequence encoded by SEQ ID NOs: 49, 51, or 52, wherein the RNA is translated to produce the subunit, and furthermore wherein:
    the heterologous calcium channel contains at least one subunit encoded by the heterologous nucleic acid.

14. The eukaryotic cell of claim 13 selected from the group consisting of HEK 293 cells, Chinese hamster ovary cells, African green monkey cells, mouse L cells and amphibian oöcytes.

15. The eukaryotic cell of claim 14 that is an amphibian oöcyte.

16. A method for identifying a compound that modulates the activity of a calcium channel, comprising:
    suspending a eukaryotic cell in a solution containing the compound and a calcium channel selective ion;
    depolarizing the cell membrane of the cell, and
    detecting the current or ions flowing into the cell, wherein;
    the heterologous calcium channel includes at least one calcium channel subunit encoded by DNA or RNA that is heterologous to the cell,
    the current that is detected is different from that produced by depolarizing the same or a substantially identical cell in the presence of the same calcium channel selective ion but in the absence of the compound; wherein;
    the eukaryotic cell comprises heterologous nucleic acid comprising the coding portion of the sequence of nucleotides set forth in SEQ ID NOs: 49, 51 or 52 and has a functional heterologous calcium channel that contains at least one subunit encoded by the heterologous nucleic acid.

17. The method of claim 16, wherein prior to the depolarization step the cell is maintained at a holding potential which substantially inactivates calcium channels that are endogenous to the cell.

18. The method of claim 17, wherein:
    the cell is an amphibian oöcyte;
    the heterologous subunits are encoded by nucleic acid injected into the oöcyte; and
    the heterologous subunits comprise the sequence of amino acids encoded by SEQ ID NOs: 49, 51, or 52.

19. The method of claim 16, wherein the cell is an HEK cell.

20. The method of claim 16, wherein:
    at least one subunit of the heterologous calcium channel comprises the sequence of amino acids encoded by SEQ ID NOs: 49, 51, or 52;
    the current that is detected is different from that produced by depolarizing the same or a substantially identical cell in the presence of the same calcium channel selective ion but in the absence of the compound.

21. A method for producing a subunit of a calcium channel, comprising introducing a nucleic acid molecule into a host cell, under condition whereby the encoded subunit is expressed, wherein;

the nucleic acid molecule encodes a subunit of a calcium channel and comprises a sequence of nucleotides selected from the group consisting of:
(a) the coding portion of the sequence of nucleotides set forth in SEQ ID NOs: 49, 51 or 52;
(b) a sequence of nucleotides that hybridizes under conditions of high stringency to the complement of the coding portion of the sequence of nucleotides set forth in SEQ ID NOs: 49, 51 or 52;
(c) a sequence of nucleotides that encodes the sequence of amino acids encoded by SEQ ID NOs: 49, 51 or 52; and
(d) a sequence of nucleotides that is degenerate with any of (a), (b) or (c).

22. The method of claim 21, wherein the cell is a eukaryotic cell.

23. A method for producing a subunit of a calcium channel, comprising introducing a nucleic acid molecule into a host cell, under condition whereby the encoded subunit is expressed, wherein;

the nucleic acid molecule encodes a subunit of a calcium channel and comprises the coding portion of the sequence of nucleotides set forth in SEQ ID NOs: 49, 51 or 52.

24. The method of claim 23, wherein the cell is a eukaryotic cell.

25. A eukaryotic cell, comprising a heterologous calcium channel with a subunit comprising SEQ ID NO: 50, the sequence of amino acids encoded by SEQ ID NO: 51, or the sequence of amino acids encoded by SEQ ID NO: 52.

26. The eukaryotic cell of claim 25, with a subunit comprising SEQ ID NO: 50.

27. An isolated nucleic acid molecule, comprising a sequence of nucleotides encoding the sequence of amino acids encoded by nucleotides 1506 to 2627 of SEQ ID NO: 49.

28. A method of identifying a nucleic acid that encodes an $\alpha_1$-subunit of a calcium channel comprising:
hybridizing a probe that comprises at least 16 contiguous nucleotides from nucleotides 1506 to 2627 of SEQ ID NO: 49 under conditions of at least low stringency to a nucleic acid library; and
selecting hybridizing nucleic acid fragments from the library.

29. The method of claim 28, wherein the probe comprises at least 30 nucleotides.

30. The method of claim 28, wherein hybridization is effected under conditions of high stringency.

31. The nucleic acid of claim 1 that is RNA.

32. The nucleic acid of claim 1 that is DNA.

33. A cell comprising nucleic acid that encodes a reporter gene construct containing a reporter gene in operative linkage with one or more transcription control elements that is regulated by a calcium channel, wherein;

the cell is a eukaryotic cell comprising heterologous nucleic acid comprising the coding portion of the sequence of nucleotides set forth in SEQ ID NOs: 49, 51 or 52.

34. A method for identifying compounds that modulate the activity of a calcium channel, the method comprising:
comparing the difference in the amount of transcription of the reporter gene in a cell in the presence of the compound with the amount of transcription in the absence of the compound, or with the amount of transcription in the absence of the heterologous calcium channel, whereby compounds that modulate the activity of the heterologous calcium channel in the cell are identified, wherein;

the cell comprises nucleic acid that encodes a reporter gene construct containing a reporter gene in operative linkage with one or more transcription control elements that is regulated by a calcium channel and furthermore the cell is a eukaryotic cell comprising heterologous nucleic acid comprising the coding portion of the sequence of nucleotides set forth in SEQ ID NOs: 49, 51 or 52.

35. The nucleic acid molecule of claim 1, wherein the calcium channel is a mammalian calcium channel.

36. The nucleic acid molecule of claim 1, wherein the calcium channel is a human calcium channel.

37. The isolated nucleic acid of claim 2, comprising the coding portion of the sequence of nucleotides set forth in SEQ ID NO: 49.

38. The isolated nucleic acid of claim 2, comprising the coding portion of the sequence of nucleotides set forth in SEQ ID NO: 51.

39. The isolated nucleic acid of claim 2, comprising the coding portion of the sequence of nucleotides set forth in SEQ ID NO: 52.

40. The isolated nucleic acid of claim 1, comprising a sequence of nucleotides that encodes the sequence of amino acids encoded by SEQ ID NOs: 49, 51, or 52.

41. The isolated nucleic acid of claim 40, comprising a sequence of nucleotides that encodes the sequence of amino acids encoded by SEQ ID NO: 49.

42. The isolated nucleic acid of claim 40, comprising a sequence of nucleotides that encodes the sequence of amino acids encoded by SEQ ID NO: 51.

43. The isolated nucleic acid of claim 40, comprising a sequence of nucleotides that encodes the sequence of amino acids encoded by SEQ ID NO: 52.

44. The eukaryotic cell of claim 5 into which has been further introduced:
a $\beta$-subunit having an amino acid sequence selected from the group consisting of the coding regions of SEQ ID NOs: 9, 10, 19, 20, 26, 27, 33, 34, 35 and 38;
an $\alpha_2$-subunit having an amino acid sequence selected from the group consisting of the coding regions of SEQ ID NOs: 11, 29, 30, 31, and 32; or
a $\gamma$-subunit having an amino acid sequence set forth by the coding region of SEQ ID NO: 14.

45. The eukaryotic cell of claim 13 into which has been further introduced:
a $\beta$-subunit having an amino acid sequence selected from the group consisting of the coding regions of SEQ ID NOs: 9, 10, 19, 20, 26, 27, 33, 34, 35 and 38;
an $\alpha_2$-subunit having an amino acid sequence selected from the group consisting of the coding regions of SEQ ID NOs: 11, 29, 30, 31, and 32; and
a $\gamma$-subunit having an amino acid sequence selected from the group consisting of set forth by the coding region of SEQ ID NO: 14.

46. The eukaryotic cell of claim 13 where the only heterologous ion channels are calcium channels.

47. The eukaryotic cell of claim 44 where the only heterologous ion channels are calcium channels.

48. The eukaryotic cell of claim 45 where the only heterologous ion channels are calcium channels.

49. The eukaryotic cell of claim 5 where the heterologous nucleic acid is RNA.

50. The eukaryotic cell of claim 5 where the heterologous nucleic acid is DNA.

* * * * *